US011517595B2

(12) United States Patent
Rehberger et al.

(10) Patent No.: US 11,517,595 B2
(45) Date of Patent: *Dec. 6, 2022

(54) METHODS OF MICROBIAL TREATMENT OF POULTRY

(71) Applicant: Church & Dwight Co., Inc., Princeton, NJ (US)

(72) Inventors: Thomas Rehberger, Wauwatosa, WI (US); Evan Hutchison, Milwaukee, WI (US); Alexandra Smith, Greendale, WI (US); Joshua Rehberger, Milwaukee, WI (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,344

(22) Filed: Dec. 19, 2018

(65) Prior Publication Data

US 2019/0231828 A1    Aug. 1, 2019

Related U.S. Application Data

(62) Division of application No. 15/268,104, filed on Sep. 16, 2016, now Pat. No. 10,201,574.

(60) Provisional application No. 62/219,433, filed on Sep. 16, 2015.

(51) Int. Cl.
*A61K 35/742* (2015.01)
*A23K 10/10* (2016.01)
*A23K 50/75* (2016.01)
*A23K 50/70* (2016.01)
*A23K 10/18* (2016.01)
*A61K 38/16* (2006.01)
*A61K 35/00* (2006.01)

(52) U.S. Cl.
CPC ............ *A61K 35/742* (2013.01); *A23K 10/10* (2016.05); *A23K 10/18* (2016.05); *A23K 50/70* (2016.05); *A23K 50/75* (2016.05); *A61K 38/164* (2013.01); *A61K 2035/11* (2013.01)

(58) Field of Classification Search
CPC .... A61K 35/742; A61K 38/164; A23K 10/10; A23K 50/70; A23K 50/75
See application file for complete search history.

(56) References Cited

U.S. PATENT DOCUMENTS

| | | | |
|---|---|---|---|
| 6,051,219 A | 4/2000 | Kubota | |
| 6,140,106 A | 10/2000 | Lawler et al. | |
| 6,162,634 A | 12/2000 | Lawler et al. | |
| 6,162,635 A | 12/2000 | Lawler et al. | |
| 6,422,174 B1 | 7/2002 | Horikawa et al. | |
| 6,660,294 B2 | 12/2003 | Maruta et al. | |
| 6,812,022 B1 | 11/2004 | Aonuma | |
| 6,989,370 B2 | 1/2006 | Fahrlander et al. | |
| 7,247,299 B2 | 7/2007 | Lin et al. | |
| 7,618,640 B2 | 11/2009 | Rehberger et al. | |
| 7,754,469 B2 | 7/2010 | Baltzley et al. | |
| 8,021,654 B2 | 9/2011 | Rehberger et al. | |
| 8,420,138 B2 | 4/2013 | Knap et al. | |
| 8,455,238 B2 | 6/2013 | Baltzley et al. | |
| 8,506,951 B2 | 8/2013 | Rehberger et al. | |
| 8,540,981 B1 | 9/2013 | Wehnes et al. | |
| 8,642,317 B2 | 2/2014 | Zhou et al. | |
| 8,722,058 B2 | 5/2014 | Rehberger et al. | |
| 8,741,280 B2 | 6/2014 | Cantor et al. | |
| 8,802,079 B2 | 8/2014 | Knap et al. | |
| 9,005,601 B2 | 4/2015 | Hargis et al. | |
| 9,011,836 B2 | 4/2015 | Rehberger et al. | |
| 9,089,151 B2 | 7/2015 | Davis et al. | |
| 9,144,588 B2 | 9/2015 | Ruhbio et al. | |
| 9,179,693 B2 | 11/2015 | Romero | |
| 9,247,757 B2 | 2/2016 | Schmidt et al. | |
| 10,834,942 B2 * | 11/2020 | Davis .................. | A61K 35/742 |
| 2009/0280090 A1 * | 11/2009 | Rehberger ............. | A61K 35/74 424/93.2 |
| 2014/0037582 A1 | 2/2014 | Romero et al. | |
| 2015/0079058 A1 | 3/2015 | Nielsen et al. | |
| 2015/0118203 A1 | 4/2015 | Boyette et al. | |
| 2015/0216915 A1 | 8/2015 | Frouel et al. | |
| 2015/0230498 A1 | 8/2015 | Davis et al. | |
| 2015/0250831 A1 | 9/2015 | Rehberger et al. | |
| 2015/0257400 A1 | 9/2015 | Reuter et al. | |
| 2015/0290254 A1 | 10/2015 | Remus et al. | |
| 2015/0306154 A1 | 10/2015 | Davis et al. | |

(Continued)

FOREIGN PATENT DOCUMENTS

WO    WO 2015/160960 A1    10/2015
WO    WO 2015/175667 A1    11/2015

(Continued)

OTHER PUBLICATIONS

U.S. Appl. Nos. 15/601,656; 15/605,484; 15/950,750 (Year: 2017).*
U.S. Appl. No. 17/029,672 (Year: 2020).*
Achanta, M., et al. (2012). Tissue expression and developmental regulation of chicken cathelicidin antimicrobial peptides. J. Anim. Sci. Biotechnol. 3, 15.
Agunos. A., et al. (2013). Antimicrobial therapy of selected diseases in turkeys, laying hens, and minor poultry Species in Canada. Can. Vet. J. 54, 1041-1052.
Aliakbarpour, H.R., et al. (2012). The Bacillus subtilis and Lactic Acid Bacteria Probiotics Influences Intestinal Mucin Gene Expression, Histomorphology and Growth Performance in Broilers. Asian-Australas. J. Anim. Sci. 25, 1285-1293.

(Continued)

Primary Examiner — Ruth A Davis
(74) Attorney, Agent, or Firm — Church & Dwight Co., Inc.

(57) ABSTRACT

Disclosed are methods of administering one or more *Bacillus* strains to poultry. The *Bacillus* strains improve bacterial homeostasis in the gastrointestinal tract by inhibiting bacterial pathogens such as *E. coli* and *Clostridium*. Administering the *Bacillus* strains also improves performance such as weight gain and feed conversion. Useful combinations of *Bacillus* strains and methods of using one or more *Bacillus* strains are also provided.

10 Claims, 8 Drawing Sheets

Specification includes a Sequence Listing.

(56) References Cited

U.S. PATENT DOCUMENTS

2016/0007614 A1 1/2016 Rubio et al.
2016/0120919 A1 5/2016 Ashida et al.

FOREIGN PATENT DOCUMENTS

| WO | WO 2016/022779 A1 | 2/2016 |
| WO | WO 2016/030441 A1 | 3/2016 |
| WO | WO 2016/060934 A1 | 4/2016 |
| WO | WO 2016/060935 A2 | 4/2016 |
| WO | WO 2016/118840 A1 | 7/2016 |
| WO | WO 2016/118850 A1 | 7/2016 |
| WO | WO 2016/118864 A1 | 7/2016 |

OTHER PUBLICATIONS

Allen, H.K., and Stanton, T.B. (2014). Altered Egos: Antibiotic Effects on Food Animal Microbiomes. Annu. Rev. Microbiol. 68, 297-315.

Al-Sheikhly, F., and Truscott, R.B. (1977a). The interaction of Clostridium perfringens and its toxins in the production of necrotic enteritis of chickens. Avian Dis. 21, 256-263.

Al-Sheikhly, F., and Truscott, R.B. (1977b). The pathology of necrotic enteritis of chickens following infusion of broth cultures of Clostridium perfringens into the duodenum. Avian Dis. 21, 230-240.

Bai, K., et al. (2016). Supplemental effects of probiotic Bacillus subtilis fmbJ on growth performance, antioxidant capacity, and meat quality of broiler chickens. Poult. Sci. pew246.

Barbosa, T.M., et al. (2005). Screening for Bacillus Isolates in the Broiler Gastrointestinal Tract. Appl. Environ. Microbiol. 71, 968-978.

Barnes, HJ, Nolan L, and Vaillancourt J-P (2008). Colibacillosis. In Diseases of Poultry, Saif YM, Fadly AA, Glisson JR, McDougald LR, Nolan L, and Swayne DE, eds. (Ames, IA: ISU Press), pp. 691-732.

Billington, S.J., et al., (1998). Clostridium perfringens type E animal enteritis isolates with highly conserved, silent enterotoxin gene sequences. Infect. Immun. 66, 4531-4536.

Blom, J., et al. (2016). EDGAR 2.0: an enhanced software platform for comparative gene content analyses. Nucleic Acids Res. 44, W22-W28.

Cartman, S.T., (2008). Bacillus subtilis Spores Germinate in the Chicken Gastrointestinal Tract. Appl. Environ. Microbial. 74, 5254-5258.

Chen, X.H., et al. (2007). Comparative analysis of the complete genome sequence of the plant growth-promoting bacterium Bacillus amyloliquefaciens FZB42. Nat. Biotechnol. 25, 1007-1014.

Cheng, G., et al., (2014), Antibiotic alternatives: the substitution of antibiotics in animal husbandry? Frontiers in Microbiology, vol. 5(217), pp. 1-13.

Chowdhury, S.P., et al. (2015). Biocontrol mechanism by root-associated Bacillus amyloliquefaciens FZB42—a review. Front. Microbial. 6.

Cooper, K.K., and Songer, J.G. (2009). Necrotic enteritis in chickens: a paradigm of enteric infection by Clostridium perfringens type A. Anaerobe 15, 55-60.

Cooper, K.K., Songer, J.G., and Uzal, F.A. (2013). Diagnosing clostridial enteric disease in poultry. J. Vet. Diagn. Invest. 25, 314-327.

Darling, A.E., Mau, B., and Perna, N.T. (2010). progressiveMauve: Multiple Genome Alignment with Gene Gain, Loss and Rearrangement. PLOS ONE 5, e11147.

Fan, B., et al. (2015). dRNA-Seq Reveals Genomewide TSSs and Noncoding RNAs of Plant Beneficial Rhizobacterium Bacillus amyloliquefaciens FZB42. PLoS ONE 10.

Fass (2010). Federation of Animal Science Societies—Guide for the Care and Use of Agricultural in Research and Teaching, Third Edition, Jan. 2010.

Fleischmann, R., et al. (1995). Whole-genome random sequencing and assembly of Haemophilus influenzae Rd. Science 269, 496.

Fritts, C.A., Kersey, J.H., Motl, M.A., Kroger, E.G., Yan, F., Si, J., Jiang, Q., Campos, M.M., Waldroup, A.L., and Waldroup, P.W. (2000). Bacillus subtilis C-3102 (Calsporin) Improves Live Performance and Microbiological Status of Broiler Chickens. J. Appl. Poult. Res. 9, 149-155.

Geeraerts, S., et al. (2016). Vegetative Bacillus amyloliquefaciens cells do not confer protection against necrotic enteritis in broilers despite high antibacterial activity of its supernatant against Clostridium perfringens in vitro. Br. Poult. Sci. 57, 324-329.

Glisson, J.R., et al. (2004). Comparative efficacy of enrofloxacin, oxytetracycline, and sulfadimethoxine for the control of morbidity and mortality caused by Escherichia coli in broiler chickens. Avian Dis. 48, 658-662.

Grave, K., et al. (2004). What has happened in norway after the ban of avoparcin? Consumption of antimicrobials by poultry. Prev. Vet. Med. 62, 59-72.

Guabiraba, R., and Schouler, C. (2015). Avian colibacillosis: still many black holes. FEMS Microbiol. Lett. 362, fnv118.

Hatheway, C.L. (1990). Toxigenic clostridia. Clin. Microbiol. Rev. 3, 66-98.

Heier B.t., et al. (2001). A field study of naturally occuring specific antibodies against Clostridium perfringens alpha toxin in Norwegian broiler flocks. Avian Dis. 45, 724-732.

Hibberd, M.C., et al. (2011). Multilocus Sequence Typing Subtypes of Poultry Clostridium perfringens Isolates Demonstrate Disease Niche Partitioning. J. Clin. Microbiol. 49, 1556-1567.

Hofacre, C.L., et al. (1998). Use of Aviguard and other intestinal bioproducts in experimental Clostridium perfringens-associated necrotizing enteritis in broiler chickens. Avian Dis. 42, 579-584.

Hofacre, C.L., et al. (2002). Effect of a commercial competitive exclusion culture on reduction of colonization of an antibiotic-resistant pathogenic Escherichia coli in day-old broiler chickens. Avian Dis. 46, 198-202.

Hong, H.A., (2005). The use of bacterial spore formers as probiotics. FEMS Microbial. Rev. 29, 813-835.

Immerseel, F.V., et al. (2004). Clostridium perfringens in poultry: an emerging threat for animal and public health. Avian Pathol. 33, 537-549.

Immerseel, F. V., et al. (2009). Rethinking our understanding of the pathogenesis of necrotic enteritis in chickens. Trends Microbiol. 17, 32-36.

Jayaraman, S., et al., "Bacillus subtilis PB6 improves intestinal health of broiler chickens challenged with Clostridium perfringens-induced necrotic enteritis," Poultry Science Association, 2013, vol. 92(2), pp. 370-374.

Jeong, J.S., and Kim, I.H. (2014). Effect of Bacillus subtilis C-3102 spores as a probiotic feed supplement on growth performance, noxious gas emission, and intestinal microflora in broilers. Poult. Sci. 93, 3097-3103.

Jeong, H., Park, S.-H., and Choi, S.-K. (2015). Genome Sequence of Antibiotic-Producing Bacillus anyloliquefaciens Strain KCTC 13012. Genome Announc. 3.

Jiang, Z., et al. (2010). Net effect of an acute phase response—Partial alleviation with probiotic supplementation. Poult. Sci. 89, 28-33.

Johnson, T.J., et al. (2008). Identification of Minimal Predictors of Avian Pathogenic Escherichia coli Virulence for Use as a Rapid Diagnostic Tool. J.Clin. Microbiol. 46, 3987-3996.

Jost, B.H., et al. (2005). Atypical cpb2 Genes, Encoding Beta2-Toxin in Clostridium perfringens Isolates of Nonporcine Origin. Infect. Immun. 73, 652-656.

Kaldhusdal, M., Benestad, S.L., and Løvland, A. (2016). Epidemiologic aspects of necrotic enteritis in broiler chickens—disease occurrence and production performance. Avian Pathol. 45, 271-274.

Kearse, M., et al. (2012). Geneious Basic: An integrated and extendable desktop software platform of the organizations and analysis of sequence data. Bioinformatics 28, 1647-1649.

Kennedy, C.L., et al. (2005). The a-toxin of Clostridium septicum is essential for virulence: a-toxin of Clostridium septicum. Mol. Microbiol. 57, 1357-1366.

Keyburn, A.L., et al. (2008). NetB, a New Toxin That Is Associated with Avian Necrotic Enteritis Caused by Clostridium perfringens. PLoS Pathog. 4, e26.

(56) References Cited

OTHER PUBLICATIONS

Keyburn, A.L., et al. (2010a). NetB, a pore-forming toxin from necrotic enteritis strains of Clostridium perfringens. Toxins 2, 1913-1927.

Keyburn, A.L., et al. (2010b). Association between avian necrotic enteritis and Clostridium perfringens strains expressing NetB toxin. Vet. Res. 41, 21.

Koumoutsi, A., et al. (2004). Structural and Functional Characterization of Gene Clusters Directing Nonribosomal Synthesis of Bioactive Cyclic Lipopeptides in Bacillus amyloliquefaciens Strain FZB42. J. Bacteriol. 186, 1084-1096.

La Ragione, R.M., and Woodward, M.J. (2003). Competitive exclusion by Bacillus subtilis spores of *Salmonella enterica* serotype Enteritidis and Clostridium perfringens in young chickens. Vet. Microbiol. 94, 245-256.

La Ragione, R.M., et al. (2001). Bacillus subtilis spores competitively exclude *Escherichia coli* O78:K80 in poultry. Vet. Microbiol. 79, 133-142.

Lazarus, B., et al. (2015). Do Human Extraintestinal *Escherichia coli* Infections Resistant to Expanded-Spectrum Cephalosporins Originate From Food-Producing Animals? A Systematic Review. Clin. Infect. Dis. 60, 439-452.

Lee, K.W., et al. (2010). Effects of direct-fed microbials on growth performance, gut morphometry, and immune characteristics in broiler chickens. Poult. Sci. 89, 203-216.

Lee, K.W., et al. (2011a). Avian necrotic enteritis: Experimental models, host immunity, pathogenesis, risk factors, and vaccine development. Poult. Sci. 90, 1381-1390.

Lee, K.-W., et al. (2011b). Bacillus subtilis-based direct-fed microbials augment macrophage function in broiler chickens. Res. Vet. Sci. 91, e87-e91.

Lee, K.W., et al. (2013). Effect of Bacillus subtilis-based Direct-fed Microbials on Immune Status in Broiler Chickens Raised on Fresh or Used Litter. Asian-Australas. J. Anim. Sci. 26, 1592-1597.

Lee, K.-W., et al. (2014). Effects of salinomycin and Bacillus subtilis on growth performance and immune responses in broiler chickens. Res. Vet. Sci. 97, 304-308.

Li, B., et al. (2014). Responses of beneficial Bacillus amyloliquefaciens SQR9 to different soilborne fungal pathogens through the alteration of antifungal compounds production. Front. Microbial. 5.

Li, Y., et al. (2016). Effect of Bacillus subtilis CGMCC 1.1086 on the growth performance and intestinal microbiota of broilers. J. Appl. Microbial. 120, 195-204.

Lovland, A., et al. (2003). Diagnosing Clostridium perfringens-associated necrotic enteritis in broiler flocks by an immunoglobulin G anti-alpha-toxin enzyme-linked immunosorbent assay. Avian Pathol. 32, 527-534.

Lovland, A., et al. (2004). Maternal vaccination against subclinical necrotic enteritis in broilers. Avian Pathol. 33, 81-90.

Lu, J., et al. (2003). Diversity and Succession of the Intestinal Bacterial Community of the Maturing Broiler Chicken. Appl. Environ. Microbial. 69, 6816-6824.

Luo, C., et al. (2015a). Nonribosomal Peptide Synthase Gene Clusters for Lipopeptide Biosynthesis in Bacillus subtilis 916 and Their Phenotypic Functions. Appl. Environ. Microbial. 81, 422-431.

Luo, C., et al. (2015b). Unusual Biosynthesis and Structure of Locillomycins from Bacillus subtilis 916. Appl. Environ. Microbiol. 81, 6601-6609.

Marsh, T.L., et al. (2000). Terminal Restriction Fragment Length Polymorphism Analysis Program, a Web-Based Research Tool for Microbial Community Analysis. Appl. Environ. Microbiol. 66, 3616-3620.

Maurer, J.J., et al. (2002). Virulence factors associated with *Escherichia coli* present in a commercially produced competitive exclusion product. Avian Dis. 46, 704-707.

Moran, E.T. (2014). Intestinal events and nutritional dynamics predispose Clostridium perfringens virulence in broilers. Poult. Sci. 93, 3028-3036.

Muller, P.Y., et at (2002). Processing of gene expression data generated by quantitative real-time RT-PCR. BioTechniques 32, 1372-1374, 1376, 1378-1379.

Neumann, A.P., and Rehberger, T.G. (2009). MLST analysis reveals a highly conserved core genome among poultry isolates of Clostridium septicum. Anaerobe 15, 99-106.

Neumann, A.P., et al. (2010). Quantitative real-time PCR assay for Clostridium septicum in poultry gangrenous dermatitis associated samples. Mol. Cell. Probes 24, 211-218.

Nguyen, A. t. v., et al. (2015). Isolation and characterization of Bacillus subtilis CH16 strain from chicken gastrointestinal tracts for use as a feed supplement to promote weight gain in broilers. Lett. Appl. Microbiol. 60, 580-588.

Niilo, L. (1980). Clostridium perfringens in Animal Disease: A Review of Current Knowledge. Can. Vet. J. 21, 141-148.

Nurk, S., et al. (2013). Assembling Genomes and Minimetagenomes from Highly Chimeric Reads. In Research in Computational Molecular Biology, M. Deng, R. Jiang, F. Sun, and X. Zhang, eds. (Springer Berlin Heidelberg), pp. 158-170.

Park, J.H., and Kim, I.H. (2014). Supplemental effect of probiotic Bacillus subtilis B2A on productivity, organ weight, intestinal *Salmonella* microflora, and breast meat quality of growing broiler chicks. Poult. Sci. 93, 2054-2059.

Park, J.H., and Kim, I.H. (2015). The effects of the supplementation of Bacillus subtilis RX7 and B2A strains on the performance, blood profiles, intestinal *Salmonella* concentration, noxious gas emission, organ weight and breast meat quality of broiler challenged with *Salmonella typhimurium*. J. Anim. Physiol. Anim. Nutr. 99, 326-334.

Patterson, J.A., and Burkholder, K.M. (2003). Application of prebiotics and probiotics in poultry production. Poult. Sci. 82, 627-631.

Power, E.G. (1996). RAPD typing in microbiology—a technical review. J. Hosp. Infect. 34, 247-265.

Primm, N.D., et al. (1997). Application of normal avian gut flora by prolonged aerosolization onto turkey hatching eggs naturally exposed to *Salmonella*. Avian Dis. 41, 455-460.

Rahimi, S., et al. (2011). Effect of direct-fed microbials on performance and Clostridium perfringens colonization of turkey poults. Poult. Sci. 90, 2656-2662.

Riley, M.A., et al. (2012). Resistance is futile: the bacteriocin model for addressing the antibiotic resistance challenge. Biochem. Soc. Trans. 40, 1438-1442.

Rimoldi, G., et al. (2015). Necrotic Enteritis in Chickens Associated with Clostridium sordellii. Avian Dis. 59, 447-451.

Rood, J.I., et al. (2016). NetB and necrotic enteritis: the hole movable story. Avian Pathol. J. WVPA 45, 295-301.

Seemann, T. (2014). Prokka: rapid prokaryotic genome annotation. Bioinformatics 30, 2068-2069.

Sen, S., et al. (2012). Effect of supplementation of Bacillus subtilis LS 1-2 to broiler diets on growth performance, nutrient retention, caecal microbiology and small intestinal morphology. Res. Vet. Sci. 93, 264-268.

Shojadoost, B., et al. (2012). The successful experimental induction of necrotic enteritis in chickens by Clostridium perfringens: a critical review. Vet. Res. 43, 74.

Smirnov, A., Perez, R., Amit-Ramach, E., Sklan, D., and Uni, Z. (2005). Mucin Dynamics and Microbial Populations in Chicken Small Intestine Are Changed by Dietary Probiotic and Antibiotic Growth Promoter Supplementation. J. Nutr. 135, 187-192.

Snoeyenbos, G.H., et al. (1978). Protecting chicks and poults from *Salmonellae* by oral administration of "normal" gut microflora. Avian Dis. 22, 273-287.

Songer, J.G. (1996). Clostridial enteric diseases of domestic animals. Clin Microbial. Rev. 9, 216-234.

Tagg, J.R., Dajani, et al. (1976). Bacteriocins of gram-positive bacteria. Bacterial. Rev. 40, 722-756.

Tam, N.K.M., et al. (2006). The Intestinal Life Cycle of Bacillus subtilis and Close Relatives. J. Bacterial. 188, 2692-2700.

Tellez, G., et al. (2012). Probiotics/direct fed microbials for *Salmonella* control in poultry. Food Res. Int. 45, 628-633.

(56) References Cited

OTHER PUBLICATIONS

Teo, A.Y.-L., and Tan, H.-M. (2005). Inhibition of Clostridium perfringens by a Novel Strain of Bacillus subtilis Isolated from the Gastrointestinal Tracts of Healthy Chickens. Appl. Environ. Microbial. 71, 4185-4190.

Timbermont, L., Haesebrouck, F., Ducatelle, R., and Immerseel, F.V. (2011). Necrotic enteritis in broilers: an updated review on the pathogenesis. Avian Pathol. 40, 341-347.

Uzal, F.A., McClane, B.A., Cheung, J.K., Theoret, J., Garcia, J.P., Moore, R.J., and Rood, J.I. (2015). Animal models to study the pathogenesis of human and animal Clostridium perfringens infections. Vet. Microbial. 179, 23-33.

Wattam, A., Gabbard, J., Shukla, M., and Sobral, B. (2014). Comparative Genomic Analysis at the PATRIC, A 42 Bioinformatic Resource Center. In Host-Bacteria Interactions, A.C. Vergunst, and D. O'Callaghan, eds. (Springer New York), pp. 287-308.

Wattiau, P., Renard, M.E., Ledent, P., Debois, V., Blackman, G., and Agathos, S.N. (2001). A PCR test to identify 43 bacillus subtilis and closely related species and its application to the monitoring of wastewater biotreatment. Appl. Microbial. Biotechnol. 56, 816-819.

Weinack, O.M., Snoeyenbos, G.H., Smysere, C.F., and Soerjadi, A.S. (1981). Competitive exclusion of intestinal colonization of *Escherichia coli* in chicks. Avian Dis. 25, 696-705.

WHO Global Strategy Recommendations http://www.who.int/drugresistance/ WHO_ Global_ Strategy_Recommendations/en/index3.html.

Williams, J.G.K., Kubelik, A.R., Livak, K.J., Rafalski, J.A., and Tingey, S.V. (1990). DNA polymorphisms amplified by arbitrary primers are useful as genetic markers. Nucleic Acids Res. 18, 6531-6535.

Willoughby, D.H., Bickford, A.A., Cooper, G.L., and Charlton, B.R. (1996). Periodic Recurrence of Gangrenous Dermatitis Associated with Clostridium Septicum in a Broiler Chicken Operation. J. Vet. Diagn. Invest. 8, 259-261.

Wu, L., Wu, H.-J., Qiao, J., Gao, X., and Borriss, R. (2015). Novel Routes for Improving Biocontrol Activity of Bacillus Based Bioinoculants. Front. Microbiol. 6.

Yogaratnam, V. (1995). Analysis of the causes of high rates of carcase rejection at a poultry processing plant. Vet. Rec. 137, 215-217.

Yoo, H., et al., "Molecular typing and epidemiological survey of prevalence of Clostridium perfringens types by multiplex PCR," *J. Clin. Microbial.*, (1997) vol. 35(I), pp. 228-232.

Zeriouh, H., de Vicente, A., Perez-Garcia, A., and Romero, D. (2014). Surfactin triggers biofilm formation of Bacillus subtilis in melon phylloplane and contributes to the biocontrol activity. Environ. Microbial. 16, 2196-2211.

Zhang, Z.F., and Kim, I.H. (2014). Effects of multistrain probiotics on growth performance, apparent ilea! nutrient digestibility, blood characteristics, cecal microbial shedding, and excreta odor contents in broilers. Poult. Sci. 93, 364-370.

Zhang, J., Kobert, k, Flouri, T., and Stamat2akis, A. (2014). PEAR: A fast and accurate Illumina Paired-End reAd mergeR. Bioinformatics 30, 614-620.

Zhu, Z.Y., Zhong, T., Pandya, Y., and Joerger, R.D. (2002). 16S rRNA-Based Analysis of Microbiota from the Cecum of Broiler Chickens. Appl. Environ. Microbial. 68, 124-137.

Pranto, et al., "Enhancing antimicrobial activity of chitosan films by incorporating garlic oil, potassium sorbate and nisin," *LWT—Food Science and Technology*, Academic Press, United Kingdom, 2005, vol. 38(8), pp. 859-865.

Veerapandian, et al., "Analytical and biological characterization of quinazoline semicarbazone derivatives," *Med. Chem. Res.* , 2009, vol. 19(3), pp. 283-298.

International Search Report and Written Opinion for PCT/US2017/034512, dated 2017, 16 pages.

\* cited by examiner

METHODS OF MICROBIAL TREATMENT OF POULTRY

CROSS-REFERENCE TO RELATED APPLICATIONS

The present application is a divisional of U.S. application Ser. No. 15/268,104, filed on Sep. 16, 2016, which claims priority to U.S. Provisional Application No. 62/219,433, filed on Sep. 16, 2015, the entire specification of each being incorporated herein by reference.

SEQUENCE LISTING

The instant application contains a Sequence Listing which has been filed electronically in ASCII format and is hereby incorporated by reference in its entirety. Said ASCII copy, created on Mar. 13, 2019, is named 99341 DIV_Seq_List.txt, and is 10,259 bytes in size.

BIBLIOGRAPHY

Complete bibliographic citations of those references that are referred to herein by the first author's last name and year of publication in parentheses can be found in the Bibliography section, which precedes the claims.

FIELD OF THE INVENTION

This invention relates to compositions of novel microorganisms for improving gastrointestinal homeostatis by reducing bacterial pathogens, stimulating the host immune function and thus reducing poultry diseases and enhancing health and performance.

BACKGROUND OF THE INVENTION

Conventional poultry production uses antibiotics to prevent disease and stimulate animal growth. Over time as a group of animals is continually fed sub-therapeutic levels of antibiotics to enhance their growth, susceptible bacteria within the gastrointestinal tract of these animals will develop resistance. When these bacteria are ingested via improperly handled meat it is possible for individuals to become ill, and such individuals may not respond to treatment with antibiotics that are the same or similar to those fed to the animals. Therefore, it is recommended that antibiotics used to treat human illnesses not be administered to food animals. The World Health Organization (WHO) urges efforts to phase out antimicrobials that are used to treat humans for growth promotion in livestock (WHO Global Strategy Recommendations). Motivated by health concerns over the potential of antibiotic resistance bacteria in the food supply, environmental concerns, animal welfare and quality concerns, many consumers are seeking alternatives to conventional meat products that are typically produced with routine use of antibiotics (Allen and Stanton, 2014; Cheng et al., 2014). Accordingly, consumer demand for chicken and turkey that has been raised without the use of antibiotics is growing to the point that production of poultry raised without the routine use of antibiotics has become part of the mainstream.

Common bacterial disease challenges facing poultry that are conventionally treated with antibiotics include colibacillosis caused by Avian Pathogenic *Escherichia coli* (APEC), as well as enteric diseases caused by various species from the *Clostridium* genus.

Although *Escherichia coli* are normal residents of the gastrointestinal tract in poultry, some strains carry virulence genes and are able to cause colibacillosis in birds. These virulent *E. coli* strains, known as Avian Pathogenic *Escherichia coli* (APEC), are a heterogeneous group comprising a wide diversity of serotypes and containing an array of virulence genes (Guabiraba and Schouler, 2015). Collibacillosis in poultry may be localized or systemic and includes disease states such as colisepticemia, coligranuloma (Hjarre's disease), air sac disease (chronic respiratory disease, CRD), swollen-head syndrome, venereal colibacillosis and coliform cellulitis (inflammatory process), peritonitis, salpingitis, orchitis, osteomyelitis/synovitis (turkey osteomyelitis complex), panophthalmitis, omphalitis/yolk sac infection and enteritis (Barnes H J et al., 2008). Although difficult to quantify these various disease forms are responsible for significant economic losses in poultry. For instance, lesions consistent with colisepticemia were present on 43% of broiler carcasses condemned at processing. A reduction in the levels of APEC strains will reduce rates of disease and have a positive effect on the productivity of commercial broiler operations.

Necrotic enteritis, caused by *C. perfringens*, is the most common and severe clostridial enteric disease in poultry (Barnes H J, 2008; Cooper et al., 2013). Necrotic enteritis outbreaks are sporadic, but typically occur in broilers between 2-6 weeks of age (Cooper et al., 2013). It has been estimated that global necrotic enteritis outbreaks result in a loss of over $2 billion annually through increased medical costs, reduced weight gain and mortality amongst animals (Lee et al., 2011a; Timbermont et al., 2011). The characteristic intestinal lesions are generally considered to be caused by the production of alpha toxin by *C. perfringens* Type A (Al-Sheikhly and Truscott, 1977a, 1977b, 1977b) with NE toxin B (NetB) also having been implicated in disease (Keyburn et al., 2008, 2008, 2010a; Rood et al., 2016). *C. perfringens* is a normal resident of the intestinal tract of poultry usually at levels below $10^4$ CFU/g intestinal contents, but found at levels about $10^7$ CFU/g in diseased birds (Shojadoost et al., 2012). Therefore, maintaining low levels of *C. perfringens* can ameliorate the onset of disease. Furthermore, *C. perfringens* infections have been shown to increase when antibiotic growth promoters were removed from poultry feed in Scandinavian countries, and it is anticipated that the forthcoming removal of antibiotic growth promoters from poultry feed in the USA will have a similar effect (Grave et al., 2004; Immerseel et al., 2009; Kaldhusdal and Løvland, 2000).

Bacteriocins, small antimicrobial peptides produced by bacteria, are alternatives to common antibiotics in livestock production. The function of bacteriocins is to allow the producer cells to compete with other microbes in their natural environment. They generally increase membrane permeability by forming pores in membranes of target cells or inhibit cell wall synthesis thereby preventing growth of susceptible microbes. Other beneficial attributes of bacteriocins include resistance to low pH and heat and little, if any, negative effects on host cells. These bacterially produced antimicrobial peptides are very similar to those produced by the host organism itself. Cationic antimicrobial peptides, such as cathelicidins, are abundantly expressed in the mucosal epithelial cells lining the digestive, respiratory and reproductive tracts, as well as in the primary and secondary immune organs of chickens, where they play an essential role in innate defense and disease resistance (Achanta et al., 2012).

There may be concern that continual exposure of bacteria to continual, high levels of bacteriocins could result in resistance developing as it does for conventional antibiotics. This risk can be greatly reduced by the combined use of a number of bacteriocins with different mechanisms of action (Riley et al., 2012). Synergistic effects between the bacteriocins allow for lower doses and multiple spontaneous mutations will have to occur to acquire resistance to a combination of bacteriocins.

What is needed are bacterial strains and combinations of bacterial strains that are bacteriocin producing as to be useful in poultry and other animals. Methods of making and using bacteriocin producing bacterial strains and combinations thereof are also needed. Additionally, methods of identifying bacteriocin producing bacterial strains that are useful in poultry and other animals are also needed.

SUMMARY OF THE INVENTION

The present invention, is intended to solve one or more of the problems noted above.

In accordance with an embodiment of the present invention, a composition comprising at least one isolated *Bacillus* strain chosen from at least one of strains 747, 1104, 1781, 1541, and 2018 is provided. The composition, including the at least one isolated *Bacillus* strain may inhibit a pathogen chosen from at least one of *E. coli* and *Clostridium* in an animal.

In accordance with another embodiment of the present invention, the composition may comprise a plurality of isolated *Bacillus* strains chosen from the strains 747, 1104, 1781, 1541, and 2018.

In accordance with another embodiment of the present invention, the composition may comprise a plurality of isolated *Bacillus* strains chosen from the strains 747, 1104, 1781, 1541, 1999 and 2018.

In accordance with another embodiment of the present invention, the composition may further comprise a carrier selected from a group consisting of but not limited to: whey, maltodextrin, sucrose, dextrose, limestone, rice hulls, and sodium silica aluminate. The carrier may be in the physical of a powdered solid, a liquid, or a gel.

In accordance with another embodiment of the present invention, the composition may also comprise an animal feed, wherein the composition of the at least one isolated *Bacillus* strain in said composition is about $1 \times 10^8$ CFU/g.

In accordance with another embodiment of the present invention, the composition may also comprise a liquid, such as water, wherein the composition of the at least one isolated *Bacillus* strain in said composition is about $1 \times 10^8$ CFU/g.

In accordance with another embodiment of the present invention, a combination is provided including one or more of isolated *Bacillus* 747 (NRRL B-67257) or a strain having all of the identifying characteristics of *Bacillus* 747 (NRRL B-67257), *Bacillus* strain 1104 (NRRL B-67258) or a strain having all of the identifying characteristics of *Bacillus* strain 1104 (NRRL B-67258), *Bacillus* strain 1781 (NRRL B-67259) or a strain having all of the identifying characteristics of *Bacillus* strain 1781 (NRRL B-67250), *Bacillus* strain 1541 (NRRL B-67260) or a strain having all of the identifying characteristics of *Bacillus* strain 1541 (NRRL B-67260), and *Bacillus* strain 2018 (NRRL B-67261), *Bacillus* strain 1999 (NRRL B-67318) or a strain having all of the identifying characteristics of *Bacillus* strain 1999 (NRRL B-67318); and *Bacillus* strain 2018 (NRRL B-67261), or a strain having all of the identifying characteristics of *Bacillus* strain 2018 (NRRL B-67261).

The *Bacillus* strains identified herein according to one embodiment of the present invention, to inhibit pathogens, produce multiple compounds with inhibitory activity against other microbes with many strains containing more than ten operons producing antifungal and antibacterial compounds. Multiple bacteriocins are being produced in vitro directly at the site of action by the *Bacillus* strains so a robust blend of bacteriocins are present at doses lower than would be needed if isolated bacteriocins were being added directly to the feed.

Both in vitro data and in vivo trials indicate the effectiveness of these *Bacillus* strains in inhibiting poultry pathogens, such as APEC and *C. perfringens*, thereby decreasing the disease-burden in commercial broiler operations.

Accordingly, in accordance with another embodiment of the present invention, a method is provided comprising administering to an animal an effective amount of at least one isolated *Bacillus* strain chosen from the strains 747, 1104, 1781, 1541, and 2018 to inhibit a pathogen chosen from at least one of *E. coli* and *Clostridium* in the animal.

In accordance with another embodiment of the present invention, the animal may be a chicken or a turkey.

In accordance with another embodiment of the present invention, administering said strain or strains to said animal improves average daily weight gain relative to that in animals that have not been administered the strain or strains.

In accordance with another embodiment of the present invention, administering said strain or strains to a first group of said animals decreases mortality rate amongst the group of animals relative to that in second group of animals that have not been administered the strain or strains.

In accordance with another embodiment of the present invention, administering said strain or strains to said animal reduces a level of *C. perfringens* Type A in gastrointestinal tract tissue of the animal relative to that in animals that have not been administered the strain or strains.

In accordance with another embodiment of the present invention, the level of *C. perfringens* Type A in the treated animal is reduced by about 85.0% relative to that in animals that have not been administered the strain or strains.

In accordance with another embodiment of the present invention, the level of *C. perfringens* Type A in gastrointestinal tract tissue of the treated animal is less than about 50 CFU/g.

In accordance with another embodiment of the present invention, the occurrence of necrotic enteritis in the treated animal is reduced relative to that in animals that have not been administered the strain or strains according to the present invention.

In accordance with another embodiment of the present invention, administering said *Bacillus* strain or strains to said animal reduces a level of avian pathogenic *E. coli* (APEC) in gastrointestinal tract tissue of the animal relative to that in animals that have not been administered the strain or strains.

In accordance with another embodiment of the present invention, the level of avian pathogenic *E. coli* (APEC) in the treated animal is reduced by about 80.0%.

In accordance with another embodiment of the present invention, the occurrence of colibacillosis in the treated animal is reduced relative to that in animals that have not been administered the strain or strains.

In accordance with another embodiment of the present invention, the administering an effective amount of a plurality of isolated *Bacillus* strains increases a concentration of a plurality of bacteriocins in the gastrointestinal tract tissue of the animal.

In accordance with another embodiment of the present invention, the effective amount of plurality of isolated *Bacillus* strains are administered to the animal in the form of a direct fed microbial composition including a comprises a carrier.

In accordance with another embodiment of the present invention, administering an effective amount of a plurality of isolated *Bacillus* strains to the animal modulates the immune system of the treated animal.

In accordance with another embodiment of the present invention, the plurality of isolated *Bacillus* strains are chosen from the strains 747, 1104, 1781, 1541, 1999 and 2018.

Figure 1:
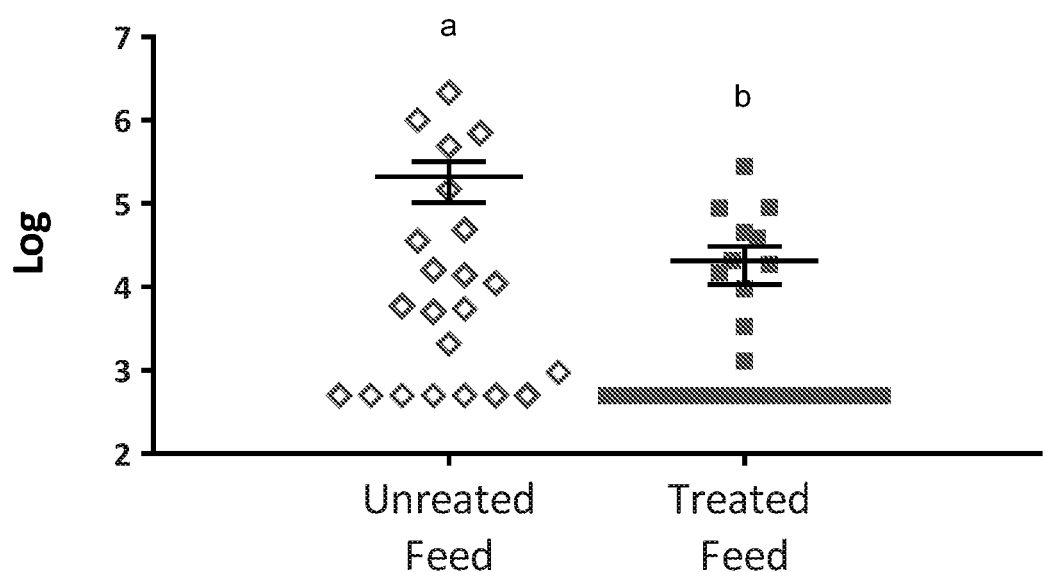
FIG. 1: Levels (CFU/g) of APEC in broiler GITs from untreated birds and birds treated with a direct fed microbial product according to one embodiment of the present invention. Black lines indicate mean with SEM. Superscripts of different letters denote significance ($P<0.05$ by unpaired, two-tailed t-test)
Figure 2:
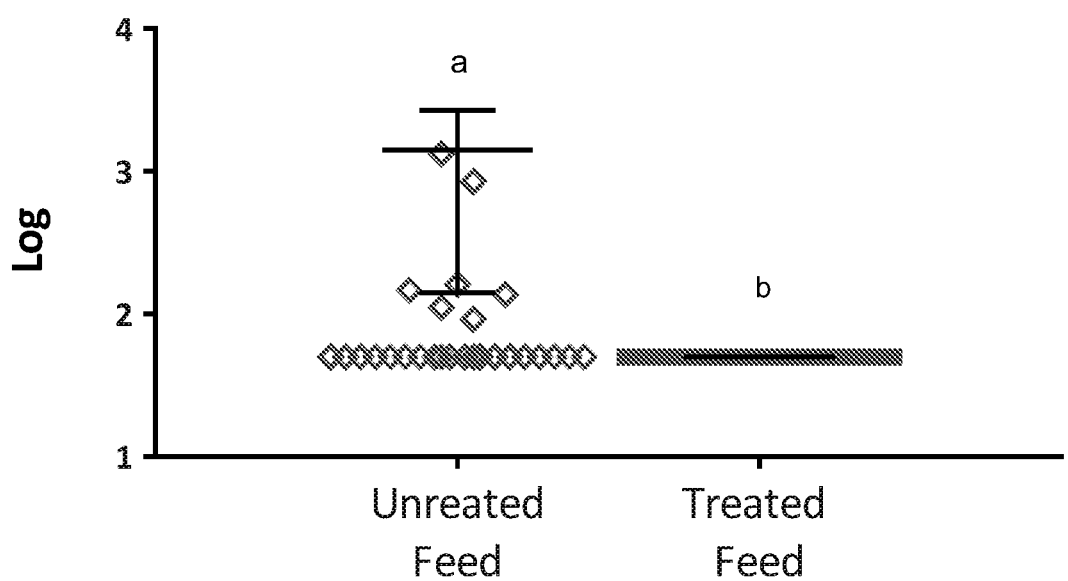
FIG. 2: Levels (CFU/g) of *C. perfringens* in broiler GITs from untreated birds and birds treated with a direct fed microbial product according to one embodiment of the present invention. Black lines indicate mean with SEM. Superscripts of different letters denote significance ($P<0.05$ by unpaired, two-tailed t-test)
Figure 3:
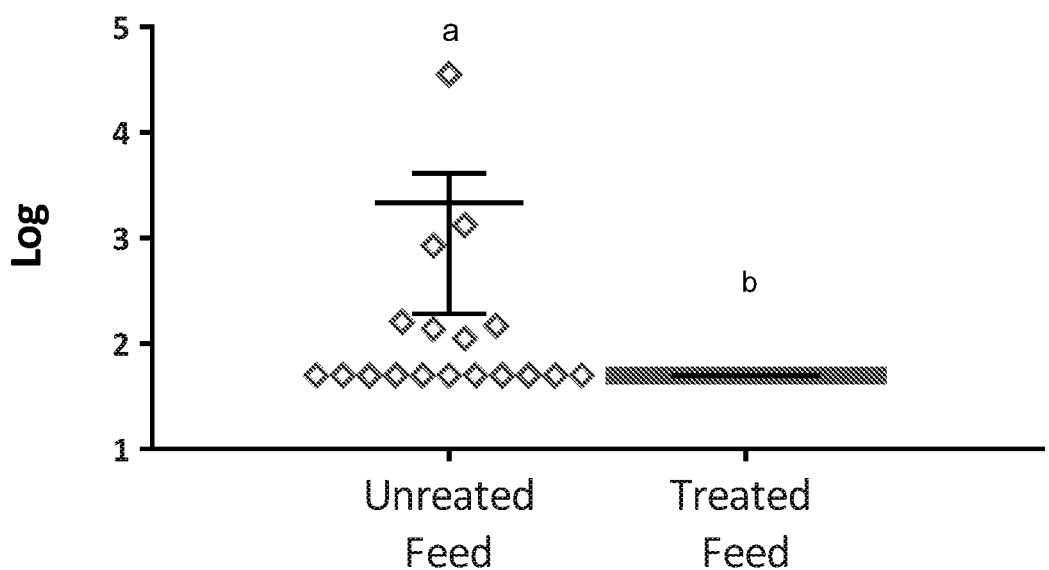
FIG. 3: Levels (CFU/g) of *Clostridium perfringens* in turkey GITs from untreated birds and birds treated with a direct fed microbial product according to one embodiment of the present invention. Black lines indicate mean with SEM. Superscripts of different letters denote significance ($P<0.05$ by unpaired, two-tailed t-test)

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

In accordance with the present invention, there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Bacterial strains useful for improving health and performance of poultry are provided in accordance with the present invention. In one embodiment of the invention, bacteria strains belong to the genus *Bacillus*. One or more Bacillus strains can be used in combination. The Bacillus strain(s) can be fed to poultry as a direct-fed microbial (DFM), dosed through the drinking water line or applied using a spray cabinet on newly hatched birds at the hatchery. Feeding or dosing one or more Bacillus strains described herein reduces bacterial pathogens of poultry, improves immune and gut barrier function and GI microbial homeostasis resulting in improved health and performance in poultry.

Bacillus Strains—Isolation and Characterization

Bacillus strains described herein were isolated from environmental sources including water, animal feed, fermented silages, poultry litter and soil. Samples were heat shocked to kill the vegetative bacterial populations and inoculated on general media to grow out the spore-forming bacteria into colonies. Plates were incubated at mesosphilic temperatures under aerobic conditions to inhibit the growth of anaerobic bacteria. Representative colonies were picked, grown in broth overnight and the resulting cell mass harvested and split for long-term storage and DNA isolation. Genomic DNA was harvested from each strain and used as a template for PCR of the 16S rRNA gene for strain identification and RAPD analysis to determine the relatedness among the strains. Strains identified as belonging to Bacillus species Generally Recognized As Safe (GRAS) were further tested for safety and selected based on functional pathogen inhibition assays.

Bacillus Strains—Selection

Bacillus strains were selected as candidates for use as Direct Fed Microbials (DFM) based on functional inhibitory assays against avian pathogenic E. coli and Clostridium perfringens. Alternatively, strains were selected using genetic screening techniques to identify strains with targeted antimicrobial genes. Both techniques were successful at identifying candidate Bacillus strains for DFM.

For functional testing, APEC and C. perfringens strains were isolated from poultry flocks and used as indicators in antimicrobial broth assays. Bacillus strains were grown overnight, cells removed by centrifugation and cell-free supernatants were prepared by filter sterilization. Antimicrobial assays contained indicator strains inoculated in growth medium and mixed with Bacillus supernatants. Assays were incubated overnight and the growth compared to assays of the same indicator strain without the Bacillus supernatants. The most effective inhibitory strains showing the highest growth inhibition against the broadest collection of APEC and C. perfringens indicator strains were identified and prepared for scale-up production.

Alternatively, Bacillus strains were selected based on presence of antimicrobial genes using genetic screening methods. Genes with known inhibitory activity were identified and primer sequences constructed. PCR reactions with genomic DNA from Bacillus strains and the constructed primers were used to identify strains with the antimicrobial gene of interest. Bacillus strains shown to produce the known PCR amplicon were chosen for functional antimicrobial screening. Strains confirmed to have the known activity were prepared for large-scale production.

Bacillus Strains—Beneficial Activities

Bacillus strains have a number of activities that make them efficacious for feeding poultry including the production of extracellular enzymes, antimicrobials and immune modulating molecules. In addition, Bacillus form endospores that make them stable in feed and other feed components. These spores are heat resistant and thus will survive normal feed pelleting processes. The spores are recalcitrant to drying and mineral salts making them stable in vitamin and trace mineral premixes.

The Bacillus strains described herein produce a number of different antimicrobials such as polyketides and lipopeptides as well as larger protein bacteriocin-like molecules that effectively inhibit enteric disease causing clostridia including C. perfringens and C. septicum. In addition, some of these of these antimicrobials are effective at inhibiting APEC isolates. Combining multiple Bacillus strains can effectively produce a DFM product for broad-spectrum control of important disease-causing bacteria in poultry.

In addition to the antimicrobial activities, Bacillus produce a number of extracellular enzymes including cellulase, hemicellulase, xylanase, amylase and proteases. These exogenous enzymes play a role in improving the utilization of some of the difficult to digest feed components such as non-starch polysaccharides which can have a negative impact on feed efficiency in poultry. These enzymes also alter the nutrient levels in the GI tract such as decreasing starch levels in the lower GI tract, which reduces the potential of proliferation of starch utilizing clostridia. Thus, the Bacillus enzyme activity plays a role in maintaining microbial gut homeostasis.

Other activities of the Bacillus that are important to improve poultry performance include the production of immune modulating molecules. Many factors such as diet changes, disease challenges and stress can affect gut health. These factors lead to the loss of structural integrity of the intestinal epithelium resulting in a decrease in the absorptive surface, increase in intestinal permeability and increase in inflammatory responses that ultimately reduce performance. Increased permeability directly results in the translocation of bacteria and their metabolic products into circulation. Feeding selected strains of Bacillus has been shown to alter intestinal immune activity and improve gut barrier integrity through increased expression of tight junction (TJ) proteins. Increased TJ protein expression in chickens fed Bacillus-supplemented diets translates to increased intestinal barrier function and optimal gut health.

Bacillus strains identified as being useful and containing one of more of these beneficial activities include strains 747, 1104, 1541, 1781, 1999 and 2018. These strains can be fed individually or in combination with each other.

Bacillus strains 747, 1104, 1541, 1781 and 2018 were deposited on May 24, 2016 at the Agricultural Research Service Culture Collection (NRRL), 1815 North University Street, Peoria, Ill., 61604 and given accession numbers NRRL B-67257 for strain 747, NRRL B-67258 for strain 1104, NRRL B-67260 for strain 1541, NRRL B-67259 for strain 1781 and NRRL B-67261 for strain 2018. Strain 1999 was deposited on Sep. 15, 2016 and given the accession number NRRL B-67318. All deposits were made under the provisions of the Budapest Treaty on the International Recognition of the Deposit of Microorganisms for the Purposes of Patent Procedure.

Bacillus as Direct-Fed Microbials

Administration of one or more Bacillus microorganisms to poultry may be accomplished by several methods including adding the Bacillus strains to the animals' feed, or drinking water, or to the bedding or litter, or by spraying on the chicks or poults at hatching such as by an aerosol or gels. Bacillus strains according to the present invention can be administered as a direct-fed microbial concentrate which is mixed into the feed as part of the vitamin mineral premix or as a separate inclusion into the feed or as a water soluble concentrate that is added to the drinking water system via a proportioner and diluted into the nipple drinkers. In addition, Bacillus strains can be administered to a newly hatched chick or poult via a spray aersol immediately after hatching and before placement on the farm.

Bacillus strains may be administered in various forms, for example as a feed supplement via the vitamin trace mineral premix or as a separate concentrate for mixing into the feed. In one embodiment of the feed supplement form, freeze-dried Bacillus fermentation product in the form of spores is added to a carrier, such as whey, maltodextrin, sucrose, dextrose, limestone (calcium carbonate), rice hulls, sodium silica aluminate. In one embodiment of the liquid drench, freeze-dried Bacillus spores product is added to a carrier, such as maltodextrin, sucrose, dextrose, dried starch, sodium silica aluminate, and a liquid used in a spray cabinet. In one embodiment of the gel form, freeze-dried Bacillus fermentation product is added to a carrier, such as starch or other or carbohydrates based gums, sucrose, silicon dioxide, polysorbate 80, propylene glycol and artificial coloring to form the gel.

The Bacillus strains are grown in a liquid broth containing protein, carbohydrates and minerals at a constant temperature and agitation to maximize the initial cell density. In the initial phase of the fermentation, the conditions are set to maximize the cell density and then in the later stages of the fermentation conditions are set to convert the cells to spores. In one embodiment, the strains are grown to an initial OD in Nutrient broth where the cell yield is at least $2\times10^9$ colony forming units (CFU) per ml of culture. Following the initial growth phase, agitation can be reduced, supplements added to induce sporulation and the cells convert to spore forms. Once the culture reaches a maximum spore density, the culture is harvested by separating the cells from the medium by centrifugation. Wet spore paste is then mixed with stabilizing agents such as starch, maltodextrin, citric acid and cryoprotectants if the paste is to be freeze-dried. The suspended spore paste is then dried and milled to provide a flowable powder.

To prepare compositions, the dried spore powder can be added to a carrier such as whey, maltodextrin, sucrose, dextrose, limestone (calcium carbonate), rice hulls, sodium silica aluminate in a ribbon or paddle mixer and mixed to produce an even distribution of the spores in the carrier. The components are blended such that a uniform mixture of the carrier and cultures result.

A preferred dosage for the premix or concentrate product is about $1\times10^7$ CFU/g to about $1\times10^9$ CFU/g, and more preferably about $1\times10^8$ CFU/g. One pound of the concentrate or premix is then added to a finished ton of feed to provide $1.5\times10^5$ cfu/g of feed. A preferred dosage range for inclusion into water is about $1\times10^6$ CFU/g to about $1\times10^8$ CFU/g, and more preferably about $1\times10^7$ CFU/g. A preferred dosage range of the liquid drench and gel is about $1\times10^6$ CFU/g to about $1\times10^9$ CFU/g, and more preferably about $1\times10^8$ CFU/g.

While these above listed examples of the present invention disclose the use of freeze-dried Bacillus as an ingredient for the premix, concentrate, gel or water form, the present invention is not limited to use of freeze-drying Bacillus before administrating to poultry, and non-freeze dried Bacillus are considered well within the scope of the present invention. For example, spray-dried, fluidized bed dried, or solid-state fermentation or Bacillus in other states may be used in accordance with the present invention.

When fed to an animal, such as poultry, Bacillus become established within the animal's gastrointestinal tract. As a result of the Bacillus strains, 747, 1104, 1541, 1781, and 2018 of the present invention becoming established in the animal's gastrointestinal tract, a significant reduction in pathogen load for both C. perfringens and APEC may be obtained.

Also described herein is a method of reducing both C. perfringens and APEC pathogen load in broiler chickens by administering a DFM including one or more Bacillus strains, 1104, 1541, and 1781. In this method, samples of gastrointestinal tracts (GIT) of broiler chicken populations which had and had not been administered with a DFM including one or more Bacillus strains, 1104, 1541, and 1781 were sampled. According to this method portions of gastrointestinal tracts of broilers are obtained and E. coli colonies are counted and recorded. A selection of isolated E. coli colonies is made and the genomic DNA of the selected E. coli colonies is extracted. The DNA is amplified and APEC pathotype is determined using multiplex polymerase chain reaction (PCR). To verify that the E. coli is APEC, the PCR product is then run through capillary gel electrophoresis and each isolate is confirmed to contain at least two of the five following APEC-associated virulence genes in its genome: hlyF, ompT, iroN, iss, iutA. Similarly, portions of gastrointestinal tracts of broilers is obtained and C. perfringens colonies are counted and record. A selection of isolated C. perfringens colonies is made and the genomic DNA of the selected C. perfringens colonies is extracted. The C. perfringens DNA is amplified and C. perfringens toxinotype is determined using multiplex polymerase chain reaction (PCR) to amplify the alpha toxin gene. In order to eliminate the non-perfringens Clostridium species the PCR product is then run through capillary gel electrophoresis and each isolate is confirmed to be C. perfringens. According to this method, pathogen load for APEC in broilers treated with the DFM containing the Bacillus strains, 1104, 1541, and 1781, is on average $2.1\times10^4$ CFU/g as compared to untreated broilers, which yield an average APEC level of $2.1\times10^5$ CFU/g. Similarly, according to this method, pathogen load for C. perfringens in broilers treated with the DFM containing the Bacillus strains, 1104, 1541, and 1781, is on average 50 CFU/g as compared to untreated broilers, which yield an average C. perfringens level of $1.7\times10^2$ CFU/g.

Also described herein is a method of reducing both C. perfringens pathogen load in turkeys by administering a DFM including Bacillus strain 1104 in combination with commercially available strain Bs2084 (Microbial Discovery Group, Franlkin, Wis.). In this method, samples of gastrointestinal tracts (GIT) of turkey populations which had and had not been administered with a DFM including Bacillus strain 1104 in combination with commercially available strain Bs2084 (Microbial Discovery Group, Franlkin, Wis.) were collected. According to this method portions of gastrointestinal tracts of turkeys are obtained and C. perfringens colonies are counted and record. A selection of isolated C. perfringens colonies is made and the genomic DNA of the selected C. perfringens colonies is extracted. The C. perfringens DNA is amplified and C. perfringens toxinotype is determined using multiplex polymerase chain reaction (PCR) to amplify the alpha toxin gene. In order to eliminate the non-perfringens Clostridium species the PCR product is then run through capillary gel electrophoresis and each isolate is confirmed to be C. perfringens. According to this method, pathogen load for C. perfringens in turkeys treated with the DFM containing the including Bacillus strain 1104 in combination with commercially available strain Bs2084 (Microbial Discovery Group, Franlkin, Wis.) is on average 50 CFU/g as compared to untreated turkeys, which yield an average C. perfringens level of $1.7\times10^2$ CFU/g.

While these examples use freeze-dried *Bacillus* as an ingredient for the premix, concentrate, gel or water form, it is not necessary to freeze-dry the *Bacillus* before administrating to poultry. For example, spray-dried, fluidized bed dried, or solid-state fermentation or *Bacillus* in other states may be used.

EXAMPLES

The following Examples are provided for illustrative purpose only. The Examples are included herein solely to aid in a more complete understanding of the presently described invention. The Examples do not limit the scope of the invention described or claimed herein in any fashion.

Example 1

Isolation and Selection of *Bacillus* Strains 747, 1104, 1541, 1781 and 2018

Design. Select *Bacillus* isolates for their antimicrobial properties against avian pathogens *Clostridium perfringens* and avian pathogenic *Escherichia coli* (APEC) as candidate strains for use as a DFM to be applied in the poultry industry. Aerobic sporeforming bacteria were isolated from a variety of environmental sources and characterized using RAPD-PCR. Genetically-similar groups (184 representatives) were identified by sequencing the 16S rRNA gene and strains that were recognized to be non-GRAS species were eliminated. The remaining strains were then screened by exposing their cell-free bacteriocin to a genetically diverse panel of *C. perfringens* and APEC isolates to test for inhibition. After confirming the absence of the *Bacillus cereus* emetic toxin, the isolates with the greatest inhibition potential were selected to be commercialized.

Materials and Methods. Isolation of spore forming strains: 117 samples from various environmental sources were diluted with 99 mL of sterile 0.1% peptone broth and spore-treated in a 65° C. water bath for 30 min. Serial dilutions were made and pour-plated with tempered molten TSA (Becton, Dickenson & Company, Franklin Lakes, N.J.) and incubated at 32° C. for 12-24 h. Several isolated colonies from each sample were picked and struck to TSA plates for isolation and incubated at 32° C. for 12-24 h. Isolated colonies were picked and used to inoculate 3 mL TSB (Becton, Dickenson & Company, Franklin Lakes, N.J.) in a well of a 12-well culture plate (Falcon, Tewksbury, Mass.) and incubated at 32° C., shaking 100-125 rpm for 12-24 h. The growth culture was spun down and resuspended in 2 mL TSB with 20% glycerol. 1 mL of this mixture was frozen at −20° C. to be used for gDNA isolation, while the remaining 1 mL was frozen at −80° C. as frozen cell stock.

DNA Isolation: Genomic DNA was isolated from all 2029 isolated strains using either the Roche Applied Science High Pure PCR Template Kit or the following DNA isolation protocol: Add 20 μL of lysozyme (100 mg/mL) to 300 μL of overnight growth in TSB and incubate at 37° C. for 60 min, add 220 μL of lysis buffer (6 M Guanidine, 20% Triton-X 100, 10 mM Tris-HCl, pH 7.5) and incubate at 25° C. for 15 min, add 20 μl of Protease K 800 U/ml (NEB, Ipswich, Mass.) and incubate at 55° for 30 min, transfer 400 μL of lysate to a Wizard® SV 96 Binding Plate (Promega, Fitchburg, Wis.) and continue with manufacturer's filtration instructions from Wizard® SV 96 Genomic DNA Purification System starting from step 3.C.4 (4/15/revision) (Promega, Fitchburg, Wis.).

RAPD-PCR Profiles: All isolated strains were subjected to RAPD-PCR in order to generate strain-specific RAPD profiles. Each reaction contained 1 Ready-To-Go RAPD Analysis Bead (GE Healthcare, Chicago, Ill.), 2.5 μL RAPD primer 3 (5'-d{GTAGACCCGT}-3' (SEQ ID NO: 1), (Eurofins, Brussels, Belgium), 5 μL template gDNA and 17.5 μL nuclease-free water. Incubations were executed using an Applied Biosystems Veriti® Thermal Cycler (ThermoFisher Scientific, Milwaukee, Wis.) with the following protocol: 1 cycle at 95° C. for 5 minutes, 45 cycles of 95° C. for 1 minute, 36° C. for 1 minute, and 72° C. for 2 minutes. The PCR product was run through capillary gel electrophoresis using a Fragment Analyzer™ from Advance Analytical Technologies, Inc. and visualized on PROsize 2.0 (Advanced Analytical Technologies, Inc., Ames, Iowa). RAPD profiles were imported into BioNumerics (Applied Maths, Sint-Martens-Latem, Belgium) and a dendrogram was generated using Dice and the UPGMA algorithm method. Clusters were established using a 75% similarity cutoff and n representatives were chosen from each cluster where n=the square root of the number of cluster members.

16S rRNA Sequencing: 408 representative strains were subjected to 16 rRNA sequencing after amplification of the 16S rRNA gene using primers 27F-YM (5'-d{AGAGTTTGATYMTGGCTCAG}-3' (SEQ ID NO: 2), (Eurofins, Brussels, Belgium) and 1492R-Y (5'-d{TACCTTGTTAYGACTT}-3' (SEQ ID NO: 3), (Eurofins, Brussels, Belgium). Strains identified as GRAS *Bacillus* species allowed to proceed as candidate *Bacillus* strains.

Indicator Pathogens: APEC and *Clostridium perfringens* Type A isolates isolated from poultry were characterized based on a RAPD-PCR (RAPD primer 2 [5'-d{GTTTCGCTCC}-3' (SEQ ID NO: 4)]). Genetically-varied representative APEC and *C. perfringens* Type A isolates were selected as indicators strains for the bacteriocin assay.

Bacteriocin Assay: Bacteriocin from 171 candidate *Bacillus* strains was harvested from 3 mL of 18 h growth in TSB (30° C., shaking 100 rpm) and sterilized by filtration with a 0.22 μm filter (Merck Millipore, Billerica, Mass.). For *C. perfringens* assay: 70 μL of cell-free bacteriocin was added to 600 μL of indicator strain (1% inoculum) and incubated at 37° C., AnaeroPack System (Mitsubishi, New York, N.Y.), 12-18 h. Top performers were subjected to the APEC assay: 200 μL of cell-free bacteriocin was added to 466 μL of indicator strain (1% inoculum) or 70 μL of cell-free bacteriocin was added to 600 μL of indicator strain (1% inoculum) and incubated at 37° C., shaking 100 rpm, 12-18 h.

Emetic Toxin screening: The five best performers were screened for the Tecra™ *Bacillus cereus* emetic toxin using the (3M, Maplewood, Minn.) *Bacillus* Diarrhoeal Enterotoxin Visual Immunoassay kit.

Results and Discussion. 2029 aerobic sporeforming bacteria were isolated from 117 environmental samples of various sources. Each isolate was subjected to RAPD-PCR (RAPD primer 3) to produce strain-specific fingerprints and dendrogram was generated based on RAPD-type similarity. 408 isolates were selected as representatives of 184 clusters and identified by sequencing the 16S rRNA gene. Of these 171 isolates were identified as species on the GRAS list. Cell-free bacteriocin of these 171 isolates was collected and tested for inhibition against a genetically-varied panel of 15 *Clostridium perfringens* isolates and 16 APEC isolates. The top 5 performers were confirmed to be negative for the *Bacillus cereus* emetic toxin and chosen as strains for commercial scale-up. These 5 strains were 747, 1104, 1541, 1781, and 2018.

Example 2

Isolation and Selection of *Bacillus* Strain 1999

Introduction. A detailed analysis of *Bacillus* genomes indicated that gene clusters associated with production of antimicrobials were present in one or more strains, but absent in others. Genes for nonribosomal synthesized lipopeptides, cyclodepsipeptides, post-translationally modified peptides and polyketides were among those detected. None of the *Bacillus* strains, according to the present invention, contained the post-translationally modified peptide, plantazolocin, or the uncharacterized NRPS gene cluster, both present in the non-proprietary strain 2084. Primers were therefore developed to detect the nrsF gene of the NRPD gene cluster and to the ycaO gene of the plantazolicin operon.

Materials and Methods. PCR Amplification: Three primer sets were developed for the ycaO gene of the plantazolicin operon and 2 primer sets for the nrsF gene of the NRPD gene cluster as shown below in Table 1.

TABLE 1

Primers designed to detect the antimicrobial genes unique to *Bacillus* strain 2084 ("Forward Primers" disclolse as SEQ ID NOS 5-9 and "Reverse Primers" dislosed as SEQ ID NOS 10-14, all respectively, in order of appearance).

| Gene | Forward Primer Name | Forward Primer (5'-3') | Reverse Primer Name | Reverse Primer (5'-3') | Amplicon Size (bp) |
|---|---|---|---|---|---|
| 2084 ycaO | YcaO_F1 | ACCAACATCATT GCGGCTAC | YcaO_R1 | GACGATATCGG TTCCTGCGT | 292 |
| 2084 ycaO | YcaO_F2 | ACCTTTGTAGAA GCAGCAATTTCA | YcaO_R2 | CACATCAATCT GGGGCAAGC | 102 |
| 2084 ycaO | YcaO_F3 | TCATACGGAATG GCCTGGGG | YcaO_R3 | TCATATCAACTA AGTGTAGCCGCA | 248 |
| 2084 nrs | NrsF_F1 | ACTTTGTTGAA GTTGGCCCG | NrsF_R1 | AGACGTTACGT TTTCCCCCT | 123 |
| 2084 nrs | NrsF_F2 | ACAGTTGCTGTT AGTGTCCCA | NrsF_R2 | CGGGCCAACTT CAACAAAAG | 138 |

PCR reactions were set up in 20 μL volumes containing 2.0 μL 10×PCR Buffer, 0.6 50 μL mM MgCl$_2$, 0.4 μL dNTPs (10 mM each), 2.8 μL of each forward and reverse primer (10 μM each), 0.08 μL Platinum Taq (Life Technologies 10966083) and 9.32 μL ddH$_2$O. Conditions were optimized for the YcaO_F3/R3 and NrsF_F2/R2 primer sets and started with a 4 minute denaturation at 95° C. followed by 30 cycles of denaturation at 95° C. for 30 seconds, annealing at 60° C. for 30 seconds and extension at 72° C. for 30 seconds before a final extension at 72° C. for 7 minutes.

Bacteriocin Assay: *Bacillus* colonies were inoculated into 25 mL BHI in a 125 mL Erlenmeyer flask and incubated at 32° C. for 24 h with shaking (150 rpm). One mL was used to inoculate 100 mL BHI in a 500 mL Erlenmeyer flask and incubated at 32° C. for 24 h with shaking (150 rpm). The culture was split between two 50 mL conical tubes and centrifuged at 14,000×g for 20 min. The supernatant was then filtered through a 0.2 μm filter and stored at −20° C. before use.

The *E. coli* isolates were picked in to 10 mL of TSB and incubated at 37° C. for 24 h. 0.1 mL was then transferred to 10 mL TSB and incubated at 37° C. for 6 hours. Again, 0.1 mL of culture was used to inoculate 10 mL TSB and 600 μL was transferred into a 24 well culture plate with 70 μL of bacteriocin. The plates were incubated at 37° C., with shaking (150 rpm) for 16-20 h before ODs were taken to measure inhibition.

Results. Genetic screening for new proprietary candidate DFM strains: The inventor's library of over 2000 environmental spore-forming bacteria was screened using the primers developed to detect the nrsF gene of the NRPD gene cluster and to the ycaO gene of the plantazolicin operon. Eighteen strains were positive for both genes, nine for the ycaO gene only and two for the nrsF gene only. Sequencing of the 16S rRNA gene indicated that all 29 belonged to the *Bacillus subtilis* group.

Functional screening for new product development: Twelve of the 29 strains selected through genetic screening were tested in a bacteriocin assay to inhibit a panel of 12 *E. coli*. Three strains inhibited the panel of *E. coli* greater than 75%, two clustered with the commercial strains with average inhibitions ranging from 50 to 75% and the remaining seven inhibited the panel less than 50% as shown below in Table 2.

TABLE 2

Strains were selected based on the presence of one or both antimicrobial associated genes, nrsF and ycaO from 2084. A subset was screened for bacteriocin activity against a panel of 12 *E. coli* and were grouped according to inhibition.

| Strain | Lab# | nrsF | ycaO | Average Inhibition | 16S rRNA Sequence ID |
|---|---|---|---|---|---|
| 1999 | 11.10.14 | + | + | 89.4 | *Bacillus subtilis* group |
| 1145 | 6.5.14 | + | + | 78.1 | *Bacillus subtilis* group |
| 967 | 5.5.2 | + | + | 76.5 | *Bacillus subtilis* group |
| 2018 | Commercial | − | − | 61.6 | *Bacillus subtilis* group |
| 466 | 2.16.12 | − | + | 59.0 | *Bacillus subtilis* group |
| 2084 | Commercial | + | + | 55.8 | *Bacillus subtilis* group |
| 747 | Commercial | − | − | 54.4 | *Bacillus subtilis* group |
| 1382 | 8.5.2 | − | + | 53.2 | *Bacillus subtilis* group |
| 1192 | 6.9.7 | + | + | 48.3 | *Bacillus subtilis* group |
| 1161 | 6.7.5 | + | + | 47.5 | *Bacillus subtilis* group |
| 358 | 2.10.2 | − | + | 46.1 | *Bacillus subtilis* group |
| 1879 | 10.12.22 | + | − | 38.8 | *Bacillus subtilis* group |
| 1621 | 9.9.8 | − | + | 23.3 | *Bacillus subtilis* group |
| 1073 | 6.1.8 | + | + | 5.7 | *Bacillus subtilis* group |
| 1166 | 6.7.10 | + | + | 0.3 | *Bacillus subtilis* group |
| 1201 | 6.9.16 | + | + | Not Tested | *Bacillus subtilis* group |
| 1169 | 6.7.13 | + | + | Not Tested | *Bacillus subtilis* group |
| 1235 | 6.11.9 | + | + | Not Tested | *Bacillus subtilis* group |
| 1240 | 6.11.14 | + | + | Not Tested | *Bacillus subtilis* group |
| 1072 | 6.1.7 | + | + | Not Tested | *Bacillus subtilis* group |
| 1067 | 6.1.2 | + | + | Not Tested | *Bacillus subtilis* group |
| 996 | 5.5.31 | + | + | Not Tested | *Bacillus subtilis* group |
| 987 | 5.5.22 | + | + | Not Tested | *Bacillus subtilis* group |
| 839 | 5.1.34 | + | + | Not Tested | *Bacillus subtilis* group |
| 1952 | 11.7.9 | + | + | Not Tested | *Bacillus subtilis* group |
| 387 | 2.11.22 | − | + | Not Tested | *Bacillus subtilis* group |
| 363 | 2.10.7 | − | + | Not Tested | *Bacillus subtilis* group |
| 357 | 2.10.1 | − | + | Not Tested | *Bacillus subtilis* group |
| 1975 | 11.9.4 | − | + | Not Tested | *Bacillus subtilis* group |
| 1899 | 11.2.8 | − | + | Not Tested | *Bacillus subtilis* group |
| 1704 | 10.1.14 | + | − | Not Tested | *Bacillus subtilis* group |

The general success rate for selecting commercially viable strains from a library of environmental spore-forming bacteria is about 2%. With this genetic screening five of the 12 strains selected were the same or better than the existing commercialized strains i.e. a success rate of 42%.

Conclusions. Primers were developed to detect the nrsF gene of the NRPD gene cluster and to the ycaO gene of the plantazolicin operon, genes that were only present in the non-proprietary strain 2084. Using genetic screening twenty-nine strains were identified from a library of over 2000 environmental spore-forming bacteria for in vitro assays. Of twelve tested, five had similar or better activity profiles to current proprietary strains, i.e. a success rate of 42% compared to 2% without genetic preselection. *Bacillus* strain 1999 was selected for commercialization.

Example 3

The Inhibitory Effect of Bacteriocins from *Bacillus* Strains 747, 1104, 1541, 1781 and 2018 on the Growth of Avian Pathogenic *Escherichia coli* (APEC)

Introduction. Avian colibacillosis is a disease in chickens caused by avian pathogenic *Escherichia coli* (APEC). Controlling or reducing rates of colibacillosis in the commercial poultry industry can have a significant economic impact (Georgopoulou et al., 2005). Some strains of *Bacillus* have been shown to be effective in preventing and controlling disease in poultry (La Ragione et al., 2001; La Ragione and Woodward, 2003) This is likely in part due to antimicrobial compounds commonly produced and secreted by many *Bacillus* species such as bacteriocins (Tagg et al., 1976). Five *Bacillus* strains selected for their antimicrobial properties against *Clostridium perfringens* and APEC by the inventors. Cell-free bacteriocin was collected from DFM strains 747, 1104, 1541, 1781, and 2018 and were used in a bioassay to determine their inhibitory effect on the growth of a range of APEC strains isolated from commercial broiler gastrointestinal tracts. This study was conducted as an in vitro model in order to optimize DFM formulations for use in a commercial broiler complex.

Materials and Methods. APEC Isolates: 28 APEC isolates, harvested from broiler gastrointestinal tracts, were selected as representatives from a commercial broiler complex. Genomic DNA was extracted from each isolate using the following gDNA extraction method: Add 20 μL of lysozyme (100 mg/mL) to 500 μL of overnight growth in Tryptic Soy Broth (TSB; BD Difco) and incubate at 37° C. for 30 min, add 300 μL of lysis buffer (6 M Guanidine, 20% Triton-X 100, 10 mM Tris-HCl, pH 7.5) and incubate at 25° C. for 15 min, add 20 μl of Protease K 800 U/ml (NEB, Ipswich, Mass.) and incubate at 55° for 30 min, transfer 400 μL of lysate to a Wizard® SV 96 Binding Plate (Promega, Fitchburg, Wis.) and continue with manufacturer's filtration instructions from Wizard® SV 96 Genomic DNA Purification System starting from step 3.C.4 (4/15/revision) (Promega, Fitchburg, Wis.).

APEC pathotype was determined using multiplex polymerase chain reaction (mPCR). Each isolate was confirmed to contain at least two of the five following APEC-associated virulence genes in its genome: hlyF, ompT, iroN, iss, iutA. Each reaction mixture contained 4 mM magnesium chloride (Invitrogen, Carlsbad, Calif.), 0.25 mM deoxynucleoside triphosphates (Invitrogen, Carlsbad, Calif.), 0.25 μM each primer (Eurofins, Brussels, Belgium), and 1 U Platinum® Taq DNA Polymerase (Invitrogen, Carlsbad, Calif.) and 5 μL of template gDNA (Johnson et al., 2008). The reaction was run on an Applied Biosystems Veriti® Thermal Cycler (ThermoFisher Scientific, Milwaukee, Wis.) with the following protocol: 94° C. for 2 min; 25 cycles of 94° C. for 30 s, 63° C. for 30 s, 68° C. for 3 min; and a final cycle of 72° C. for 10 min. The PCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

The 28 APEC isolates used in this experiment were selected from a pool of 136 total APEC isolates harvested from broiler gastrointestinal tracts. The selected isolates were chosen as cluster representatives based on a RAPD-PCR (RAPD primer 2 [5'-d{GTTTCGCTCC}-3'] (SEQ ID NO: 4)) similarity dendrogram in order to include the broadest range of genetic variation between APEC isolates.

Bacteriocin: Each *Bacillus* strain (747, 1104, 1541, 1781, and 2018) was grown from −80° C. cell stock in 25 mL of TSB in a 125 mL Erlenmeyer flask and incubated at 32° C., shaking 150 rpm, for 24 h. 100 mL of TSB in a 500 mL Erlenmeyer flask was inoculated with 1 mL of the 24-hour growth culture and incubated 32° C., shaking 150 rpm, for 36 h. After incubation the growth culture was spun down at 14,000×g. The supernatant was filter sterilized using 0.20 μm, SFCA membrane Nalgene™ Rapid-Flow™ vacuum filters and the filtrate was frozen at −20° C.

Bioassay: The select APEC isolates were grown up from frozen stock by inoculating 10 mL tubes of TSB and incubating them at 37° C. overnight. The resulting culture (100 μL) was then used to inoculate 10 mL tubes of TSB which were incubated at 37° C. for 6 h to ensure growth-curve synchronicity. At the start of the assay, TSB tubes were inoculated with 100 μL of 6 hour growth and this inoculated media served as the indicator for the assay. Aliquots of bacteriocin from each *Bacillus* strain were thawed and gently mixed to guarantee homogeneity.

For every *Bacillus* strain, 70 μL of bacteriocin was dispensed into one well of a 48 well cell culture plate (Falcon, Tewksbury, Mass.) for each of the 28 APEC isolates. For every APEC isolate, 600 μL of indicator media as described above was added to the same wells containing *Bacillus* bacteriocin such that every APEC isolate was paired with every *Bacillus* strain. Positive control wells contained only 600 μL of indicator, while negative control wells contained 70 μL of bacteriocin and 600 μL of fresh TSB to confirm bacteriocin sterility. The plate was incubated at 37° C., shaking at 150 rpm for 12-18 h.

After incubation, the OD of each well was read on a Biotek Epoch Microplate Spectrophotometer at 600 nm wavelength. Results were expressed as percent inhibition of APEC by *Bacillus* by using the formula $$\left(1 - \frac{c}{x}\right) * 100,$$

where C=blanked positive APEC control OD, and X=blanked treatment OD.

Results. Percent inhibition of APEC isolates by bacteriocin from *Bacillus* strains 747, 1104, 1541, 1781, and 2018 are shown below in Table 3.

TABLE 3

Percent inhibition of APEC isolates by *Bacillus* strains 747, 1104, 1541, 1781, and 2018.

| APEC | 747 | 1104 | 1541 | 1781 | 2018 |
|---|---|---|---|---|---|
| E50.1.2.2 | 86.0 | 55.8 | 27.1 | 93.1 | 93.3 |
| E50.1.3.1 | 80.8 | 66.6 | 53.6 | 89.9 | 82.4 |
| E50.1.3.2 | 68.3 | 47.3 | 31.6 | 62.0 | 53.9 |
| E50.4.1.3 | 96.7 | 85.6 | 49.7 | 98.7 | 88.9 |
| E50.6.2.2 | 68.6 | 60.6 | 37.4 | 83.7 | 47.3 |

TABLE 3-continued

Percent inhibition of APEC isolates by Bacillus
strains 747, 1104, 1541, 1781, and 2018.

| APEC | 747 | 1104 | 1541 | 1781 | 2018 |
|---|---|---|---|---|---|
| E50.7.1.4 | 99.5 | 92.9 | 64.7 | 100.0 | 76.0 |
| E50.7.2.1 | 100.0 | 99.3 | 55.6 | 100.0 | 97.9 |
| E50.8.1.1 | 99.3 | 97.1 | 51.4 | 99.4 | 98.5 |
| E50.8.1.3 | 100.0 | 92.8 | 32.4 | 100.1 | 99.5 |
| E50.8.2.1 | 78.6 | 37.9 | 9.6 | 75.6 | 76.7 |
| E50.9.2.3 | 78.5 | 59.4 | 40.0 | 78.8 | 66.3 |
| E50.9.2.5 | 79.0 | 62.2 | 31.0 | 76.8 | 79.4 |
| E50.9.3.3 | 85.6 | 66.3 | 19.3 | 73.0 | 56.3 |
| E50.12.1.4 | 96.6 | 82.6 | 43.0 | 78.1 | 80.3 |
| E50.12.1.5 | 95.6 | 74.5 | 21.7 | 80.5 | 83.6 |
| E50.11.3.1 | 100.0 | 60.9 | 26.9 | 100.0 | 28.6 |
| E50.14.1.3 | 73.2 | 55.5 | 23.3 | 74.0 | 61.4 |
| E50.15.1.2 | 96.7 | 27.9 | 30.6 | 95.2 | 82.0 |
| E50.16.2.1 | 75.5 | 25.0 | 0.0 | 59.1 | 38.9 |
| E50.16.2.5 | 88.6 | 22.5 | 0.0 | 60.1 | 36.4 |
| E50.17.2.1 | 99.6 | 96.8 | 74.4 | 97.7 | 95.2 |
| E50.17.2.2 | 100.0 | 95.8 | 76.4 | 99.6 | 99.9 |
| E50.17.2.3 | 100.0 | 94.8 | 61.5 | 100.0 | 99.8 |
| E50.18.1.1 | 99.9 | 59.2 | 23.3 | 99.4 | 99.1 |
| E50.18.3.1 | 100.0 | 99.9 | 50.7 | 100.0 | 100.0 |
| E50.19.1.2 | 43.6 | 32.6 | 10.2 | 68.0 | 44.4 |
| E50.20.1.4 | 75.0 | 62.4 | 40.2 | 81.1 | 58.9 |
| E50.20.3.5 | 96.1 | 81.4 | 37.0 | 94.3 | 76.6 |
| AVERAGE | 87.9 | 67.7 | 36.5 | 86.4 | 75.0 |

All Bacillus strains showed inhibition of every APEC isolate except for 1541 which showed no inhibition of two APEC isolates. Bacillus strains 747 and 1781 exhibited the strongest overall inhibitory effect with an average of 88.0% and 86.4% inhibition, respectively, while 1541 presented the weakest inhibition with an average of 35.2%.

Discussion. These results show clear evidence of an in vitro inhibitory effect of avian pathogenic Escherichia coli by Bacillus strains 747, 1104, 1541, 1781, and 2018. They also provide evidence of a varied array of antimicrobial agents produced by each Bacillus strain as indicated by the non-uniform pattern of inhibition across the Bacillus strains. This suggests that implementation of multiple Bacillus strains in combination could capture a greater breadth of APEC genetic diversity and therefore be more effective in preventing and controlling colibacillosis, while at the same time avoiding selection of antimicrobial-resistant pathogens in a commercial poultry setting.

Example 4

The Inhibitory Effect of Bacteriocins from Bacillus Strains 747, 1104, 1541, 1781 and 2018 on the Growth of Clostridium perfringens Introduction. Clostridium perfringens causes infection in poultry known as Clostridium perfringens-associated necrotic enteritis (NE). The most widespread toxinotype causing NE in poultry is C. perfringens Type A, noted by its production of the C. perfringens alpha toxin (Songer, 1996). C. perfringens-associated NE can have a significant impact on commercial poultry operations as it increases mortality and decreases weight gain of chickens and turkeys, therefore controlling or reducing rates of NE in the commercial poultry industry is highly desirable (Heier et al., 2001; Lovland et al., 2003, 2004). Some strains of Bacillus have been shown to be effective in preventing and controlling disease in poultry (La Ragione et al., 2001). This is likely in part due to antimicrobial compounds commonly produced and secreted by many Bacillus species such as bacteriocins (Tagg et al., 1976). Five Bacillus strains selected for their antimicrobial properties against Clostridium perfringens and avian pathogenic E. coli (APEC) were isolated by the inventors. Cell-free bacteriocin was collected from DFM strains 747, 1104, 1541, 1781, and 2018 and were used in a bioassay to determine their inhibitory effect on the growth of a range of C. perfringens Type A strains isolated from commercial broiler gastrointestinal tracts. This study was conducted as an in vitro model in order to optimize DFM formulations for use in a commercial broiler complex.

Materials and Methods. C. perfringens Type A Isolates: 18 C. perfringens Type A isolates, harvested from broiler gastrointestinal tracts, were selected as representatives from a commercial broiler complex. Genomic DNA was extracted from each isolate using the Roche Applied Science High Pure PCR Template Kit. C. perfringens toxinotype was determined using polymerase chain reaction (PCR) to amplify the alpha toxin gene. Each reaction mixture contained 2.5 µL 10×PCR buffer (Invitrogen, Carlsbad, Calif.), 1.6 µL magnesium chloride (Invitrogen, Carlsbad, Calif.), 0.5 µL deoxynucleoside triphosphates (Invitrogen, Carlsbad, Calif.), 100 pmol primers (Eurofins, Brussels, Belgium), and 1 U Platinum® Taq DNA Polymerase (Invitrogen, Carlsbad, Calif.) and 2 µL of template gDNA, 7.8 µL of ddH$_2$O (Yoo et al., 1997). The reaction was run on an Applied Biosystems Veriti® Thermal Cycler (ThermoFisher Scientific, Milwaukee, Wis.) with the following protocol: 5 min at 94° C., followed by 30 incubation cycles consisting of 1 min at 55° C., 1 min at 72° C., and 1 min at 94° C. The PCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

The 18 C. perfringens Type A isolates used in this experiment were selected from a pool of 26 total C. perfringens Type A isolates harvested from broiler gastrointestinal tracts. The selected isolates were chosen as cluster representatives based on a RAPD-PCR (RAPD primer 2 [5'-d{GTTTCGCTCC}-3'] (SEQ ID NO: 4)) similarity dendrogram in order to include the broadest ranges of genetic variation between C. perfringens Type A isolates.

Bacteriocin. Each Bacillus strain (747, 1104, 1541, 1781, and 2018) was grown from −80° C. cell stock in 25 mL of TSB in a 125 mL Erlenmeyer flask and incubated at 32° C., shaking 150 rpm, for 24 h. 100 mL of TSB in a 500 mL Erlenmeyer flask was inoculated with 1 mL of the 24 hour growth culture and incubated 32° C., shaking 150 rpm, for 36 h. After incubation the growth culture was spun down at 14,000×g. The supernatant was filter sterilized using 0.20 µm, SFCA membrane Nalgene™ Rapid-Flow™ vacuum filters and the filtrate was frozen at −20° C.

Bioassay. The select C. perfringens Type A isolates were grown up from frozen stock by inoculating 10 mL tubes of RCM broth (Becton, Dickinson & Company) and incubating them at 37° C. overnight. The resulting culture (100 µL) was then used to inoculate 10 mL tubes of RCM which were incubated at 37° C. for 6 h to ensure growth-curve synchronicity. At the start of the assay, RCM tubes were inoculated with 100 µL of 6 hour growth and this inoculated media served as the indicator for the assay. Aliquots of bacteriocin from each Bacillus strain were thawed and gently mixed to guarantee homogeneity.

For every Bacillus strain, 70 µL of bacteriocin from each Bacillus strain was dispensed into one well of a 48 well cell culture plate (Falcon, Tewksbury, Mass.) for each of the 18 C. perfringens Type A isolates. 600 µL of indicator media (1% inoculum in RCM) from each C. perfringens Type A isolate was added to the same wells containing *Bacillus* bacteriocin such that every *C. perfringens* Type A isolate was paired up with every *Bacillus* strain. Positive control wells contained only 600 μL of indicator, while negative control wells contained 70 μL of bacteriocin and 600 μL of un-inoculated RCM broth to confirm bacteriocin sterility. The plate was incubated at 37° C., anaerobically (Mitsubishi AnaeroPack System) for 12-18 h.

After incubation, the OD of each well was read on a Biotek Epoch Microplate Spectrophotometer at 600 nm wavelength. Results were expressed as percent inhibition of indicator isolate by *Bacillus* by using the formula $$\left(1 - \frac{c}{x}\right) * 100$$

where C=blanked positive indicator control OD, and X=blanked treatment OD.

Results. Percent inhibition of *C. perfringens* Type A isolates by bacteriocin from *Bacillus* strains 747, 1104, 1541, 1781, and 2018 are shown below in Table 4.

TABLE 4

Percent inhibition of *Clostridium perfringens* Type A by *Bacillus* strains 747, 1104, 1541, 1781, and 2018

| C. perfringens Type A Isolate | 747 (%) | 1104 (%) | 1541 (%) | 1781 (%) | 2018 (%) |
| --- | --- | --- | --- | --- | --- |
| C50.18.2.1 | 98.7 | 98.5 | 98.6 | 98.9 | 98.2 |
| C50.20.3.1 | 98.7 | 98.6 | 98.7 | 98.8 | 98.7 |
| C50.20.3.2 | 98.7 | 98.5 | 98.7 | 98.8 | 98.6 |
| C50.20.3.3 | 98.7 | 98.7 | 98.9 | 99.0 | 98.9 |
| C50.20.3.4 | 98.8 | 98.7 | 98.7 | 99.1 | 98.8 |
| C50.20.3.5 | 88.3 | 4.9 | 7.6 | 10.1 | 11.2 |
| C50.22.2.1 | 98.3 | 98.3 | 98.3 | 98.4 | 98.6 |
| C50.23.2.1 | 97.7 | 97.8 | 97.1 | 97.8 | 98.0 |
| C50.23.2.2 | 95.6 | 95.0 | 95.0 | 95.3 | 95.5 |
| C50.23.2.3 | 98.3 | 98.4 | 98.5 | 98.5 | 98.6 |
| C50.23.2.4 | 95.2 | 94.4 | 94.8 | 94.9 | 95.0 |
| C50.23.2.5 | 96.0 | 95.6 | 95.4 | 95.3 | 95.9 |
| C50.24.2.1 | 95.1 | 94.2 | 94.4 | 94.1 | 94.2 |
| C50.26.2.1 | 98.3 | 98.4 | 98.4 | 98.3 | 98.5 |
| C50.26.2.2 | 95.5 | 94.7 | 95.3 | 95.0 | 95.4 |
| C50.26.2.3 | 98.4 | 98.3 | 96.3 | 98.7 | 98.7 |
| C50.26.2.5 | 98.2 | 98.5 | 94.7 | 98.4 | 98.4 |
| C50.26.3.2 | 98.4 | 98.0 | 97.9 | 98.2 | 97.6 |
| Average | 97.1 | 92.2 | 92.1 | 92.6 | 92.7 |

All *Bacillus* strains showed significant inhibition (>85%) of each *C. perfringens* Type A isolate with the exception of *C. perfringens* Type A isolate C50.20.3.5 which was only significantly inhibited by *Bacillus* strain 747. The highest average inhibition was by *Bacillus* strain 747 with 97.1% and a range of 95.2% to 98.8%, while *Bacillus* strain 1541 exhibited the lowest average inhibition with 92.1% and a range of 7.6% to 98.9%. Strain 1104 showed an average of 92.2% inhibition with a range of 4.9% to 98.7%, strain 1781 averaged 92.6% inhibition with a range of 10.1% to 99.1%, and strain 2018 showed an average inhibition of 92.7% with a range of 11.2% to 98.9%.

Discussion. These results show clear evidence of an in vitro inhibitory effect of *C. perfringens* by *Bacillus* strains 747, 1104, 1541, 1781, and 2018. They also provide evidence of a varied array of antimicrobial agents produced by each *Bacillus* strain as indicated by the non-uniform pattern of *C. perfringens* inhibition across the *Bacillus* strains. This suggests that implementation of multiple *Bacillus* strains in combination could capture a greater breadth of *C. perfringens* genetic diversity and therefore be more effective in preventing and controlling *C. perfringens*-associated diseases while at the same time avoiding selection of antimicrobial-resistant pathogens in a commercial poultry setting.

Example 5

The Effect of the *Bacillus* Direct Fed Microbial Product, According to One Embodiment of the Present Invention, on the Gastrointestinal Pathogen Load of Broilers Introduction. The gastrointestinal-associated pathogens *Clostridium perfringens* and avian pathogenic *Escherichia coli* (APEC) can have significant negative ramifications on the productivity of commercial broiler operations (Georgopoulou et al., 2005). *C. perfringens* strains that produce alpha toxin are categorized as the *C. perfringens* Type A toxinotype and cause necrotic enteritis in poultry which increases mortality and reduces weight gain (Immerseel et al., 2004). APEC is a causative agent for colibacillosis in birds in the form of airsacculitis, cellulitis, pericarditis, or perihepatitis (Barnes H J et al., 2008). Colibacillosis infections are of considerable concern for the poultry industry as they are the responsible for high rates of bird death and are the most reported reason for processing rejection (Yogaratnam, 1995). Controlling or reducing rates of NE and colibacillosis in the commercial broiler industry can increase efficiency and productivity which may bare substantial economic impacts for poultry growers. Some strains of *Bacillus* have been shown to be effective in preventing and controlling disease in poultry (La Ragione and Woodward, 2003; La Ragione et al., 2001). This is likely in part due to antimicrobial compounds commonly produced and secreted by many *Bacillus* species such as bacteriocins (Tagg et al., 1976). Five *Bacillus* strains selected for their antimicrobial properties against *Clostridium perfringens* and avian pathogenic *E. coli* (APEC) were isolated by the inventors. These five *Bacillus* strains were commercialized for use as DFM in poultry feed. By surveying pathogens in the gastrointestinal tracts of broilers from a commercial complex before and after treatment with the *Bacillus* DFM product, according to one embodiment of the present invention, a significant reduction in pathogen load for both *C. perfringens* and APEC was detected.

Design. Gastrointestinal tracts (GIT) from broiler chickens were sampled from a variety of houses within a commercial broiler complex before and after implementation of the *Bacillus* DFM product, according to one embodiment of the present invention. Sampling 1 consisted of 22 GITs (average age 22 d) before product, while sampling 2 had 24 GITs (average age 25 d) on treated feed.

Materials and Methods. Direct fed microbial: Treated birds were given feed supplemented with a formulation of *Bacillus* strains 1104 (40%), 1541 (20%) and 1781 (40%) at a final concentration of $1.5 \times 10^5$ CFU/g in finished feed.

Processing of Gastrointestinal Tracts: Selected broilers were sacrificed and the gastrointestinal tracts from the duodenal loop to the cloaca were removed and transported in sterile Whirl-pak® bags on ice. Upon arrival, 10 cm sections of the duodenum, jejunum, and ilium were rinsed with ~5 mL sterile 0.1% peptone broth, cut longitudinally, and combined in a sterile, filtered whirl-pak bag. 99 mL of sterile 0.1% peptone was added to the bag then the sections were masticated at 300 rpm, for 1 min. Serial dilutions were made and pour plated in duplicate with both CHROMagar™

ECC to enumerate *E. coli*, and *perfringens* TSC agar base (Oxoid™) with D-cycloserine (Sigma, 400 mg/L) for *Clostridium* enumeration.

APEC Screening: Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company, Franklin Lakes, N.J.) if possible. Genomic DNA was extracted from each isolate using the following gDNA extraction method: Add 20 µL of lysozyme (100 mg/mL) to 500 µL of overnight growth in TSB and incubate at 37° C. for 30 min, add 300 µL of lysis buffer (6 M Guanidine, 20% Triton-X 100, 10 mM Tris-HCl, pH 7.5) and incubate at 25° C. for 15 min, add 20 µl of Protease K 800 U/ml (NEB, Ipswich, Mass.) and incubate at 55° for 30 min, transfer 400 µL of lysate to a Wizard® SV 96 Binding Plate (Promega, Fitchburg, Wis.) and continue with manufacturer's filtration instructions from Wizard® SV 96 Genomic DNA Purification System starting from step 3.C.4 (4/15/revision) (Promega, Fitchburg, Wis.).

APEC pathotype was determined using multiplex polymerase chain reaction (mPCR). In order to be considered APEC, an *E. coli* isolate had to contain at least two of the five following APEC-associated virulence genes in its genome: hlyF, ompT, iroN, iss, iutA. Each reaction mixture contained 4 mM magnesium chloride (Invitrogen, Carlsbad, Calif.), 0.25 mM deoxynucleoside triphosphates (Invitrogen, Carlsbad, Calif.), 0.25 µM each primer (Eurofins, Brussels, Belgium), and 1 U Platinum® Taq DNA Polymerase (Invitrogen, Carlsbad, Calif.) and 5 µL of template gDNA (Johnson et al., 2008). The reaction was run on an Applied Biosystems Veriti® Thermal Cycler (ThermoFisher Scientific, Milwaukee, Wis.) with the following protocol: 94° C. for 2 min; 25 cycles of 94° C. for 30 s, 63° C. for 30 s, 68° C. for 3 min; and an extension cycle of 72° C. for 10 min. The mPCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

*C. perfringens* Type A Screening: Presumptive *C. perfringens* isolates appear black on *perfringens* TSC agar base. All black colonies were counted and recorded as presumptive *C. perfringens* CFU/g counts. Five isolated black colonies from each bird were picked and grown in RCM broth (Oxoid™) if possible. Genomic DNA was extracted from each isolate using the Roche Applied Science High Pure PCR Template Kit.

*C. perfringens* toxinotype was determined using polymerase chain reaction (PCR) to amplify the alpha toxin gene. In order for an isolate to be considered *Clostridium perfringens* Type A it had to contain the alpha toxin gene, otherwise it was categorized as a non-*perfringens Clostridium*. Each reaction mixture contained 2.5 μL 10×PCR buffer (Invitrogen, Carlsbad, Calif.), 1.6 μL magnesium chloride (Invitrogen, Carlsbad, Calif.), 0.5 μL deoxynucleoside triphosphates (Invitrogen, Carlsbad, Calif.), 100 pmol primers (Eurofins, Brussels, Belgium), and 1 U Platinum® Taq DNA Polymerase (Invitrogen, Carlsbad, Calif.), 2 μL of template gDNA, and 7.8 μL of $ddH_2O$ (Yoo et al., 1997). The reaction was run on an Applied Biosystems Veriti® Thermal Cycler (ThermoFisher Scientific, Milwaukee, Wis.) with the following protocol: 5 min at 94° C., followed by 30 incubation cycles consisting of 1 min at 55° C., 1 min at 72° C., and 1 min at 94° C. The PCR product was then run through capillary gel electrophoresis using a Fragment Analyzer™ from Advance Analytical Technologies, Inc. and visualized on PROsize 2.0 (Advance Analytical Technologies, Inc).

Counts and Statistics: Pathotype levels for each bird were determined by multiplying the weight-adjusted presumptive CFU/g counts by the percent of presumptive isolates from each bird that were revealed to be pathogenic (*C. perfringens* or APEC). Birds that did not produce any detectable colonies on agar plates or birds that did not produce any confirmed pathogens through screening were assigned a value of <500 CFU/g for APEC and <50 CFU/g for *Clostridium perfringens* (for calculations this value was entered as 500 CFU/g and 50 CFU/g, respectively).

Statistical analysis for the comparison of untreated vs treated birds was run using an unpaired two-tailed t-test. Significant difference threshold was set at $P<0.05$.

Results. The pathogen counts represented in CFU/g of tissue are shown in FIGS. 1 and 2. Birds on treated feed exhibited a significant APEC reduction with an average APEC level of $2.1\times10^4$ CFU/g compared to birds on untreated feed which yielded an average APEC level of $2.1\times10^5$ CFU/g. APEC levels of untreated birds ranged from $5.0\times10^3$ to $2.2\times10^6$ CFU/g while treated birds ranged from $5.0\times10^3$ to $6.6\times10^5$ CFU/g.

*Clostridium perfringens* levels of birds fed untreated feed showed an average level of $1.7\times10^2$ CFU/g. Levels from treated birds, by comparison, were below detectable limits for all birds, therefore average level of *C. perfringens* for treated birds was calculated as 50 CFU/g.

Discussion. These data demonstrate significant reduction of APEC and *Clostridium perfringens* levels in broilers GITs fed the *Bacillus* DFM product, according to one embodiment of the present invention. Reduction of these pathogens can diminish cases of disease in broilers such as avian colibacillosis and necrotic enteritis, diseases which present significant financial liability to the poultry industry. Our research shows that including the *Bacillus* DFM product, according to one embodiment of the present invention, in feed is effective in reducing APEC and *C. perfringens* prevalence in broilers, therefore decreasing the disease-burden in commercial broiler operations.

Example 6

The Effect of the *Bacillus* DFM Product, According to One Embodiment of the Present Invention, on the Gastrointestinal Pathogen Load of Turkeys Introduction. The gastrointestinal-associated pathogen *Clostridium perfringens* can have significant negative ramifications on the productivity of commercial poultry operations. *C. perfringens* strains that produce alpha toxin are categorized as the *C. perfringens* Type A toxinotype and cause necrotic enteritis in poultry which increases mortality and reduces weight gain (Lovland et al., 2004) Thus, controlling or reducing rates of NE in the commercial turkey industry can increase efficiency and productivity which may bare substantial financial impacts to turkey growers. Some strains of *Bacillus* have been shown to be effective in preventing and controlling disease in poultry (La Ragione et al., 2001; La Ragione and Woodward, 2003). This is likely in part due to antimicrobial compounds commonly produced and secreted by many *Bacillus* species such as bacteriocins (Tagg et al., 1976). Five *Bacillus* strains selected for their antimicrobial properties against *Clostridium perfringens* and avian pathogenic *E. coli* (APEC) were isolated by the inventors. These five *Bacillus* strains (747, 1104, 1541, 1781, and 2018) were commercialized for use as DFM in poultry feed. By surveying pathogens in the gastrointestinal tracts of turkeys from a commercial complex before and after treatment with the *Bacillus* DFM product, according to one embodiment of the present invention, a significant reduction in *C. perfringens* pathogen load was detected.

Design. Turkey gastrointestinal tracts (GIT) were sampled from a variety of houses within a commercial turkey complex before and after implementation of the *Bacillus* DFM product, according to one embodiment of the present invention. Sampling 1 consisted of 18 GITs (average age 60 d) before product, while sampling 2 had 24 GITs (average age 34 d) on treated feed. Birds taken on sampling 2 were treated with a formulation of the *Bacillus* DFM product, according to one embodiment of the present invention.

Materials and Methods. Direct fed microbial: Treated birds were given feed supplemented with a formulation of the *Bacillus* strain 1104 (50%) identified herein and commercially available strain Bs2084 (Microbial Discovery Group, Franlkin, Wis.) at a final concentration of $1.5\times10^5$ CFU/g of finished feed.

Processing of Gastrointestinal Tracts: Selected turkeys were sacrificed and the gastrointestinal tracts from the duodenal loop to the cloaca were removed and delivered in sterile Whirl-pak® bags on ice. Upon arrival, 10 cm sections of the duodenum, jejunum, and ilium were rinsed with ~5 mL sterile 0.1% peptone broth, cut longitudinally, and combined in a sterile, filtered whirl-pak bag. 99 mL of sterile 0.1% peptone was added to the bag then the sections were masticatedat 300 rmp, for 1 min. Samples were heat shocked at 60° C. for 30 min then serial dilutions were made and pour-plated in duplicate with *perfringens* TSC agar base (Oxoid™) with D-cycloserine (Sigma, 400 mg/L) for *Clostridium* enumeration.

*C. perfringens* Type A Screening: Presumptive *C. perfringens* isolates appear black on *perfringens* TSC agar base. All black colonies were counted and recorded as presumptive *C. perfringens* CFU/g counts. Five isolated black colonies from each bird were picked and grown in RCM broth (Oxoid™) if possible. Genomic DNA was extracted from each isolate using the Roche Applied Science High Pure PCR Template Kit.

*C. perfringens* toxinotype was determined using polymerase chain reaction (PCR) to amplify the *C. perfringens* alpha toxin gene. In order for an isolate to be considered *Clostridium perfringens* Type A it had to contain the alpha toxin gene, otherwise it was categorized as a non-*perfringens Clostridium*. Each reaction mixture contained 2.5 μL 10×PCR buffer (Invitrogen, Carlsbad, Calif.), 1.6 μL magnesium chloride (Invitrogen, Carlsbad, Calif.), 0.5 μL deoxynucleoside triphosphates (Invitrogen, Carlsbad, Calif.), 100 pmol primers (Eurofins, Brussels, Belgium), and 1 U Platinum® Taq DNA Polymerase (Invitrogen, Carlsbad, Calif.) and 2 μL of template gDNA, 7.8 μL of dd$H_2O$ (Yoo et al., 1997). The reaction was run on an Applied Biosystems Veriti® Thermal Cycler (ThermoFisher Scientific, Milwaukee, Wis.) with the following protocol: 5 min at 94° C., followed by 30 incubation cycles consisting of 1 min at 55° C., 1 min at 72° C., and 1 min at 94° C. before a final extension at 72° C. for 7 minutes. The PCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

Counts and Statistics: Pathotype levels for each bird were determined by multiplying the weight-adjusted presumptive *C. perfringens* Type A CFU/g counts by the percent of presumptive isolates from each bird that were revealed to possess the *C. perfringens* alpha toxin. Birds that did not produce any detectable colonies on agar plates or birds that did not produce any confirmed alpha-toxin-producing isolates through screening were assigned a value of <50 CFU/g (for calculations this value was entered as 50 CFU/g).

Statistical analysis for the comparison of untreated vs treated birds was run using an unpaired two-tailed t-test. Significant difference threshold was set at $P<0.05$.

Results. *Clostridium perfringens* counts represented in CFU/g of tissue are shown in FIG. 3. *Clostridium perfringens* levels of birds fed untreated feed showed an average level of $1.7\times10^2$ CFU/g with a range of 50 to $5.5\times10^4$ CFU/g. Levels from treated birds, by comparison, were below detectable limits for all birds, therefore average level of *C. perfringens* for treated birds was calculated as 50 CFU/g.

Discussion. These data demonstrate a significant reduction of *Clostridium perfringens* levels in turkeys GITs fed the *Bacillus* DFM product, according to one embodiment of the present invention. Reduction of this pathogen can diminish cases of necrotic enteritis in turkeys, a disease which presents a significant financial liability for the poultry industry. Our research shows that including the *Bacillus* DFM product, according to one embodiment of the present invention, in feed is effective in reducing *C. perfringens* prevalence in turkeys, therefore decreasing the disease-burden in commercial broiler operations.

Example 7

Comparison of Poultry *Bacillus* Genomes

Introduction. Many bacteria produce compounds that can inhibit other bacteria, commonly known as bacteriocins. The function of bacteriocins is to allow the producer cells to compete with other microbes in their natural environment. They generally increase membrane permeability by forming pores in membranes of target cells or inhibit cell wall synthesis thereby preventing growth of susceptible microbes. *Bacillus* species produce multiple compounds with inhibitory activity against other microbes with many strains containing more than ten operons producing antifungal and antibacterial compounds. These compounds may have other functions within the cell. For example, surfactin is involved in intercellular signaling and biofilm formation (Zeriouh et al., 2014) and bacillibactin, is an iron-scavenger for *Bacillus* species, which then deprives other organisms of essential iron and inhibits their growth (Li et al., 2014).

The predominant bacteriocins produced by bacilli are a variety of functionally and structurally diverse peptides. They are often hydrophobic and cyclic with unusual amino acids and resistant to peptidases and proteases. They may be synthesized ribosomally or nonribosomally by multi-enzyme complexes, often followed by post-translational modifications.

A major group of ribosomally synthesized antimicrobial peptides are the lantibiotics, which contain the non-protein amino acid lanthionine, formed post-translationally. Type A lantibiotics have a linear secondary structure while Type B are more globular.

*Bacillus* strains often produce nonribosomally synthesized lipopeptides, fatty acids attached to small cyclic peptides. These nonribosomally synthesized peptides are structurally diverse (Luo et al., 2015a), as they are assembled from a heterogeneous group of precursors, but their synthesis by a multicarrier thiotemplate mechanism is conserved (Luo et al., 2015b). Nonribosomal peptide synthetases (NRPS) require posttranslational modification to be functionally active.

Other non-peptide antimicrobials are also produced by bacilli such as polyketides and siderophores. Polyketides are secondary metabolites which are also synthesized on multienzymes similar to NRPS and they also undergo posttranslational modification. Hybrid synthetases containing peptide, fatty acid and polyketide synthetase domains are also being identified in bacilli and some of these compounds were shown to have functional antimicrobial activity.

Most of the information available on the secondary compounds produced by bacilli and their antimicrobial activity (Chowdhury et al., 2015; Koumoutsi et al., 2004) is based on studies on plant-growth promoting rhizobacteria (PGPR) that are applied as spore formulations to improve crop production by promoting growth and inhibiting plant pathogens (Wu et al., 2015). A better understanding of how an organism lives and competes in its environment can be obtained by sequencing their full genome. Since 1995, when the first complete genome sequence of the bacteria *Haemophilus influenzae* Rd KW20 was published (Fleischmann et al., 1995), sequencing of genomes has increased exponentially and powerful databases and bioinformatics programs have been developed in order to predict the functions of newly sequenced organisms. Gene function is predicted based on the genetic organization of surrounding genes, conserved protein domains within genes and alignment with genes of established function. Predicted gene functions should then be confirmed by further molecular and biochemical experiments. A number of genome sequences of PGPR are available (Chen et al., 2007; Jeong et al., 2015) and the core genome and conserved antimicrobial loci have been identified (Fan et al., 2015). Comparative analysis of the draft genomes of the *Bacillus* strains identified herein (747, 1104, 1541, 1781, 1999, and 2018) to genomes available in the databases allowed the inventors to predict the types of antimicrobial compounds produced by the strains and determine differences between strains.

Methods. Draft genomes were obtained for six *Bacillus* strains identified herein (747, 1104, 1541, 1781, 1999, and 2018) and six previously known strains of bacilli (Baltzley et al., 2010) by assembling paired-end Illumina reads of genomic DNA. Shotgun genomic libraries were prepared with the library construction kit from Kapa Biosystems with an average gDNA fragment size of 435 bp (320-600 bp). The library pool was sequenced on one MiSeq flowcell for 261 cycles generating 261 nt reads using a MiSeq sequencing kit v2 (Illumina, San Diego, Calif.). Paired reads were merged to generate longer single reads with PEAR 0.9.6 (Zhang et al., 2014). High quality reads that passed data preprocessing steps were assembled with SPAdes 3.5.0 assembler (Nurk et al., 2013). The assembled scaffolds ranged from 18 to 51 contigs and were annotated using the prokka 1.11 annotation pipeline (Seemann, 2014). The draft genomes were between 3.91 and 4.15 Mb in size with 3894 to 4212 predicted genes as shown below is Table 5.

The contigs of each draft genome were aligned and ordered with Mauve genome alignment software (Darling et al., 2010) against a fully sequenced genome and then concatenated with a 100 Ns demarcating the contig boundaries. The concatenated draft genomes were compared using various tools in Geneious 8.1.7 (Kearse et al., 2012), EDGAR 2.0 (Blom et al., 2016) and PATRIC (Wattam et al., 2014).

Figure 4:
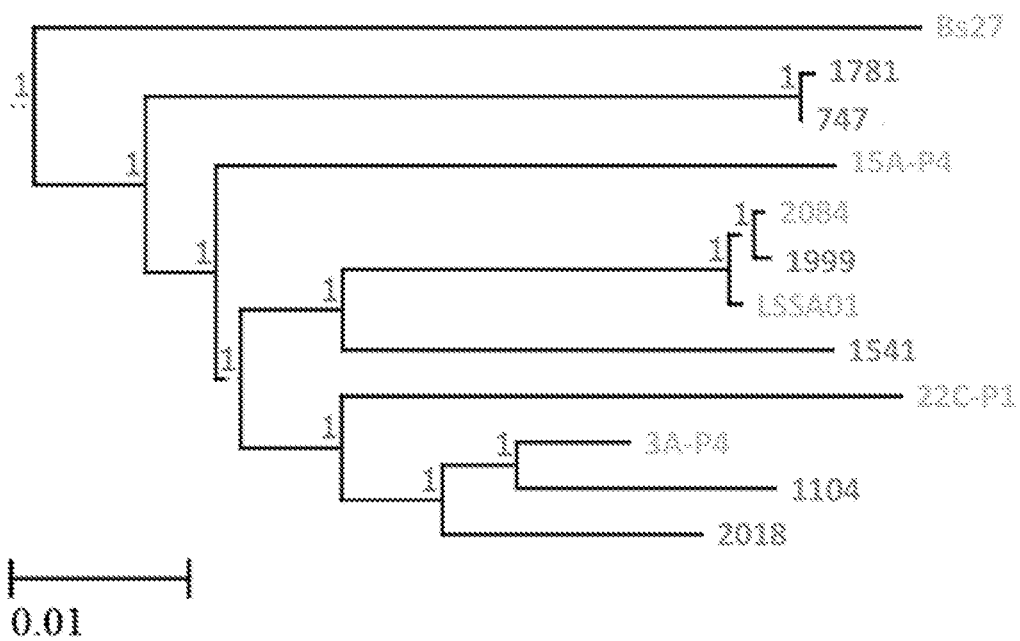
FIG. 4. Whole genome phylogenetic tree indicating the relatedness of strains to each other. *Bacillus* strains according to the present invention are identified in dark gray and previously identified strains are identified in light gray.

Results. Referring now to FIG. 4, a phylogenetic tree based upon similarities and differences in the draft genomes was created by MAUVE alignment, which indicates the relatedness of each of the strains to the others, is provided. This tree indicates that the strains 747 and 1781 are closely related, as are 1999, 2084 and LSSA01.

EDGAR Venn diagrams were created to identify unique genes in five of the *Bacillus* identified herein compared to the previously known strains. As only five strains can be compared in a Venn diagram previously known strain Bs27 was not included as it is the most different to any of the strains and previously known strain LSSA01 was not included as it is genetically similar to 2084. The majority of the genes identified as being unique to the strains were annotated as hypothetical i.e. there is no predicted function associated with the genes as shown below in Table 6. Many of these genes were clustered together in the genome indicating that they are likely part of a metabolic pathway.

TABLE 6

Genes that are present only in the *Bacillus* strains, according to the present, compared to the prior strains 3A-P4, 15A-P4, 2084 and 22C-P1. The majority of the unique genes are annotated as hypothetical, some of which are associated in clusters that likely represent unique metabolic pathways.

| Strain | 747 | 1104 | 1541 | 1781 | 2018 |
|---|---|---|---|---|---|
| Unique genes | 188 | 92 | 113 | 188 | 40 |
| Hypothetical genes | 135 | 63 | 71 | 135 | 22 |
| Unique gene clusters | 28 | 16 | 18 | 28 | 8 |

A detailed analysis of all twelve genomes indicated that gene clusters for a number of antimicrobial secondary metabolites were present in one or more strains, but absent in others as shown below in Table 7.

TABLE 5

General characteristics of the draft genomes obtained for the *Bacillus* strains

| | *Bacillus* Strains according to one embodiment of the present invention | | | | | | Prior Known *Bacillus* Strains | | | | | |
|---|---|---|---|---|---|---|---|---|---|---|---|---|
| | 747 | 1104 | 1541 | 1781 | 1999 | 2018 | 15A-P4 | 2084 | 22C-P1 | 3A-P4 | LSSA01 | Bs27 |
| Size (Mb) | 4.04 | 4.11 | 3.91 | 4.05 | 3.92 | 3.96 | 4.15 | 3.92 | 4.09 | 3.93 | 4.05 | 3.92 |
| Number of Contigs | 38 | 42 | 32 | 36 | 32 | 41 | 38 | 46 | 51 | 39 | 51 | 18 |
| % GC | 46.2 | 46.1 | 46.4 | 46.2 | 46.5 | 46.5 | 45.9 | 46.5 | 46.3 | 46.5 | 46.4 | 45.8 |
| Annotated Genes | 4065 | 4180 | 3894 | 4066 | 3953 | 3894 | 4212 | 3933 | 4141 | 3927 | 3949 | 4155 |
| Protein-coding genes | 3920 | 4028 | 3748 | 3920 | 3775 | 3748 | 4052 | 3776 | 4003 | 3780 | 3778 | 3995 |
| Genes with predicted functions | 2986 | 3068 | 2938 | 2987 | 2971 | 2938 | 3044 | 2971 | 3064 | 2982 | 2968 | 2981 |
| Hypothetical genes | 934 | 960 | 810 | 933 | 804 | 810 | 1008 | 805 | 939 | 798 | 810 | 1014 |
| Genes with signal peptides | 275 | 274 | 263 | 274 | 255 | 263 | 277 | 256 | 275 | 267 | 255 | 285 |

TABLE 7

Operons associated with antimicrobial production that differ among Bacillus strains.

| Metabolite/Function | No. of genes | Size (kb) | 747 | 1104 | 1541 | 1781 | 1999 | 2018 | 2084 | LSSA01 | 3A-P4 | 22C-P1 | 15A-P4 | Bs27 |
|---|---|---|---|---|---|---|---|---|---|---|---|---|---|---|
| Presumptive Lantibiotic 1 | 13 | 15.6 | + | + | − | + | − | + | − | − | + | − | − | − |
| Presumptive Lantibiotic 2 | 7 | 9.5 | − | − | + | − | − | − | − | − | − | − | − | − |
| Bacillomycin D | 4 | 30.2 | − | − | + | − | + | − | + | + | − | − | + | + |
| Iturin A | 4 | 30.2 | + | + | − | + | − | + | − | − | + | + | − | − |
| Plispastatin (formerly fengycin) | 5 | 37.6 | + | + | + | + | + | + | + | + | + | + | + | − |
| Presumptive Gramicidin | 8 | 31.5 | + | − | − | + | − | − | − | − | − | − | − | − |
| Presumptive non-ribosomal antimicrobial | 6 | 17.5 | − | − | − | − | + | − | + | + | − | − | − | − |
| Plantazolicin | 11 | 9.96 | − | − | − | − | + | − | + | + | − | − | − | − |
| Bacitracin Export 2 | 2 | 2.7 | − | + | − | − | − | − | − | − | + | + | − | − |

A related gene cluster containing genes annotated as lanthionine synthetases was present in strains 747, 1781, 1104, 2018 and the previously known strain 3A-P4. A seven gene cluster containing lanthionine synthetases was unique to 1541. A polyketide synthesizing region, presumptively identified as gramicidin, was present only in 747 and 1781.

All the strains were predicted to produce an Iturin A-like non-ribosomally synthesized lipopeptide, but for some strains the genes were more similar to Bacillomycin D producers and for the others Iturin A producers. Genes predicted to code for plipastatin (formerly known as fengycin) were absent in strain Bs27, but present in the others. Genes for a presumptive non-ribosomally synthesized antimicrobial and plantazolicin, a post-translationally modified peptide, were detected in the 1999 and the previously known strains 2084 and LSSA01.

Genes annotated as bacitractin transporters, which are predicted to export one or more of the antimicrobials produced, were present in all strains, however a second region was present in 1104, 3A-P4 and 22C-P1.

There were some antimicrobial-associated gene clusters that were present in all the strains compared. These regions were not identical but had a nucleotide similarity greater than 97% across the region. These were two non-ribosomally synthesized lipopeptides, surfactin and bacilysin, and three polyketides, bacillaene, macrolactin and difficidin. The post-translationally modified peptide, amylocyclin, as well as the siderophore, bacillibactin, were also present in all strains.

Variation analysis to annotate single nucleotide polymorphism (SNP), multiple nucleotides polymorphism (MNP) and insertion or the deletion of bases (indel) sequence variation between closely related strains, was run in PATRIC to identify differences between 1999 and the previously known strains 2084 and LSSA01, as well as the two Bacillus strains 747 and 1781, according to one embodiment of the present invention. In total 60 high-quality variants were found between the Bacillus strain 1999, according to the present invention, and the two commercially available strains 2084 and LSSA01 as shown below in Table 8.

TABLE 8

Nucleotide (nt) variations between Bacillus strain 1999, according to the present invention and prior strains 2084 and LSSA01 showing the amino acid (aa) substitutions and the functions of the genes affected by the genetic differences between the three strains.

| Genome Position in 1999 | 1999 nt | 2084 nt | LSSA01 nt | Type of Amino Acid Substitution | 1999 nt | Var nt | 1999 aa | Var aa | Function |
|---|---|---|---|---|---|---|---|---|---|
| 233023 | T | C | T | Synonymous | gta | gtG | V | V | Lincomycin-resistance |
| 313465 | CAAT | TAAC | TAAC | Synonymous | tacaat | taTAAC | YN | YN | Surfactin production and competence |
| 313534 | C | T | T | Synonymous | gac | gaT | D | D | Surfactin production and competence |
| 314473 | A | C | A | Synonymous | gca | gcC | A | A | Surfactin production and competence |
| 314488 | G | C | G | Synonymous | cc g | ccC | P | P | Surfactin production and competence |
| 314725 | TGAAAG | CGAAA | CGAAA | Nonsynonymous | attgaagcg | atCGAAAcg | IEA | IET | Surfactin production and competence |
| 627977 | A | G | G | | | | | | Intergenic region |
| 710497 | T | A | A | Nonsynonymous | cag | cTg | Q | L | Glutamine synthetase family protein |

TABLE 8 -continued

Nucleotide (nt) variations between *Bacillus* strain 1999, according to the present invention and prior strains 2084 and LSSA01 showing the amino acid (aa) substitutions and the functions of the genes affected by the genetic differences between the three strains.

| Genome Position in 1999 | 1999 nt | 2084 nt | LSSA01 nt | Type of Amino Acid Substitution | 1999 nt | Var nt | 1999 aa | Var aa | Function |
|---|---|---|---|---|---|---|---|---|---|
| 710690 | T | T | C | Nonsynonymous | agc | Ggc | S | G | Glutamine synthetase family protein |
| 710721 | C | G | C | Nonsynonymous | cag | caC | Q | H | Glutamine synthetase family protein |
| 710727 | CA AC AG GC | TAAC TGGT | TAAC TGGT | Nonsynonymous | ggcctgt tg | gACCAG TTA | GL L | DQ L | Glutamine synthetase family protein |
| 710747 | AC | AGC | AGC | Insertion | ccgttt | ccGCTtt | PF | PL | Glutamine synthetase family protein |
| 710770 | G | T | T | Nonsynonym ous | gct | gAt | A | D | Glutamine synthetase family protein |
| 714445 | A | G | G | Synonymous | att | atC | I | I | Peptidase S8 and S53, subtilisin, kexin, sedolisin |
| 714451 | C | G | G | Synonymous | cc g | ccC | P | P | Peptidase S8 and S53, subtilisin, kexin, sedolisin |
| 714490 | A | C | C | Synonymous | gct | gcG | A | A | Peptidase S8 and S53, subtilisin, kexin, sedolisin |
| 714547 | A | T | T | Synonymous | gtt | gtA | V | V | Peptidase S8 and S53, subtilisin, kexin, sedolisin |
| 1502309 | A | G | A | Synonymous | ggt | ggC | G | G | 2-oxoglutarate dehydrogenase E1 component (EC 1.2.4.2) |
| 2243964 | C | G | C | Nonsynonymous | ggc | gCc | G | A | Stage V sporulation protein AD (SpoVAD) |
| 2264062 | G | A | G | Nonsynonymous | atg | atA | M | I | YqkD |
| 2306297 | A | C | C | Nonsynonymous | ttc | Gtc | F | V | Polyketide synthase |
| 2306325 | T | G | G | Synonymous | aca | acC | T | T | Polyketide synthase |
| 2306658 | A | A | G | Synonymous | att | atC | I | I | Polyketide synthase |
| 2306765 | C | T | T | Nonsynonymous | ggc | Agc | G | S | Polyketide synthase |
| 2306778 | G | A | A | Synonymous | tac | taT | Y | Y | Polyketide synthase |
| 2306791 | G | G | T | Nonsynonymous | gcg | gAg | A | E | Polyketide synthase |
| 2306812 | C | C | T | Nonsynonymous | ggt | gAt | G | D | Polyketide synthase |
| 2306817 | C | C | T | Synonymous | ccg | ccA | P | P | Polyketide synthase |
| 2306827 | C | C | T | Nonsynonymous | cgg | cAg | R | Q | Polyketide synthase |
| 2306882 | A | A | G | Nonsynonymous | tgt | Cgt | C | R | Polyketide synthase |
| 2307018 | A | A | G | Synonymous | gct | gcC | A | A | Polyketide synthase |
| 2307048 | G | G | A | Synonymous | tcc | tcT | S | S | Polyketide synthase |
| 2307210 | C | A | C | Synonymous | tcg | tcT | S | S | Polyketide synthase |
| 2307077 | T | T | A | Nonsynonymous | act | Tct | T | S | Polyketide synthase |

TABLE 8 -continued

Nucleotide (nt) variations between *Bacillus* strain 1999, according to the present invention and prior strains 2084 and L

TABLE 8 -continued

Nucleotide (nt) variations between *Bacillus* strain 1999, according to the present invention and prior strains 2084 and LSSA01 show Conclusions. An in depth comparison of the genomes of the *Bacillus* strains, according to one embodiment of the present invention, to previously commercially available strains indicates that there are multiple genetic differences between all the strains. Functionally and genetically, the *Bacillus* strains, according to one embodiment of the present invention, are different to the previously commercially available strains.

Example 8

The Inhibition of APEC by a Direct Fed *Bacillus* Strain, According to One Embodiment of the Present Invention, is Maintained Over Time Introduction. Avian colibacillosis is a disease in chickens caused by avian pathogenic *Escherichia coli* (APEC). Controlling or reducing rates of colibacillosis in the commercial poultry industry can have a significant economic impact (Georgopoulou et al., 2005). Some strains of *Bacillus* have been shown to be effective in preventing and controlling disease in poultry (La Ragione et al., 2001; La Ragione and Woodward, 2003) This is likely in part due to antimicrobial compounds commonly produced and secreted by many *Bacillus* species such as polyketides, lipopeptides and bacteriocins (Tagg et al., 1976). Five *Bacillus* strains have been isolated and selected for their antimicrobial properties against *Clostridium perfringens* and APEC. By surveying the level of APEC in the gastrointestinal tracts of turkeys from a US commercial complex before and after treatment with the *Bacillus* DFM product, according to one embodiment of the present invention, a significant reduction in APEC after treatment was detected and a maintenance of said reduction for successive flocks.

Design. Three gastrointestinal tracts (GIT) from turkeys were sampled from a variety of houses representing an array of ages within a commercial turkey complex in three separate sampling events: one before implementation of the *Bacillus* DFM product, according to one embodiment of the present invention, another 10 months after implementation, and final sampling one year and 6 months after implementation. Sampling 1 consisted of 60 GITs, sampling 2 had 30 GITs, and sampling 3 had 30 GITs.

Materials and Methods. Direct fed microbial: Treated birds were given feed supplemented with a formulation of *Bacillus* strains 1104 (50%) and 1781 (50%) at a final concentration of $1.5 \times 10^5$ CFU/g of finished feed over the entire period.

Processing of Gastrointestinal Tracts: Selected turkeys were sacrificed and the gastrointestinal tracts from the duodenal loop to the cloaca were removed and transported in sterile Whirl-pak® bags on ice. Upon arrival, 10 cm sections of the duodenum, jejunum, and ilium were rinsed with ~5 mL sterile 0.1% peptone broth, cut longitudinally, and combined in a sterile, filtered whirl-pak bag. 99 mL of sterile 0.1% peptone was added to the bag then the sections were masticated at 300 rmp, for 1 min. Serial dilutions were made and pour plated in duplicate with both CHROMagar™ ECC to enumerate total *E. coli*.

APEC Screening: Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company, Franklin Lakes, N.J.) if possible. Genomic DNA was extracted from each isolate using the following gDNA extraction method: Add 20 μL of lysozyme (100 mg/mL) to 500 μL of overnight growth in TSB and incubate at 37° C. for 30 min, add 300 μL of lysis buffer (6 M Guanidine, 20% Triton-X 100, 10 mM Tris-HCl, pH 7.5) and incubate at 25° C. for 15 min, add 20 μl of Protease K 800 U/ml (NEB, Ipswich, Mass.) and incubate at 55° for 30 min, transfer 400 μL of lysate to a Wizard® SV 96 Binding Plate (Promega, Fitchburg, Wis.) and continue with manufacturer's filtration instructions from Wizard® SV 96 Genomic DNA Purification System starting from step 3.C.4 (4/15/revision) (Promega, Fitchburg, Wis.).

APEC pathotype was determined using multiplex polymerase chain reaction (mPCR). In order to be considered APEC, an *E. coli* isolate had to contain at least two of the five following APEC-associated virulence genes in its genome: hlyF, ompT, iroN, iss, iutA. Each reaction mixture contained 4 mM magnesium chloride (Invitrogen, Carlsbad, Calif.), 0.25 mM deoxynucleoside triphosphates (Invitrogen, Carlsbad, Calif.), 0.25 μM each primer (Eurofins, Brussels, Belgium), and 1 U Platinum® Taq DNA Polymerase (Invitrogen, Carlsbad, Calif.) and 5 μL of template gDNA (Johnson et al., 2008). The reaction was run on an Applied Biosystems Veriti® Thermal Cycler (ThermoFisher Scientific, Milwaukee, Wis.) with the following protocol: 94° C. for 2 min; 25 cycles of 94° C. for 30 s, 63° C. for 30 s, 68° C. for 3 min; and a final cycle of 72° C. for 10 min. The mPCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

Counts and Statistics: Pathotype levels for each bird were determined by multiplying the weight-adjusted presumptive CFU/g counts by the percent of presumptive isolates from each bird that were revealed to be APEC. Birds that did not produce any detectable *E. coli* colonies on agar plates or birds that did not produce any confirmed APEC strains through screening were assigned a value of 0 CFU/g.

Statistical significance for the comparison of the three samplings was determined using a one-way ANOVA multiple analysis. Significant difference threshold was set at $P<0.05$.

Figure 5:
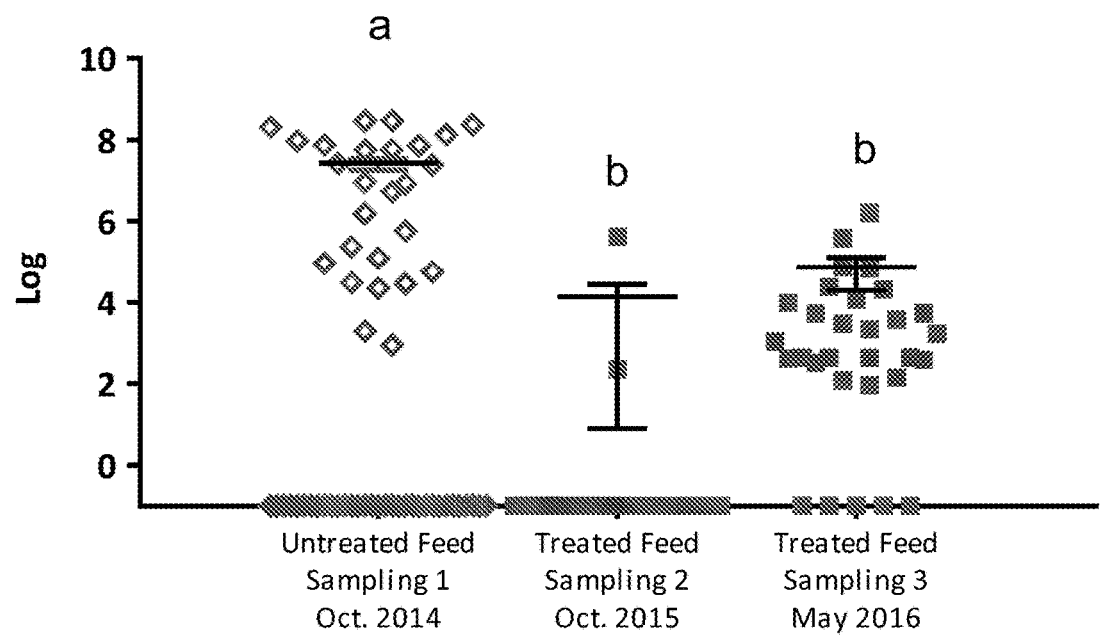
FIG. 5: Levels (CFU/g) of APEC in turkey GITs from untreated birds (sampling 1) and birds treated with a direct fed microbial product according to one embodiment of the present invention (samplings 2 & 3). Black lines indicate mean with SEM. Superscripts of different letters denote significance ($P<0.05$ by one-way ANOVA multiple comparison analysis).

Results. The APEC counts represented in CFU/g of tissue are shown in FIG. 5. Birds tested pre-DFM had an average APEC level of $2.7 \times 10^7$ CFU/g, while DFM-treated birds from samplings 2 and 3 had significantly lower levels with $1.4 \times 10^4$ CFU/g and $7.5 \times 10^4$ CFU.g, respectively. While the $3^{rd}$ sampling exhibited a higher average level of APEC, this difference was not significant.

Discussion. These data demonstrate significant reduction of APEC levels in turkey GITs fed the *Bacillus* DFM product, according to one embodiment of the present invention. They also show that the APEC inhibitory capacity of the DFM persists over time. Our research shows that including the *Bacillus* DFM product, according to one embodiment of the present invention, in feed is effective in reducing APEC prevalence in turkeys, therefore decreasing the disease-burden in commercial turkey operations.

Example 9

Pathogen Levels Rebound After the *Bacillus* DFM Product, According to One Embodiment of the Present Invention, is Removed from Feed Introduction. The gastrointestinal-associated pathogens *Clostridium perfringens* and avian pathogenic *Escherichia coli* (APEC) can have significant negative ramifications on the productivity of commercial broiler operations (Georgopoulou et al., 2005) *C. perfringens* strains that produce alpha toxin are categorized as the *C. perfringens* Type A toxinotype and cause necrotic enteritis in poultry which increases mortality and reduces weight gain (Immerseel et al., 2004). APEC is a causative agent for colibacillosis in birds in the form of airsacculitis, cellulitis, pericarditis, or perihepatitis (Barnes H J et al., 2008). Colibacillosis infections are of considerable concern for the poultry industry as they are the responsible for high rates of bird death and are the most reported reason for processing rejection (Yogaratnam, 1995). Controlling or reducing rates of NE and colibacillosis in the commercial broiler industry can increase efficiency and productivity which may bare substantial economic impacts for poultry growers. Some strains of *Bacillus* have been shown to be effective in preventing and controlling disease in poultry (La Ragione and Woodward, 2003; La Ragione et al., 2001). This is likely in part due to antimicrobial compounds commonly produced and secreted by many *Bacillus* species (Tagg et al., 1976). Five *Bacillus* strains selected for their antimicrobial properties against *Clostridium perfringens* and avian pathogenic *E. coli* (APEC) were isolated by the inventors. These five *Bacillus* strains were commercialized for use as DFM in poultry feed. By surveying pathogens in the gastrointestinal tracts of broilers from a commercial complex before, during, and after treatment with the *Bacillus* DFM product, according to one embodiment of the present invention, a significant reduction in both *C. perfringens* and APEC during treatment and a numerical increase in APEC was detected, and a significant increase in *C. perfringens* after the product was removed from feed.

Design. Three gastrointestinal tracts (GIT) from broilers were sampled from a variety of houses representing an array of ages within a commercial broiler complex in four separate sampling events: samplings 1 and 2—before implementation of the *Bacillus* DFM product, according to one embodiment of the present invention, sampling 3—during implementation, and sampling 4—off the *Bacillus* DFM product, according to one embodiment of the present invention. Sampling 1 consisted of 28 GITs, sampling 2 had 30 GITs, sampling 3 had 28 GITs, and sampling 4 had 36 GITs.

Materials and Methods. Direct fed microbial: Treated birds were given feed supplemented with a formulation of *Bacillus* strains 1104 (50%) and 1781 (50%) at a final concentration of $1.5\times10^5$ CFU/g of finished feed.

Processing of Gastrointestinal Tracts: For each sampling, selected broilers were sacrificed and the gastrointestinal tracts from the duodenal loop to the cloaca were removed and transported in sterile Whirl-pak® bags on ice. Upon arrival, 10 cm sections of the duodenum, jejunum, and ilium were rinsed with ~5 mL sterile 0.1% peptone broth, cut longitudinally, and combined in a sterile, filtered whirl-pak bag. 99 mL of sterile 0.1% peptone was added to the bag then the sections were masticated at 300 rmp, for 1 min. Serial dilutions were made and pour plated in duplicate with both CHROMagar™ ECC to enumerate *E. coli*, and *perfringens* TSC agar base (Oxoid™) with D-cycloserine (Sigma, 400 mg/L) for *Clostridium* enumeration.

APEC Screening: Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company, Franklin Lakes, N.J.) if possible. Genomic DNA was extracted from each isolate using the following gDNA extraction method: Add 20 μL of lysozyme (100 mg/mL) to 500 μL of overnight growth in TSB and incubate at 37° C. for 30 min, add 300 μL of lysis buffer (6 M Guanidine, 20% Triton-X 100, 10 mM Tris-HCl, pH 7.5) and incubate at 25° C. for 15 min, add 20 μl of Protease K 800 U/ml (NEB, Ipswich, Mass.) and incubate at 55° for 30 min, transfer 400 μL of lysate to a Wizard® SV 96 Binding Plate (Promega, Fitchburg, Wis.) and continue with manufacturer's filtration instructions from Wizard® SV 96 Genomic DNA Purification System starting from step 3.C.4 (4/15/revision) (Promega, Fitchburg, Wis.).

APEC pathotype was determined using multiplex polymerase chain reaction (mPCR). In order to be considered APEC, an *E. coli* isolate had to contain at least two of the five following APEC-associated virulence genes in its genome: hlyF, ompT, iroN, iss, iutA. Each reaction mixture contained 4 mM magnesium chloride (Invitrogen, Carlsbad, Calif.), 0.25 mM deoxynucleoside triphosphates (Invitrogen, Carlsbad, Calif.), 0.25 μM each primer (Eurofins, Brussels, Belgium), and 1 U Platinum® Taq DNA Polymerase (Invitrogen, Carlsbad, Calif.) and 5 μL of template gDNA (Johnson et al., 2008). The reaction was run on an Applied Biosystems Veriti® Thermal Cycler (ThermoFisher Scientific, Milwaukee, Wis.) with the following protocol: 94° C. for 2 min; 25 cycles of 94° C. for 30 s, 63° C. for 30 s, 68° C. for 3 min; and a final cycle of 72° C. for 10 min. The mPCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

*C. perfringens* Type A Screening: Presumptive *C. perfringens* isolates appear black on *perfringens* TSC agar base. All black colonies were counted and recorded as presumptive *C. perfringens* CFU/g counts. Five isolated black colonies from each bird were picked and grown in RCM broth (Oxoid™) if possible. Genomic DNA was extracted from each isolate using the Roche Applied Science High Pure PCR Template Kit.

*C. perfringens* toxinotype was determined using polymerase chain reaction (PCR) to amplify the alpha toxin gene. In order for an isolate to be considered *Clostridium perfringens* Type A it had to contain the alpha toxin gene, otherwise it was categorized as a non-*perfringens Clostridium*. Each reaction mixture contained 2.5 μL 10×PCR buffer (Invitrogen, Carlsbad, Calif.), 1.6 μL magnesium chloride (Invitrogen, Carlsbad, Calif.), 0.5 μL deoxynucleoside triphosphates (Invitrogen, Carlsbad, Calif.), 100 pmol primers (Eurofins, Brussels, Belgium), and 1 U Platinum® Taq DNA Polymerase (Invitrogen, Carlsbad, Calif.) and 2 μL of template gDNA, 7.8 μL of $ddH_2O$ (Yoo et al., 1997). The reaction was run on an Applied Biosystems Veriti® Thermal Cycler (ThermoFisher Scientific, Milwaukee, Wis.) with the following protocol: 5 min at 94° C., followed by 30 incubation cycles consisting of 1 min at 55° C., 1 min at 72° C., and 1 min at 94° C. The PCR product was then run through capillary gel electrophoresis using a Fragment Analyzer™ from Advance Analytical Technologies, Inc. and visualized on PROsize 2.0 (Advanced Analytical Technologies, Inc., Ames, Iowa).

Counts and Statistics: Pathotype levels for each bird were determined when the weight-adjusted presumptive CFU/g counts were multiplied by the ratio of total presumptive to pathogenic isolates (*C. perfringens* or APEC) and then log-transformed. Birds that did not yield any detectable colonies on agar plates or birds that did not produce any confirmed pathogens through screening were assigned a value of 0 CFU/g. D Statistical significance for the comparison of the four samplings was determined using a one-way ANOVA multiple analysis. Significant difference threshold was set at P<0.05.

Figure 6:
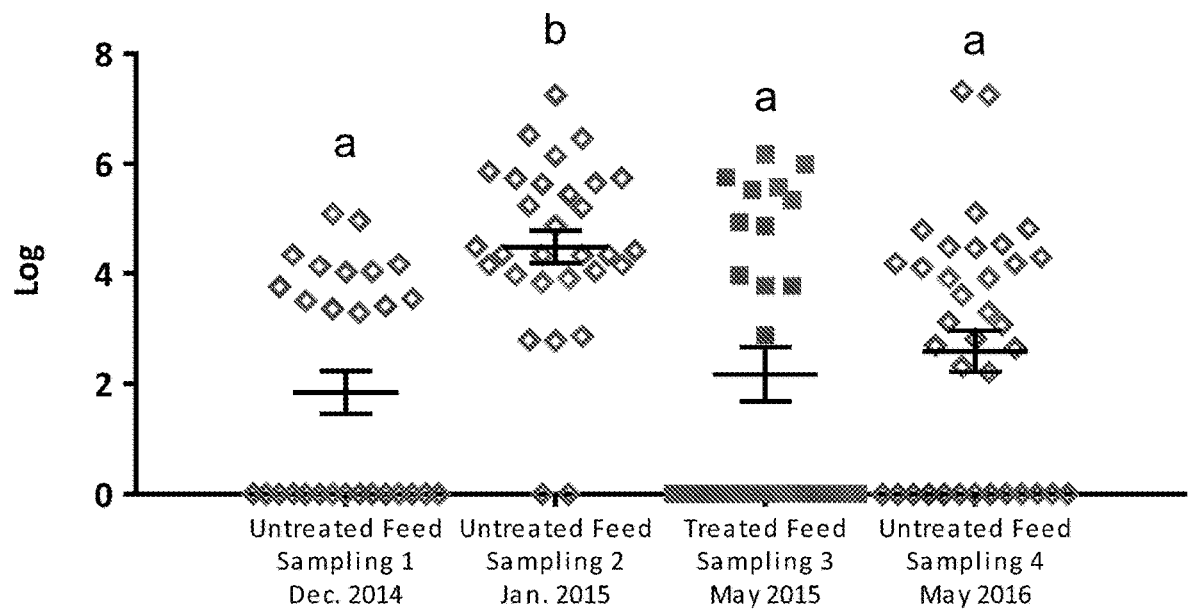
FIG. 6: Levels (CFU/g) of APEC in broiler GITs from untreated birds (samplings 1, 2 and 4) and birds treated with a direct fed microbial product according to one embodiment of the present invention (sampling 3). Superscript with different letters denote significance ($P<0.05$ by one-way ANOVA multiple comparison analysis)
Figure 7:
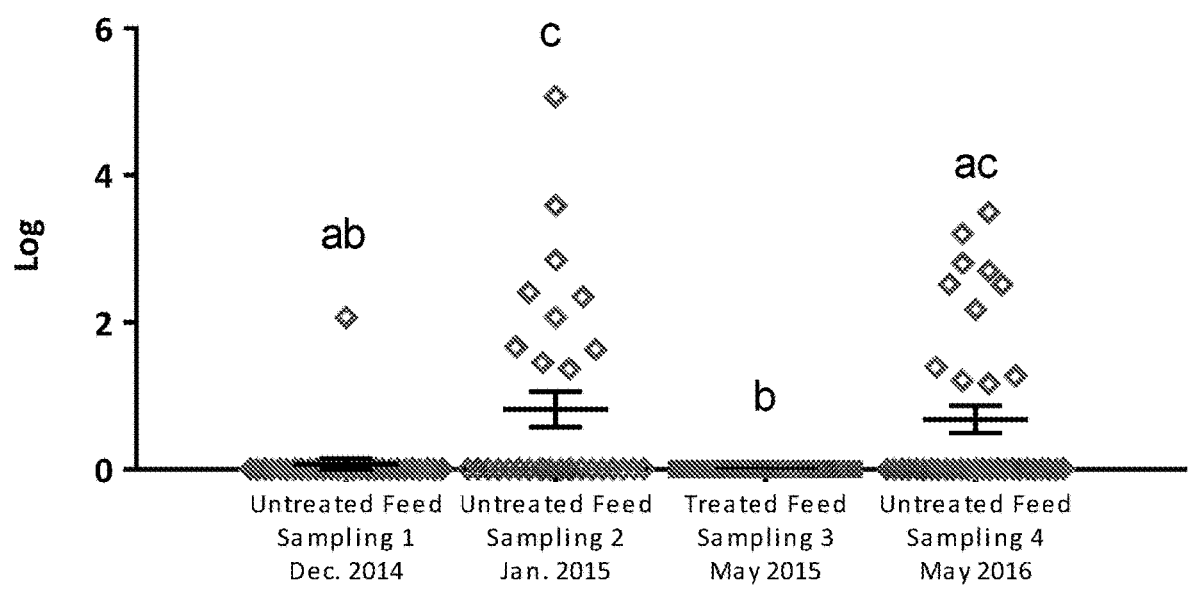
FIG. 7: Levels (CFU/g) of *Clostridium perfringens* in broiler GITs from untreated birds (samplings 1, 2 and 4) and birds treated with a direct fed microbial product according to one embodiment of the present invention (sampling 3). Superscript with different letters denote significance ($P<0.05$ by one-way ANOVA multiple comparison analysis)

Results. The pathogen counts represented in CFU/g of tissue are shown in FIGS. 6 and 7. APEC levels significantly increased from sampling 1 to sampling 2 with average APEC levels of $7.0 \times 10^2$ and $3.0 \times 10^4$ CFU/g, respectively. APEC levels were then significantly lowered in the birds treated with a DFM product, according or one embodiment of the present invention, in sampling 3 with an average of $1.5 \times 10^3$ CFU/g and then increased, though not significantly, in sampling 4 with an average level of $3.9 \times 10^3$ CFU/g.

Clostridium perfringens levels of treated birds in sampling 3 were below detectable limits for all birds, making levels of treated birds significantly lower than those of sampling 2 and sampling 4, which exhibited averages of 6.5 and 4.8 CFU/g, respectively, and numerically lower than sampling 1 which yielded an average of 1.2 CFU/g.

Discussion. Comparison of APEC and C. perfringens levels between sampling 1 and sampling 2 shows a significant upward trend indicating that flock gastrointestinal health was becoming increasingly burdened during that time. DFM-treated birds in sampling 3 showed a significantly decreased enteric pathogen load (both APEC and C. perfringens), reversing the trend and providing strong evidence that the Bacillus DFM product, according to one embodiment of the present invention, has an effective capacity to inhibit APEC and C. perfringens. Additionally, after the product was removed from feed (sampling 4), both APEC and C. perfringens levels increased, supplying further evidence that the Bacillus DFM product, according to one embodiment of the present invention, positively modulates the gastrointestinal health of broilers, with respect to APEC and C. perfringens. Reduction of these pathogens can reduce cases of disease in broilers such as avian colibacillosis and necrotic enteritis, diseases which present significant financial liability to the poultry industry. Our research shows that including the Bacillus DFM product, according to one embodiment of the present invention, in feed is effective in reducing APEC and C. perfringens prevalence in broilers, therefore decreasing the disease-burden in commercial broiler operations.

Example 10

Intestinal Immunity

Introduction. Bacillus sp. have been tested as DFMs in commercial poultry applications and have been shown to improve performance, positively modulate intestinal microbiota, inhibit pathogen colonization and improve nutrient digestibility (La Ragione and Woodward, 2003; Lee et al., 2010; Li et al., 2016; Nguyen et al., 2015; Park and Kim, 2014, 2015; Sen et al., 2012). Limited research exists on the effects of Bacillus strains on alterations in gut immune parameters and the regulation of intestinal tight junction (TJ) protein expression. The present study was conducted with the objective of evaluating the effects of dietary supplementation the Bacillus strains identified herein, according to the present invention, on performance, gut immune response and epithelial barrier integrity in broilers.

Methods. Birds and husbandry: One hundred and forty day-old male broiler chicks (Ross/Ross) were obtained from a local hatchery (Longenecker's Hatchery, Elizabethtown, Pa.) and were randomly allocated to Petersime brooder cages. Cages were equipped with a separate feeder, water trough and a digitally controlled electrical heat source. The experimental diets in mash form and tap water were provided to the chicks ad libitum. Care and management of the birds followed recommended guidelines (FASS, 2010). All experimental protocols and procedures were approved by the Small Animal Care Committee of the Beltsville Agricultural Research Center.

Experimental design and diets: Brooder cages with chickens (0 days of age) were randomly assigned to one of the five dietary treatment groups (4 cages/treatment, total of 28 birds/treatment). Based on the treatments assigned, chickens were fed either antibiotic-free basal diets (treatment 1; controls/CON) or basal diets mixed with either antibiotics or various DFM (treatment 2-5). The chickens in treatment 2 were given diets supplemented with bacitracin methylene disalicylate (BMD) at a 50 g/ton inclusion rate. The birds in the remaining three groups were fed basal diets supplemented with either Bacillus strain 1781 (treatment 3; PB1), a combination of strains 1104+747 (treatment 4; PB2) or strains 1781+747 (treatment 5; PB3). For all DFM treatments, the dose included a total of $1.5 \times 10^5$ CFU Bacillus/g of feed. For treatments with 2-strain combinations, each strain composed 50% of the total CFU count (each strain represents $7.5 \times 10^4$ CFU Bacillus/g of feed).

Body weight and feed intake measurement: The body weight of each bird was measured and recorded at 7 and 14 days of age. The feed provided was weighed and recorded throughout the experimental period. The feed intake and feed conversion ratios (FCR) for each treatment were calculated. Body weight and FCR data were used as criteria to assess the performance differences between the treatments.

Collection of intestinal samples: Six 14-day-old chickens were randomly selected from each group and used for the collection of intestine samples. Birds were euthanized by cervical dislocation and the intestines were removed immediately. A small section of the ileum from each bird was collected aseptically and stored in RNAlater® (Applied Biosystems, Foster City, Calif.) at −20° C. for further use.

Isolation of RNA and reverse transcription: Total RNA was isolated from the ileum samples stored in RNAlater® using TRIzol (Invitrogen, Carlsbad, Calif.) following the manufacturer's recommendations. Approximately 50 mg of ileal tissue was homogenized in 1 mL of TRIzol using a hand-held homogenizer (TissueRuptor; Qiagen Inc., Valencia, Calif.). Chloroform was added to the homogenized sample. The sample was centrifuged at 12,000×g for 15 minutes at 4° C. to allow phase separation. RNA present in the colorless upper aqueous phase was then precipitated with 100% isopropanol (Sigma-Aldrich Corp., St. Louis, Mo.). The RNA pellet was then washed with 75% ethanol (Sigma-Aldrich Corp. St. Louis, Mo.), air-dried and re-suspended in RNase-free water. The quantity of RNA was assessed using a NanoDrop (ND-1000) spectrophotometer (NanoDrop products, Wilmington, Del.) by measuring the absorbance at 260 nm. RNA purity was evaluated by measuring the OD260/OD280 ratio (OD=optical density). The eluted RNA was stored at −80° C. until further use. Total RNA (1 µg) was then reverse transcribed to cDNA using the QuantiTect® reverse transcription kit (Qiagen Inc., Valencia, Calif.). Briefly, the RNA sample was incubated with gDNA wipeout buffer at 42° C. for 2 minutes to remove any genomic DNA contamination. Reverse transcription (RT) of the gDNA-depleted sample was then carried out by the addition of Quantiscript Reverse Transcriptase, Quantiscript RT buffer, and RT primer mix (Qiagen Inc., Valencia, Calif.). The reaction was carried out in a thermal cycler (Mastercycler® EP Gradient S; Eppendorf, Hauppauge, N.Y.); cycling conditions were 42° C. for 30 min, followed by the inactivation of reverse transcriptase at 95° C. for 3 min. The cDNA samples were divided into aliquots and stored at −20° C.

Gene expression analysis by quantitative real-time PCR (qRT-PCR): The oligonucleotide primer sequences used for qRT-PCR are shown below in Table 10.

TABLE 10

Oligonucleotide primer sequences for qRT-PCR
(SEQ ID NOS 15-44, respectively,
in order of appearance)

| Type | Target gene | Primer sequence* (5'-3') | PCR product size (Kb) |
|---|---|---|---|
| Reference | GAPDH | F-GGTGGTGCTAAGCGTGTTAT<br>R-ACCTCTGCCATCTCTCCACA | 264 |
| Proinflammatory | IL1β | F-TGGGCATCAAGGGCTACA<br>R-TCGGGTTGGTTGGTGATG | 244 |
| | IL6 | F-CAAGGTGACGGAGGAGGAC<br>R-TGGCGAGGAGGGATTTCT | 254 |
| | IL8 | F-GGCTTGCTAGGGGAAATGA<br>R-AGCTGACTCTGACTAGGAAACTGT | 200 |
| | IL17F | F-TGAAGACTGCCTGAACCA<br>R-AGAGACCGATTCCTGATGT | 117 |
| | TNFSF15 | F-CCTGAGTATTCCAGCAACGCA<br>R-ATCCACCAGCTTGATGTCACTAAC | 292 |
| Th1 | IL2 | F-TCTGGGACCACTGTATGCTCT<br>R-ACACCAGTGGGAAACAGTATCA | 256 |
| | IFNγ | F-AGCTGACGGTGGACCTATTATT<br>R-GGCTTTGCGCTGGATTC | 259 |
| Th2 | IL4 | F-ACCCAGGGCATCCAGAAG<br>R-CAGTGCCGGCAAGAAGTT | 258 |
| | IL13 | F-CCAGGGCATCCAGAAGC<br>R-CAGTGCCGGCAAGAAGTT | 256 |
| Regulatory | IL10 | F-CGGGAGCTGAGGGTGAA<br>R-GTGAAGAAGCGGTGACAGC | 272 |
| TJ proteins | Occludin | F-GAGCCCAGACTACCAAAGCAA<br>R-GCTTGATGTGGAAGAGCTTGTTG | 68 |
| | ZO1 | F-CCGCAGTCGTTCACGATCT<br>R-GGAGAATGTCTGGAATGGTCTGA | 63 |
| | JAM2 | F-AGCCTCAAATGGGATTGGATT<br>R-CATCAACTTGCATTCGCTTCA | 59 |
| Mucin | MUC2 | F-GCCTGCCCAGGAAATCAAG<br>R-CGACAAGTTTGCTGGCACAT | 59 |

*F = Forward primer; R = Reverse primer

The various cytokines and intestinal tight junction proteins whose differential expression was evaluated in the ileum include interleukin (IL)1β, IL2, IL4, IL6, IL8, IL10, IL13, IL17F, interferon (IFN)γ, tumor necrosis factor superfamily (TNFSF)15, junctional adhesion molecule (JAM)2, occludin, zona occludens (ZO)1, and mucin2 (MUC2). The primer sequences of TJ proteins and MUC2 were adapted from Chen et al., 2015. Glyceraldehyde-3-phosphate dehydrogenase (GAPDH) was used as the reference gene. Amplification and detection were carried out using the Stratagene Mx3000P qPCR system (Agilent Technologies Inc., Santa Clara, Calif.) and the $RT^2$ SYBR Green qPCR master mix (Qiagen). Each sample was analyzed in triplicate and non-specific primer amplification was assessed by the inclusion of no template controls. Standard curves were generated using $\log_{10}$ diluted RNA and the levels of individual transcripts were normalized to those of GAPDH using the Q-gene program (Muller et al., 2002).

Data analysis: Analysis of data was carried out using one-way ANOVA with SAS software (version 9.4, SAS Institute Inc., Cary, N.C.). Results with a P-value≤0.05 were considered as significantly different. Mean separations were carried out using Duncan's multiple range test. All data were expressed as the mean±SEM for each treatment.

Figure 8:
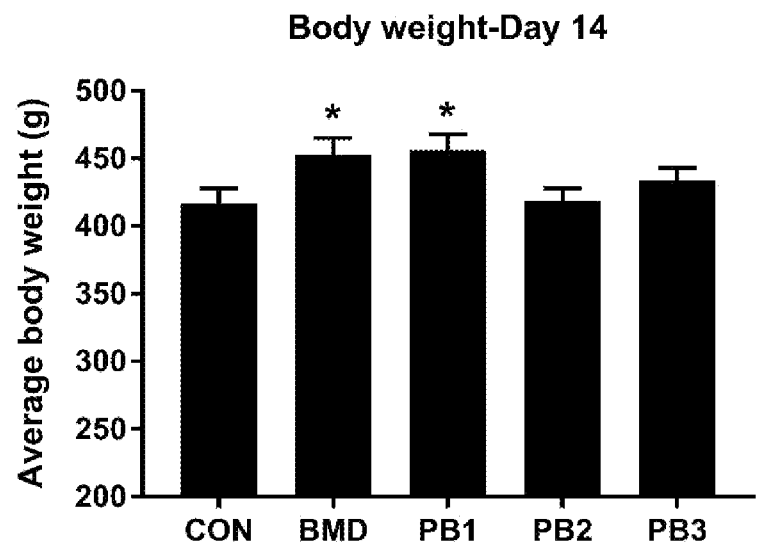
FIG. 8: Average body weight of broilers at 14 days of age. Chickens were fed basal diets (CON), diets supplemented with antibiotic (BMD) or various strains of *Bacillus* according to the present invention (PB1, PB2, PB3). The data were analyzed using one-way ANOVA and the means were separated using Duncan's multiple range test. The asterisk (*) denotes significantly increased body weights compared with controls ($P<0.05$)
Figure 9:
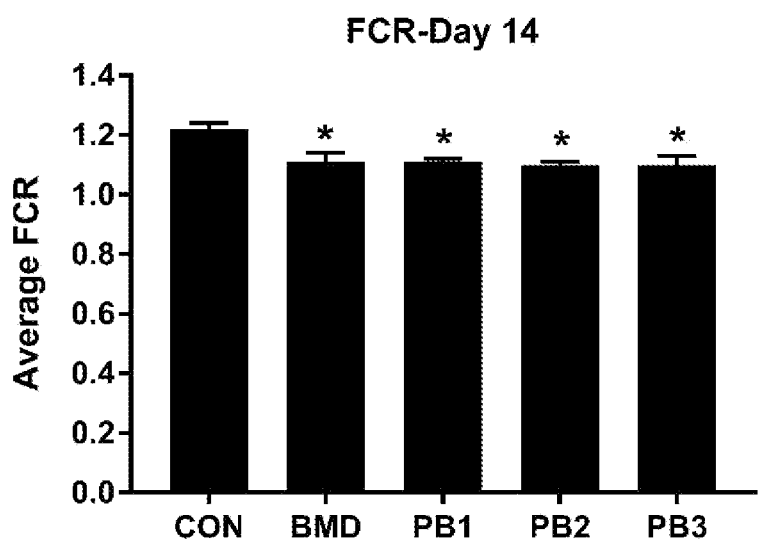
FIG. 9: Average FCR of broilers at 14 days of age. Chickens were fed either basal diets (CON), diets supplemented with antibiotic (BMD) or various strains of *B. subtilis* (PB1, PB2, PB3). The data were analyzed using one-way ANOVA and the means were separated using Duncan's multiple range test. The asterisk (*) denotes significantly increased FCR compared with controls ($P<0.05$)

Results. The body weight and FCR results at 14 days of age are presented in FIGS. 8 and 9, respectively. The birds fed diets with antibiotic (BMD) and one of the DFM strains, according to the present invention, (PB1) showed significantly higher body weights compared to those fed a basal diet (CON). There were no body weight differences in chickens fed diets supplemented with Bacillus strain combinations (PB2, PB3). The FCR was found to be significantly reduced in all chickens that were administered DFM or antibiotic treatments compared to the controls.

Figure 10:
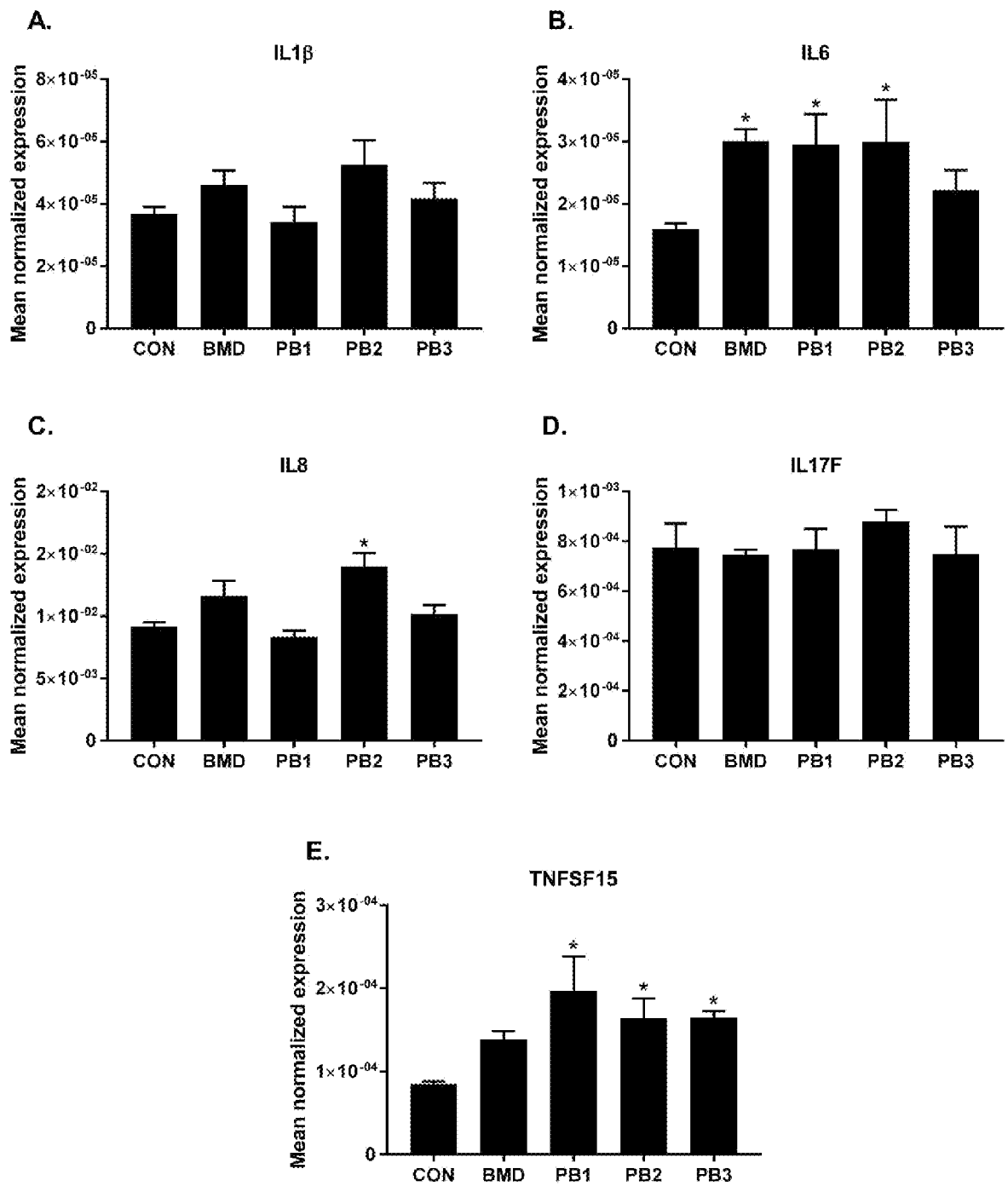
FIG. 10: Effects of dietary direct fed microbial or antibiotics on the levels of pro-inflammatory cytokine transcripts: A. IL1β, B. IL6, C. IL8, D. IL17F and E. TNFSF15. Chickens were fed either basal diets (CON), diets supplemented with antibiotic (BMD) or various strains of *Bacillus* according to the present invention (PB1, PB2, PB3). Transcript levels of various cytokines in the ileum were measured using quantitative RT-PCR and normalized to GAPDH transcript levels. The data were analyzed using one-way ANOVA and the means were separated using Duncan's multiple range test. Each bar represents the mean±SEM (n=6). The asterisk (*) denotes significantly increased expression compared with controls ($P<0.05$)

The mean normalized expression of various pro-inflammatory cytokines in the ileum are shown in FIG. 10. No differences were observed in the expression of IL1β and IL17F in any of the treatment groups receiving supplemented diets compared to controls. The levels of IL6 were found to be elevated in birds administered BMD, PB1 and PB2 treatments. IL8 expression was significantly increased in the PB2 group compared to controls. The birds fed with DFM (PB1, PB2, PB3) showed significantly increased TNFSF15 expression in the ileum compared to those given non-supplemented basal diets (CON).

Figure 11:
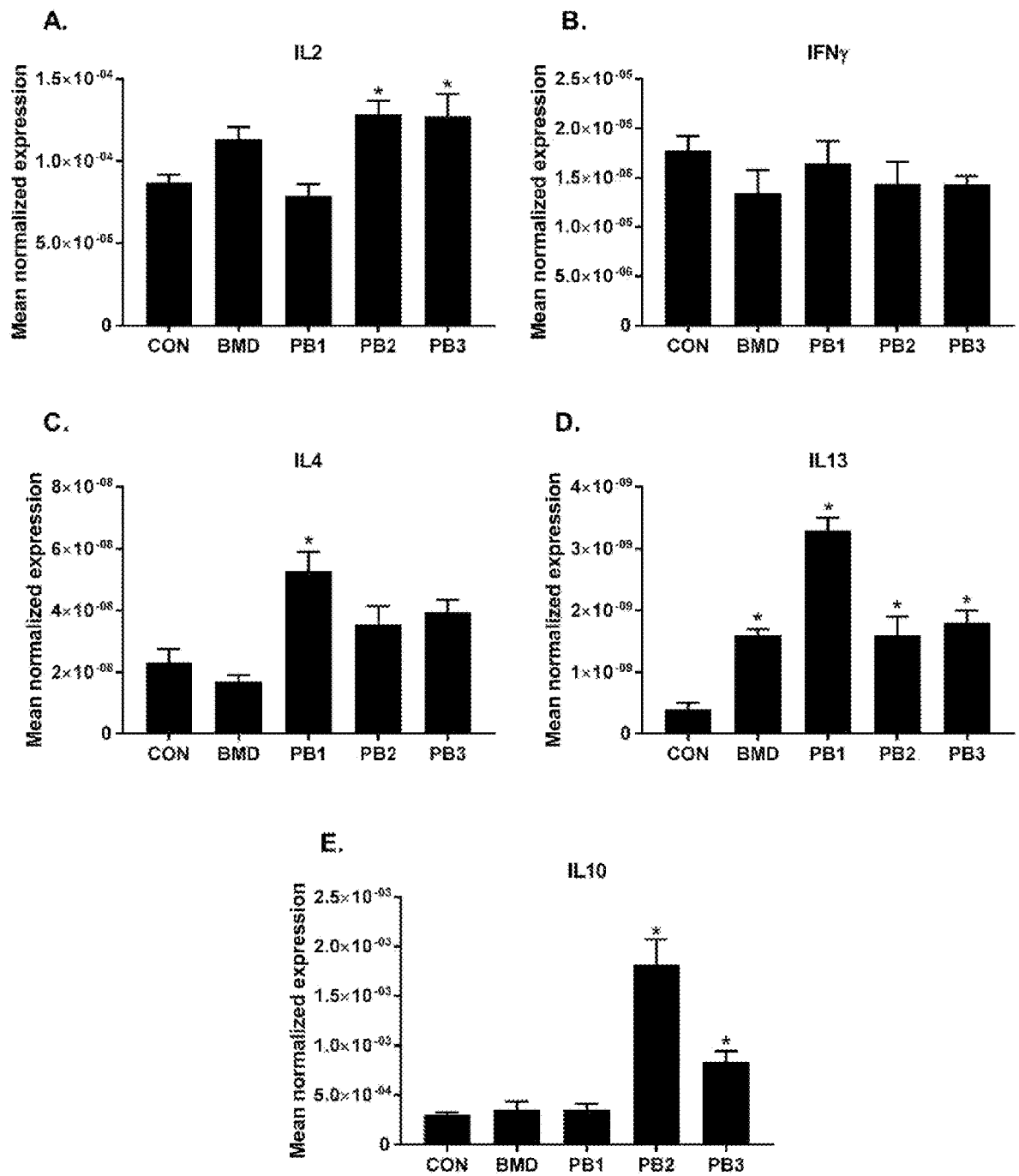
FIG. 11: Effects of dietary direct fed microbial or antibiotics on the levels of transcripts of Th1 (A. IL2, B. IFNγ), Th2 (C. IL4, D. IL13) and regulatory cytokines (E. IL10). Chickens were fed either basal diets (CON), diets supplemented with antibiotic (BMD) or various strains of *Bacillus* according to the present invention (PB1, PB2, PB3). Transcript levels of various cytokines in the ileum were measured using quantitative RT-PCR and normalized to GAPDH transcript levels. The data were analyzed using one-way ANOVA and the means were separated using Duncan's multiple range test. Each bar represents the mean±SEM (n=6). The asterisk (*) denotes significantly increased expression compared with controls ($P<0.05$)

The expression levels of various Th1 and Th2 cytokines in the ileum are presented in FIG. 11. IL2 and IL10 were found to be significantly elevated in PB2 and PB3 treatments compared to controls. The expression of IL4 was increased only in Bacillus strain 1781 supplemented birds (PB1). IL13 was increased in birds given antibiotic (BMD) or DFM (PB1, PB2, PB3) supplemented diets compared to controls. No changes were observed in the expression of IFNγ among the various treatment groups.

Figure 12:
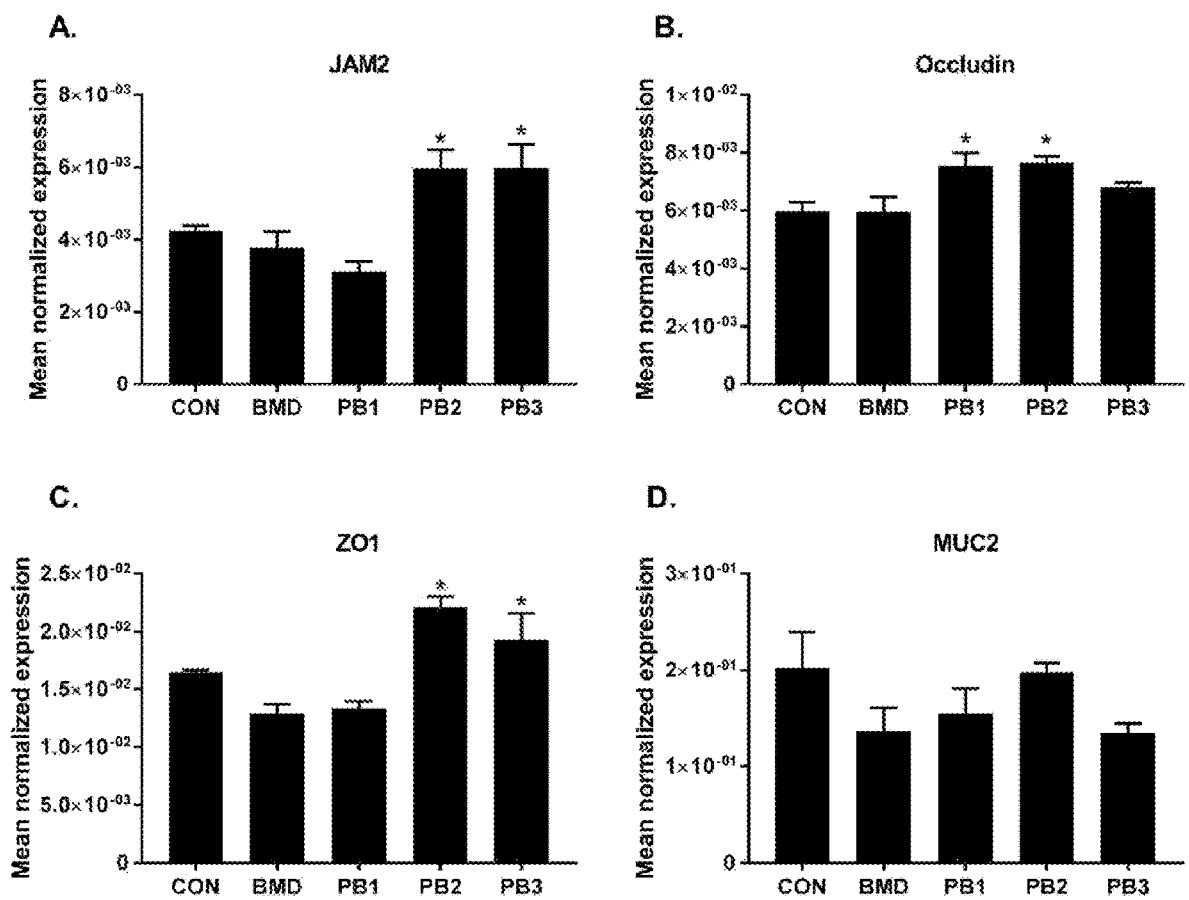
FIG. 12: Effects of dietary direct fed microbial or antibiotics on the levels of transcripts of TJ proteins (A. JAM2, B. occludin, C. ZO1) and mucin (D. MUC2). Chickens were fed either basal diets (CON), diets supplemented with antibiotic (BMD) or various strains of *Bacillus* according to the present invention (PB1, PB2, PB3). Transcript levels of various TJ proteins and mucin in the ileum were measured using quantitative RT-PCR and normalized to GAPDH transcript levels. The data were analyzed using one-way ANOVA and the means were separated using Duncan's multiple range test. Each bar represents the mean±SEM (n=6). The asterisk (*) denotes significantly increased expression compared with controls ($P<0.05$).

The expression of intestinal tight junction protein genes-JAM2 and ZO1 was significantly increased in the PB2 and PB3 groups, whereas occludin was found to be elevated in the PB2 and PB3 groups compared to the CON group. Neither the DFM nor antibiotic supplementation altered MUC2 expression in the ileum at 14 days of age as shown in FIG. 12.

Discussion. The results show that DFM (PB1)-supplemented chickens have significantly higher body weights at 14 days of age compared to non-supplemented controls and the increase in body weight observed was similar to that of antibiotic-fed chickens (BMD). The FCR was found to be significantly improved in all the supplemented groups (BMD, PB1, PB2 and PB3) compared to controls.

IL8 (CXCLi2), a chemokine and an important mediator of innate immune defense, was found to be elevated in PB2 birds. TNFSF15, a cytokine involved in the differentiation and proliferation of immune cells was found to be elevated in all DFM-fed groups (PB1, PB2, PB3. Dietary supplementation with either Bacillus strain 1781 (PB1), a combination of Bacillus strain 1104+747 (PB2) or antibiotic (BMD) significantly increased the ileal IL6 expression in broiler chickens.

In addition to the changes in the expression of various pro-inflammatory cytokines, this study also investigated the alterations occurring in T-helper (Th)1 (IL2, IFNγ), Th2 (IL4, IL13) and regulatory cytokines (IL10) in the gut following Bacillus-DFM supplementation. No differences were observed in IL2 and IFNγ expression. IL4 was found to be upregulated in the PB1 group compared to controls. IL13 expression was significantly increased in all DFM (PB1, PB2, and PB3) and antibiotic (BMD)-fed broilers compared to those fed basal diets (CON). In this study, IL10 was found to be upregulated in chickens fed diets with mixtures of DFM strains (PB2, PB3).

The effects of *Bacillus* supplementation on the expression of various intestinal TJ proteins was also investigated. The expression of occludin was found to be elevated in PB1 and PB2 groups and ZO1 and JAM2 were found to be elevated in the PB2 and PB3 groups compared to controls (CON). Increased TJ protein expression in chickens fed DFM-supplemented diets translates to increased intestinal barrier function and optimal gut health.

Conclusions. This study documented the immunomodulatory activities of *Bacillus* strains in the ileum coupled with changes in the intestinal TJ proteins. From these results, it can be concluded that supplementation of broiler diets with *Bacillus* DFM influences a diverse array of immune gut barrier functions.

It should be understood that the above description, while indicating representative embodiments of the present invention, is given by way of illustration and not of limitation. Many changes and modifications may be made within the scope of the present invention without departing from the spirit thereof, and the invention includes all such modifications.

Various additions, modifications and rearrangements are contemplated as being within the scope of the following claims, which particularly point out and distinctly claim the subject matter regarded as the invention, and it is intended that the following claims cover all such additions, modifications and rearrangements.

BIBLIOGRAPHY

Achanta, M., Sunkara, L. T., Dai, G., Bommineni, Y. R., Jiang, W., and Zhang, G. (2012). Tissue expression and developmental regulation of chicken cathelicidin antimicrobial peptides. J. Anim. Sci. Biotechnol. 3, 15.

Agunos, A., Carson, C., and Léger, D. (2013). Antimicrobial therapy of selected diseases in turkeys, laying hens, and minor poultry species in Canada. Can. Vet. J. 54, 1041-1052.

Aliakbarpour, H. R., Chamani, M., Rahimi, G., Sadeghi, A. A., and Qujeq, D. (2012). The *Bacillus subtilis* and Lactic Acid Bacteria Probiotics Influences Intestinal Mucin Gene Expression, Histomorphology and Growth Performance in Broilers. Asian-Australas. J. Anim. Sci. 25, 1285-1293.

Allen, H. K., and Stanton, T. B. (2014). Altered Egos: Antibiotic Effects on Food Animal Microbiomes. Annu. Rev. Microbiol. 68, 297-315.

Al-Sheikhly, F., and Truscott, R. B. (1977a). The interaction of *Clostridium perfringens* and its toxins in the production of necrotic enteritis of chickens. Avian Dis. 21, 256-263.

Al-Sheikhly, F., and Truscott, R. B. (1977b). The pathology of necrotic enteritis of chickens following infusion of broth cultures of *Clostridium perfringens* into the duodenum. Avian Dis. 21, 230-240.

Bai, K., Huang, Q., Zhang, J., He, J., Zhang, L., and Wang, T. (2016). Supplemental effects of probiotic *Bacillus subtilis* fmbJ on growth performance, antioxidant capacity, and meat quality of broiler chickens. Poult. Sci. pew246.

Baltzley, T., Lago, F., Neumann, T., Rehberger, T., and Gebert, S. (2010). U.S. Pat. No. 7,754,469 B2. Microorganisms and methods for treating poultry. (Waukesha, Wis.).

Barbosa, T. M., Serra, C. R., Ragione, R. M. L., Woodward, M. J., and Henriques, A. O. (2005). Screening for *Bacillus* Isolates in the Broiler Gastrointestinal Tract. Appl. Environ. Microbiol. 71, 968-978.

Barnes H. J (2008). Clostridial Diseases. Introduction. In Diseases of Poultry, Saif Y M, Fadly A A, Glisson J R, McDougald L R, Nolan L, and Swayne D E, eds. (Ames, Iowa: ISU Press), pp. 691-732.

Barnes H J, Nolan L, and Vaillancourt J-P (2008). Colibacillosis. In Diseases of Poultry, Saif Y M, Fadly A A, Glisson J R, McDougald L R, Nolan L, and Swayne D E, eds. (Ames, Iowa: ISU Press), pp. 691-732.

Billington, S. J., Wieckowski, E. U., Sarker, M. R., Bueschel, D., Songer, J. G., and McClane, B. A. (1998). *Clostridium perfringens* type E animal enteritis isolates with highly conserved, silent enterotoxin gene sequences. Infect. Immun. 66, 4531-4536.

Blom, J., Kreis, J., Spänig, S., Juhre, T., Bertelli, C., Ernst, C., and Goesmann, A. (2016). EDGAR 2.0: an enhanced software platform for comparative gene content analyses. Nucleic Acids Res. 44, W22-W28.

Cartman, S. T., Ragione, R. M. L., and Woodward, M. J. (2008). *Bacillus subtilis* Spores Germinate in the Chicken Gastrointestinal Tract. Appl. Environ. Microbiol. 74, 5254-5258.

Chen, X. H., Koumoutsi, A., Scholz, R., Eisenreich, A., Schneider, K., Heinemeyer, I., Morgenstern, B., Voss, B., Hess, W. R., Reva, O., et al. (2007). Comparative analysis of the complete genome sequence of the plant growth-promoting bacterium *Bacillus amyloliquefaciens* FZB42. Nat. Biotechnol. 25, 1007-1014.

Cheng, G., Hao, H., Xie, S., Wang, X., Dai, M., Huang, L., and Yuan, Z. (2014). Antibiotic alternatives: the substitution of antibiotics in animal husbandry? Front. Microbiol. 5.

Chowdhury, S. P., Hartmann, A., Gao, X., and Borriss, R. (2015). Biocontrol mechanism by root-associated *Bacillus amyloliquefaciens* FZB42—a review. Front. Microbiol. 6.

Cooper, K. K., and Songer, J. G. (2009). Necrotic enteritis in chickens: A paradigm of enteric infection by *Clostridium perfringens* type A. Anaerobe 15, 55-60.

Cooper, K. K., Songer, J. G., and Uzal, F. A. (2013). Diagnosing clostridial enteric disease in poultry. J. Vet. Diagn. Invest. 25, 314-327.

Darling, A. E., Mau, B., and Perna, N. T. (2010). progressiveMauve: Multiple Genome Alignment with Gene Gain, Loss and Rearrangement. PLOS ONE 5, e11147.

Fan, B., Li, L., Chao, Y., Förstner, K., Vogel, J., Borriss, R., and Wu, X.-Q. (2015). dRNA-Seq Reveals Genomewide TSSs and Noncoding RNAs of Plant Beneficial Rhizobacterium *Bacillus amyloliquefaciens* FZB42. PLoS ONE 10.

FASS (2010). Federation of Animal Science Societies—Guide for the Care and Use of Agricultural Animals in Research and Teaching, Third Edition, January 2010.

Fleischmann, R., Adams, M., White, O., Clayton, R., Kirkness, E., Kerlavage, A., Bult, C., Tomb, J., Dougherty, B., Merrick, J., et al. (1995). Whole-genome random sequencing and assembly of *Haemophilus influenzae* Rd. Science 269, 496.

Fritts, C. A., Kersey, J. H., Motl, M. A., Kroger, E. C., Yan, F., Si, J., Jiang, Q., Campos, M. M., Waldroup, A. L., and Waldroup, P. W. (2000). *Bacillus subtilis* C-3102 (Calsporin) Improves Live Performance and Microbiological Status of Broiler Chickens. J. Appl. Poult. Res. 9, 149-155.

Geeraerts, S., Delezie, E., Ducatelle, R., Haesebrouck, F., Devreese, B., and Van Immerseel, F. (2016). Vegetative Bacillus amyloliquefaciens cells do not confer protection against necrotic enteritis in broilers despite high antibacterial activity of its supernatant against *Clostridium perfringens* in vitro. Br. Poult. Sci. 57, 324-329.

Georgopoulou, J., Lordanidis, P., and Bougiouklis, P. (2005). The frequency of respiratory diseases in broiler chickens during 1992-2001. Delt. Tes Ellenikes Kteniatr. Etair. J Hell. Vet Med Soc 56, 219-227.

Glisson, J. R., Hofacre, C. L., and Mathis, G. F. (2004). Comparative efficacy of enrofloxacin, oxytetracycline, and sulfadimethoxine for the control of morbidity and mortality caused by *Escherichia coli* in broiler chickens. Avian Dis. 48, 658-662.

Grave, K., Kaldhusdal, M. C., Kruse, H., Harr, L. M. F., and Flatlandsmo, K. (2004). What has happened in norway after the ban of avoparcin? Consumption of antimicrobials by poultry. Prev. Vet. Med. 62, 59-72.

Guabiraba, R., and Schouler, C. (2015). Avian colibacillosis: still many black holes. FEMS Microbiol. Lett. 362, fnv118.

Hatheway, C. L. (1990). Toxigenic clostridia. Clin. Microbiol. Rev. 3, 66-98.

Heier, B. T., Lovland, A., Soleim, K. B., Kaldhusdal, M., and Jarp, J. (2001). A field study of naturally occurring specific antibodies against *Clostridium perfringens* alpha toxin in Norwegian broiler flocks. Avian Dis. 45, 724-732.

Hibberd, M. C., Neumann, A. P., Rehberger, T. G., and Siragusa, G. R. (2011). Multilocus Sequence Typing Subtypes of Poultry *Clostridium perfringens* Isolates Demonstrate Disease Niche Partitioning. J. Clin. Microbiol. 49, 1556-1567.

Hofacre, C. L., Froyman, R., Gautrias, B., George, B., Goodwin, M. A., and Brown, J. (1998). Use of Aviguard and other intestinal bioproducts in experimental *Clostridium perfringens*-associated necrotizing enteritis in broiler chickens. Avian Dis. 42, 579-584.

Hofacre, C. L., Johnson, A. C., Kelly, B. J., and Froyman, R. (2002). Effect of a commercial competitive exclusion culture on reduction of colonization of an antibiotic-resistant pathogenic *Escherichia coli* in day-old broiler chickens. Avian Dis. 46, 198-202.

Hong, H. A., Duc, L. H., and Cutting, S. M. (2005). The use of bacterial spore formers as probiotics. FEMS Microbiol. Rev. 29, 813-835.

Immerseel, F. V., Buck, J. D., Pasmans, F., Huyghebaert, G., Haesebrouck, F., and Ducatelle, R. (2004). *Clostridium perfringens* in poultry: an emerging threat for animal and public health. Avian Pathol. 33, 537-549.

Immerseel, F. V., Rood, J. I., Moore, R. J., and Titball, R. W. (2009). Rethinking our understanding of the pathogenesis of necrotic enteritis in chickens. Trends Microbiol. 17, 32-36.

Jeong, J. S., and Kim, I. H. (2014). Effect of *Bacillus subtilis* C-3102 spores as a probiotic feed supplement on growth performance, noxious gas emission, and intestinal microflora in broilers. Poult. Sci. 93, 3097-3103.

Jeong, H., Park, S.-H., and Choi, S.-K. (2015). Genome Sequence of Antibiotic-Producing *Bacillus amyloliquefaciens* Strain KCTC 13012. Genome Announc. 3.

Jiang, Z., Schatzmayr, G., Mohnl, M., and Applegate, T. J. (2010). Net effect of an acute phase response—Partial alleviation with probiotic supplementation. Poult. Sci. 89, 28-33.

Johnson, T. J., Wannemuehler, Y., Doetkott, C., Johnson, S. J., Rosenberger, S. C., and Nolan, L. K. (2008). Identification of Minimal Predictors of Avian Pathogenic *Escherichia coli* Virulence for Use as a Rapid Diagnostic Tool. J. Clin. Microbiol. 46, 3987-3996.

Jost, B. H., Billington, S. J., Trinh, H. T., Bueschel, D. M., and Songer, J. G. (2005). Atypical cpb2 Genes, Encoding Beta2-Toxin in *Clostridium perfringens* Isolates of Non-porcine Origin. Infect. Immun. 73, 652-656.

Kaldhusdal, M., and Løvland, A. (2000). The economical impact of *Clostridium perfringens* is greater than anticipated. World Poult. 16, 50-51.

Kaldhusdal, M., Benestad, S. L., and Løvland, A. (2016). Epidemiologic aspects of necrotic enteritis in broiler chickens—disease occurrence and production performance. Avian Pathol. 45, 271-274.

Kearse, M., Moir, R., Wilson, A., Stones-Havas, S., Cheung, M., Sturrock, S., Buxton, S., Cooper, A., Markowitz, S., Duran, C., et al. (2012). Geneious Basic: An integrated and extendable desktop software platform for the organization and analysis of sequence data. Bioinformatics 28, 1647-1649.

Kennedy, C. L., Krejany, E. O., Young, L. F., O'Connor, J. R., Awad, M. M., Boyd, R. L., Emmins, J. J., Lyras, D., and Rood, J. I. (2005). The α-toxin of *Clostridium septicum* is essential for virulence: α-toxin of *Clostridium septicum*. Mol. Microbiol. 57, 1357-1366.

Keyburn, A. L., Boyce, J. D., Vaz, P., Bannam, T. L., Ford, M. E., Parker, D., Di Rubbo, A., Rood, J. I., and Moore, R. J. (2008). NetB, a New Toxin That Is Associated with Avian Necrotic Enteritis Caused by *Clostridium perfringens*. PLoS Pathog. 4, e26.

Keyburn, A. L., Bannam, T. L., Moore, R. J., and Rood, J. I. (2010a). NetB, a pore-forming toxin from necrotic enteritis strains of *Clostridium perfringens*. Toxins 2, 1913-1927.

Keyburn, A. L., Yan, X.-X., Bannam, T. L., Van Immerseel, F., Rood, J. I., and Moore, R. J. (2010b). Association between avian necrotic enteritis and *Clostridium perfringens* strains expressing NetB toxin. Vet. Res. 41, 21.

Koumoutsi, A., Chen, X.-H., Henne, A., Liesegang, H., Hitzeroth, G., Franke, P., Vater, J., and Borriss, R. (2004). Structural and Functional Characterization of Gene Clusters Directing Nonribosomal Synthesis of Bioactive Cyclic Lipopeptides in *Bacillus amyloliquefaciens* Strain FZB42. J. Bacteriol. 186, 1084-1096.

La Ragione, R. M., and Woodward, M. J. (2003). Competitive exclusion by *Bacillus subtilis* spores of *Salmonella enterica* serotype Enteritidis and *Clostridium perfringens* in young chickens. Vet. Microbiol. 94, 245-256.

La Ragione, R. M., Casula, G., Cutting, S. M., and Woodward, M. J. (2001). *Bacillus subtilis* spores competitively exclude *Escherichia coli* O78:K80 in poultry. Vet. Microbiol. 79, 133-142.

Lazarus, B., Paterson, D. L., Mollinger, J. L., and Rogers, B. A. (2015). Do Human Extraintestinal *Escherichia coli* Infections Resistant to Expanded-Spectrum Cephalosporins Originate From Food-Producing Animals? A Systematic Review. Clin. Infect. Dis. 60, 439-452.

Lee, K. W., Lee, S. H., Lillehoj, H. S., Li, G. X., Jang, S. I., Babu, U. S., Park, M. S., Kim, D. K., Lillehoj, E. P., Neumann, A. P., et al. (2010). Effects of direct-fed microbials on growth performance, gut morphometry, and immune characteristics in broiler chickens. Poult. Sci. 89, 203-216.

Lee, K. W., Lillehoj, H. S., Jeong, W., Jeoung, H. Y., and An, D. J. (2011a). Avian necrotic enteritis: Experimental models, host immunity, pathogenesis, risk factors, and vaccine development. Poult. Sci. 90, 1381-1390.

Lee, K.-W., Li, G., Lillehoj, H. S., Lee, S.-H., Jang, S. I., Babu, U. S., Lillehoj, E. P., Neumann, A. P., and Siragusa, G. R. (2011b). *Bacillus subtilis*-based direct-fed microbials augment macrophage function in broiler chickens. Res. Vet. Sci. 91, e87-e91.

Lee, K. W., Lillehoj, H. S., Jang, S. I., Lee, S. H., Bautista, D. A., and Siragusa, G. R. (2013). Effect of *Bacillus subtilis*-based Direct-fed Microbials on Immune Status in Broiler Chickens Raised on Fresh or Used Litter. Asian-Australas. J. Anim Sci. 26, 1592-1597.

Lee, K.-W., Lillehoj, H. S., Jang, S. I., and Lee, S.-H. (2014). Effects of salinomycin and *Bacillus subtilis* on growth performance and immune responses in broiler chickens. Res. Vet. Sci. 97, 304-308.

Li, B., Li, Q., Xu, Z., Zhang, N., Shen, Q., and Zhang, R. (2014). Responses of beneficial *Bacillus amyloliquefaciens* SQR9 to different soilborne fungal pathogens through the alteration of antifungal compounds production. Front. Microbiol. 5.

Li, Y., Xu, Q., Huang, Z., Lv, L., Liu, X., Yin, C., Yan, H., and Yuan, J. (2016). Effect of *Bacillus subtilis* CGMCC 1.1086 on the growth performance and intestinal microbiota of broilers. J. Appl. Microbiol. 120, 195-204.

Lovland, A., Kaldhusdal, M., and Reitan, L. J. (2003). Diagnosing *Clostridium perfringens*-associated necrotic enteritis in broiler flocks by an immunoglobulin G anti-alpha-toxin enzyme-linked immunosorbent assay. Avian Pathol. 32, 527-534.

Lovland, A., Kaldhusdal, M., Redhead, K., Skjerve, E., and Lillehaug, A. (2004). Maternal vaccination against subclinical necrotic enteritis in broilers. Avian Pathol. 33, 81-90.

Lu, J., Idris, U., Harmon, B., Hofacre, C., Maurer, J. J., and Lee, M. D. (2003). Diversity and Succession of the Intestinal Bacterial Community of the Maturing Broiler Chicken. Appl. Environ. Microbiol. 69, 6816-6824.

Luo, C., Liu, X., Zhou, H., Wang, X., and Chen, Z. (2015a). Nonribosomal Peptide Synthase Gene Clusters for Lipopeptide Biosynthesis in *Bacillus subtilis* 916 and Their Phenotypic Functions. Appl. Environ. Microbiol. 81, 422-431.

Luo, C., Liu, X., Zhou, X., Guo, J., Truong, J., Wang, X., Zhou, H., Li, X., and Chen, Z. (2015b). Unusual Biosynthesis and Structure of Locillomycins from *Bacillus subtilis* 916. Appl. Environ. Microbiol. 81, 6601-6609.

Marsh, T. L., Saxman, P., Cole, J., and Tiedje, J. (2000). Terminal Restriction Fragment Length Polymorphism Analysis Program, a Web-Based Research Tool for Microbial Community Analysis. Appl. Environ. Microbiol. 66, 3616-3620.

Maurer, J. J., Hofacre, C. L., Wooley, R. E., Gibbs, P., and Froyman, R. (2002). Virulence factors associated with *Escherichia coli* present in a commercially produced competitive exclusion product. Avian Dis. 46, 704-707.

Moran, E. T. (2014). Intestinal events and nutritional dynamics predispose *Clostridium perfringens* virulence in broilers. Poult. Sci. 93, 3028-3036.

Muller, P. Y., Janovjak, H., Miserez, A. R., and Dobbie, Z. (2002). Processing of gene expression data generated by quantitative real-time RT-PCR. BioTechniques 32, 1372-1374, 1376, 1378-1379.

Neumann, A. P., and Rehberger, T. G. (2009). MLST analysis reveals a highly conserved core genome among poultry isolates of *Clostridium septicum*. Anaerobe 15, 99-106.

Neumann, A. P., Dunham, S. M., Rehberger, T. G., and Siragusa, G. R. (2010). Quantitative real-time PCR assay for *Clostridium septicum* in poultry gangrenous dermatitis associated samples. Mol. Cell. Probes 24, 211-218.

Nguyen, A. t. v., Nguyen, D. v., Tran, M. t., Nguyen, L. t., Nguyen, A. h., and Phan, T.-N. (2015). Isolation and characterization of *Bacillus subtilis* CH16 strain from chicken gastrointestinal tracts for use as a feed supplement to promote weight gain in broilers. Lett. Appl. Microbiol. 60, 580-588.

Niilo, L. (1980). *Clostridium perfringens* in Animal Disease: A Review of Current Knowledge. Can. Vet. J. 21, 141-148.

Nurk, S., Bankevich, A., Antipov, D., Gurevich, A., Korobeynikov, A., Lapidus, A., Prjibelsky, A., Pyshkin, A., Sirotkin, A., Sirotkin, Y., et al. (2013). Assembling Genomes and Mini-metagenomes from Highly Chimeric Reads. In Research in Computational Molecular Biology, M. Deng, R. Jiang, F. Sun, and X. Zhang, eds. (Springer Berlin Heidelberg), pp. 158-170.

Park, J. H., and Kim, I. H. (2014). Supplemental effect of probiotic *Bacillus subtilis* B2A on productivity, organ weight, intestinal *Salmonella* microflora, and breast meat quality of growing broiler chicks. Poult. Sci. 93, 2054-2059.

Park, J. H., and Kim, I. H. (2015). The effects of the supplementation of *Bacillus subtilis* RX7 and B2A strains on the performance, blood profiles, intestinal *Salmonella* concentration, noxious gas emission, organ weight and breast meat quality of broiler challenged with *Salmonella typhimurium*. J. Anim. Physiol. Anim. Nutr. 99, 326-334.

Patterson, J. A., and Burkholder, K. M. (2003). Application of prebiotics and probiotics in poultry production. Poult. Sci. 82, 627-631.

Power, E. G. (1996). RAPD typing in microbiology—a technical review. J. Hosp. Infect. 34, 247-265.

Primm, N. D., Vance, K., Wykle, L., and Hofacre, C. L. (1997). Application of normal avian gut flora by prolonged aerosolization onto turkey hatching eggs naturally exposed to *Salmonella*. Avian Dis. 41, 455-460.

Rahimi, S., Kathariou, S., Grimes, J. L., and Siletzky, R. M. (2011). Effect of direct-fed microbials on performance and *Clostridium perfringens* colonization of turkey poults. Poult. Sci. 90, 2656-2662.

Riley, M. A., Robinson, S. M., Roy, C. M., Dennis, M., Liu, V., and Dorit, R. L. (2012). Resistance is futile: the bacteriocin model for addressing the antibiotic resistance challenge. Biochem. Soc. Trans. 40, 1438-1442.

Rimoldi, G., Uzal, F., Chin, R. P., Palombo, E. A., Awad, M., Lyras, D., and Shivaprasad, H. L. (2015). Necrotic Enteritis in Chickens Associated with *Clostridium sordellii*. Avian Dis. 59, 447-451.

Rood, J. I., Keyburn, A. L., and Moore, R. J. (2016). NetB and necrotic enteritis: the hole movable story. Avian Pathol. J. WVPA 45, 295-301.

Sambrook, Fritsch & Maniatis, Molecular Cloning: A Laboratory Manual, Third Edition (2001) Cold Spring Harbor Laboratory Press, Cold Spring Harbor, N.Y.

Seemann, T. (2014). Prokka: rapid prokaryotic genome annotation. Bioinformatics 30, 2068-2069.

Sen, S., Ingale, S. L., Kim, Y. W., Kim, J. S., Kim, K. H., Lohakare, J. D., Kim, E. K., Kim, H. S., Ryu, M. H., Kwon, I. K., et al. (2012). Effect of supplementation of *Bacillus subtilis* LS 1-2 to broiler diets on growth performance, nutrient retention, caecal microbiology and small intestinal morphology. Res. Vet. Sci. 93, 264-268.

Shojadoost, B., Vince, A. R., and Prescott, J. F. (2012). The successful experimental induction of necrotic enteritis in chickens by *Clostridium perfringens*: a critical review. Vet. Res. 43, 74.

Smirnov, A., Perez, R., Amit-Romach, E., Sklan, D., and Uni, Z. (2005). Mucin Dynamics and Microbial Populations in Chicken Small Intestine Are Changed by Dietary Probiotic and Antibiotic Growth Promoter Supplementation. J. Nutr. 135, 187-192.

Snoeyenbos, G. H., Weinack, O. M., and Smyser, C. F. (1978). Protecting chicks and poults from *Salmonellae* by oral administration of "normal" gut microflora. Avian Dis. 22, 273-287.

Songer, J. G. (1996). Clostridial enteric diseases of domestic animals. Clin. Microbiol. Rev. 9, 216-234.

Tagg, J. R., Dajani, A. S., and Wannamaker, L. W. (1976). Bacteriocins of gram-positive bacteria. Bacteriol. Rev. 40, 722-756.

Tam, N. K. M., Uyen, N. Q., Hong, H. A., Duc, L. H., Hoa, T. T., Serra, C. R., Henriques, A. O., and Cutting, S. M. (2006). The Intestinal Life Cycle of *Bacillus subtilis* and Close Relatives. J. Bacteriol. 188, 2692-2700.

Tellez, G., Pixley, C., Wolfenden, R. E., Layton, S. L., and Hargis, B. M. (2012). Probiotics/direct fed microbials for *Salmonella* control in poultry. Food Res. Int. 45, 628-633.

Teo, A. Y.-L., and Tan, H.-M. (2005) Inhibition of *Clostridium perfringens* by a Novel Strain of *Bacillus subtilis* Isolated from the Gastrointestinal Tracts of Healthy Chickens. Appl. Environ. Microbiol. 71, 4185-4190.

Timbermont, L., Haesebrouck, F., Ducatelle, R., and Immerseel, F. V. (2011). Necrotic enteritis in broilers: an updated review on the pathogenesis. Avian Pathol. 40, 341-347.

Uzal, F. A., McClane, B. A., Cheung, J. K., Theoret, J., Garcia, J. P., Moore, R. J., and Rood, J. I. (2015) Animal models to study the pathogenesis of human and animal *Clostridium perfringens* infections. Vet. Microbiol. 179, 23-33.

Wattam, A., Gabbard, J., Shukla, M., and Sobral, B. (2014). Comparative Genomic Analysis at the PATRIC, A Bioinformatic Resource Center. In Host-Bacteria Interactions, A. C. Vergunst, and D. O'Callaghan, eds. (Springer New York), pp. 287-308.

Wattiau, P., Renard, M. E., Ledent, P., Debois, V., Blackman, G., and Agathos, S. N. (2001). A PCR test to identify *Bacillus subtilis* and closely related species and its application to the monitoring of wastewater biotreatment. Appl. Microbiol. Biotechnol. 56, 816-819.

Weinack, O. M., Snoeyenbos, G. H., Smyser, C. F., and Soerjadi, A. S. (1981). Competitive exclusion of intestinal colonization of *Escherichia coli* in chicks. Avian Dis. 25, 696-705.

WHO Global Strategy Recommendations http://www.who.int/drugresistance/WHO_Global_Strategy_Recommendations/en/in dex3.html.

Williams, J. G. K., Kubelik, A. R., Livak, K. J., Rafalski, J. A., and Tingey, S. V. (1990). DNA polymorphisms amplified by arbitrary primers are useful as genetic markers. Nucleic Acids Res. 18, 6531-6535.

Willoughby, D. H., Bickford, A. A., Cooper, G. L., and Charlton, B. R. (1996). Periodic Recurrence of Gangrenous Dermatitis Associated with *Clostridium Septicum* in a Broiler Chicken Operation. J. Vet. Diagn. Invest. 8, 259-261.

Wu, L., Wu, H.-J., Qiao, J., Gao, X., and Borriss, R. (2015). Novel Routes for Improving Biocontrol Activity of *Bacillus* Based Bioinoculants. Front. Microbiol. 6.

Yogaratnam, V. (1995). Analysis of the causes of high rates of carcase rejection at a poultry processing plant. Vet. Rec. 137, 215-217.

Yoo, H. S., Lee, S. U., Park, K. Y., and Park, Y. H. (1997). Molecular typing and epidemiological survey of prevalence of *Clostridium perfringens* types by multiplex PCR. J. Clin. Microbiol. 35, 228-232.

Zeriouh, H., de Vicente, A., Pérez-García, A., and Romero, D. (2014). Surfactin triggers biofilm formation of *Bacillus subtilis* in melon phylloplane and contributes to the biocontrol activity. Environ. Microbiol. 16, 2196-2211.

Zhang, Z. F., and Kim, I. H. (2014). Effects of multistrain probiotics on growth performance, apparent ileal nutrient digestibility, blood characteristics, cecal microbial shedding, and excreta odor contents in broilers. Poult. Sci. 93, 364-370.

Zhang, J., Kobert, k, Flouri, T., and Stamatakis, A. (2014). PEAR: A fast and accurate Illumina Paired-End reAd mergeR. Bioinformatics 30, 614-620.

Zhu, X. Y., Zhong, T., Pandya, Y., and Joerger, R. D. (2002). 16S rRNA-Based Analysis of Microbiota from the Cecum of Broiler Chickens. Appl. Environ. Microbiol. 68, 124-137.

Zoetendal, E. G., Collier, C. T., Koike, S., Mackie, R. I., and Gaskins, H. R. (2004). Molecular Ecological Analysis of the Gastrointestinal Microbiota: A Review. J. Nutr. 134, 465-472.

---

We claim:

1. A microbial composition comprising
   (a) at least one isolated *Bacillus* strain chosen from at least one of strains *Bacillus subtilis* 1104, deposited as NRRL B-67258; *Bacillus subtilis* 1781, deposited as NRRL B-67259; *Bacillus subtilis* 747, deposited as NRRL B-67257; *Bacillus subtilis* 1541, deposited as NRRL B-67260; and *Bacillus subtilis* 2018, deposited as NRRL B-67261; present in a concentration of about $10^5$ CFU/gram to about $10^{12}$ CFU/gram; and
   (b) a carrier;
   wherein the composition inhibits a pathogen chosen from at least one of *E. coli* and *Clostridium* when administered to an animal,
   wherein the composition is a freeze-dried composition, a spray-dried composition, or a fluidized bed dried composition.

2. The microbial composition of claim 1, wherein the carrier is selected from a group consisting of: whey, maltodextrin, sucrose, dextrose, limestone, rice hulls, and sodium silica aluminate.

3. The microbial composition of claim 2, wherein the carrier is in the physical form of a powdered solid.

4. An animal feed comprising the microbial composition of claim 1, wherein the microbial composition has concentration of the at least one isolated *Bacillus* strain in the composition of about $1\times10^8$ CFU/g.

5. A direct fed microbial composition comprising
   (a) at least one isolated *Bacillus* strain chosen from at least one of strains *Bacillus subtilis* 1104, deposited as NRRL B-67258; *Bacillus subtilis* 1781, deposited as NRRL B-67259; *Bacillus subtilis* 747, deposited as NRRL B-67257; *Bacillus subtilis* 1541, deposited as NRRL B-67260; and *Bacillus subtilis* 2018, deposited as NRRL B-67261 present in a concentration of about $10^5$ CFU/gram to about $10^{12}$ CFU/gram; and
   (b) a carrier;
   wherein the composition inhibits a pathogen chosen from at least one of *E. coli* and *Clostridium* in an animal, and
   wherein the composition is a freeze-dried composition, a spray-dried composition, or a fluidized bed dried composition.

6. The direct fed microbial composition of claim 5, wherein the composition comprises a plurality of isolated *Bacillus* strains chosen from the strains *Bacillus subtilis* 1104, deposited as NRRL B-67258; *Bacillus subtilis* 1781, deposited as NRRL B-67259; *Bacillus subtilis* 747, deposited as NRRL B-67257; *Bacillus subtilis* 1541, deposited as NRRL B-67260; and *Bacillus subtilis* 2018, deposited as NRRL B-67261.

7. The direct fed microbial composition of claim 5, wherein the carrier is selected from a group consisting of: whey, maltodextrin, sucrose, dextrose, limestone, rice hulls, and sodium silica aluminate.

8. A direct fed microbial composition comprising
   (a) at least one isolated *Bacillus* strain is chosen from at least one of strains *Bacillus subtilis* 1104, deposited as NRRL B-67258; *Bacillus subtilis* 1781, deposited as NRRL B-67259; *Bacillus subtilis* 747, deposited as NRRL B-67257; *Bacillus subtilis* 1541, deposited as NRRL B-67260; *Bacillus subtilis* 1999, deposited as NRRL B-67318; and *Bacillus subtilis* 2018, deposited as NRRL B-67261 present in a concentration of about $10^5$ CFU/gram to about $10^{12}$ CFU/gram; and
   (b) a carrier;
   wherein the at least one isolated *Bacillus* strain inhibits a pathogen chosen from at least one of *E. coli* and *Clostridium* in an animal, and
   wherein the composition is a freeze-dried composition, a spray-dried composition, or a fluidized bed dried composition.

9. The direct fed microbial composition of claim 8, wherein the composition comprises a plurality of isolated *Bacillus* strains chosen from the strains *Bacillus subtilis* 1104, deposited as NRRL B-67258; *Bacillus subtilis* 1781, deposited as NRRL B-67259; *Bacillus subtilis* 747, deposited as NRRL B-67257; *Bacillus subtilis* 1541, deposited as NRRL B-67260; *Bacillus subtilis* 1999, deposited as NRRL B-67318; and *Bacillus subtilis* 2018, deposited as NRRL B-67261.

10. The direct fed microbial composition of claim 8, wherein the carrier is selected from a group consisting of: whey, maltodextrin, sucrose, dextrose, limestone, rice hulls, and sodium silica aluminate.

* * * * *

SEQUENCE LISTING

<160> NUMBER OF SEQ ID NOS: 44

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gtagacccgt                                                          10

<210> SEQ ID NO 2
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 2
agagtttgat ymtggctcag                                              20

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taccttgtta ygactt                                                  16

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtttcgctcc                                                         10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accaacatca ttgcggctac                                              20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acctttgtag aagcagcaat ttca                                         24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcatacggaa tggcctgggg                                              20

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
acttttgttg aagttggccc g                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acagttgctg ttagtgtccc a                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacgatatcg gttcctgcgt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacatcaatc tggggcaagc                                              20

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcatatcaac taagtgtagc cgca                                         24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agacgttacg ttttccccct                                              20

<210> SEQ ID NO 14
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 14
cgggccaact tcaacaaaag                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtggtgcta agcgtgttat                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acctctgcca tctctccaca                                                    20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgggcatcaa gggctaca                                                      18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcgggttggt tggtgatg                                                      18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caaggtgacg gaggaggac                                                     19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 20
tggcgaggag ggatttct                                                  18

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcttgctag gggaaatga                                                 19

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agctgactct gactaggaaa ctgt                                           24

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgaagactgc ctgaacca                                                  18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agagaccgat tcctgatgt                                                 19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctgagtatt ccagcaacgc a                                              21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atccaccagc ttgatgtcac taac					24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctgggacca ctgtatgctc t					21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acaccagtgg gaaacagtat ca					22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agctgacggt ggacctatta tt					22

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggctttgcgc tggattc					17

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acccagggca tccagaag					18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 32
cagtgccggc aagaagtt                                                    18

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccagggcatc cagaagc                                                     17

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cagtgccggc aagaagtt                                                    18

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgggagctga gggtgaa                                                     17

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtgaagaagc ggtgacagc                                                   19

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gagcccagac taccaaagca a                                                21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```

```
gcttgatgtg aagagcttg ttg                                              23

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccgcagtcgt tcacgatct                                                  19

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggagaatgtc tggaatggtc tga                                             23

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agcctcaaat gggattggat t                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catcaacttg cattcgcttc a                                               21

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcctgcccag gaaatcaag                                                  19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 44
cgacaagttt gctggcacat                                              20
```